United States Patent
Better et al.

(10) Patent No.: US 8,721,334 B2
(45) Date of Patent: *May 13, 2014

(54) DENTAL IMPLEMENTS HAVING END MILL CUTTER SURFACES

(75) Inventors: Hadar Better, Tel Aviv (IL); Gideon Fostick, Givat Shmuel (IL); Yossi Gross, Moshav Mazor (IL); Ilan Uchitel, Kefar Saba (IL)

(73) Assignee: Maxillent Ltd., Herzliya (IL)

( * ) Notice: Subject to any disclaimer, the term of this patent is extended or adjusted under 35 U.S.C. 154(b) by 98 days.

This patent is subject to a terminal disclaimer.

(21) Appl. No.: 13/196,632

(22) Filed: Aug. 2, 2011

(65) Prior Publication Data

US 2011/0287386 A1 Nov. 24, 2011

Related U.S. Application Data

(63) Continuation of application No. 12/485,199, filed on Jun. 16, 2009, now Pat. No. 8,029,284.

(51) Int. Cl.
*A61C 3/02* (2006.01)
*A61C 8/00* (2006.01)

(52) U.S. Cl.
USPC .......................................... 433/165; 433/173

(58) Field of Classification Search
USPC .................. 433/165, 166, 172, 173, 174, 229
See application file for complete search history.

(56) References Cited

U.S. PATENT DOCUMENTS

| | | | |
|---|---|---|---|
| 2,347,567 A * | 4/1944 | Kresse | 424/487 |
| 2,436,623 A | 2/1948 | Zile | |
| 3,659,881 A | 5/1972 | Tinsley et al. | |
| 4,021,921 A | 5/1977 | Detaille | |
| 4,112,944 A | 9/1978 | Williams | |
| 4,412,825 A | 11/1983 | Tokarz | |
| 4,416,629 A | 11/1983 | Mozsary et al. | |
| 4,431,416 A | 2/1984 | Niznick | |
| 4,523,910 A | 6/1985 | Makovich | |
| 4,673,353 A | 6/1987 | Nevin | |
| 4,854,872 A | 8/1989 | Detsch | |
| 4,960,381 A | 10/1990 | Niznick | |
| 5,022,857 A | 6/1991 | Matsutani et al. | |

(Continued)

FOREIGN PATENT DOCUMENTS

| | | |
|---|---|---|
| EP | 1174094 A1 | 1/2002 |
| WO | WO2007007331 A1 | 1/2007 |

(Continued)

OTHER PUBLICATIONS

An Office Action dated Jun. 28, 2012, which issued during the prosecution of U.S. Appl. No. 13/040,440.

(Continued)

*Primary Examiner* — Ralph Lewis
(74) *Attorney, Agent, or Firm* — Fish & Richardson P.C.

(57) ABSTRACT

Apparatus is provided that includes a dental implant having a proximal implant end and a lateral external surface. The implant is shaped so as to define a lumen therethrough having a lateral opening through the lateral external surface. The apparatus further includes an applicator, which is removably coupled to the proximal implant end. The applicator includes a delivery tube having a distal tube end that is removably coupled to the implant such that the delivery tube is in fluid communication with the lumen via the lateral opening. Other embodiments are also described.

22 Claims, 35 Drawing Sheets

(56) References Cited

U.S. PATENT DOCUMENTS

| | | | |
|---|---|---|---|
| 5,047,030 A * | 9/1991 | Draenert | 606/65 |
| 5,049,125 A | 9/1991 | Accaries et al. | |
| 5,078,605 A * | 1/1992 | Sutter et al. | 433/165 |
| 5,188,488 A | 2/1993 | Nakayama et al. | |
| 5,261,818 A | 11/1993 | Shaw | |
| 5,291,914 A | 3/1994 | Bares et al. | |
| 5,312,255 A | 5/1994 | Bauer | |
| 5,366,374 A * | 11/1994 | Vlassis | 433/165 |
| 5,456,601 A | 10/1995 | Sendax | |
| 5,481,260 A | 1/1996 | Buckler et al. | |
| 5,575,650 A | 11/1996 | Niznick et al. | |
| 5,584,688 A | 12/1996 | Sakuma et al. | |
| 5,685,716 A | 11/1997 | Linkow | |
| 5,711,315 A | 1/1998 | Jerusalmy | |
| 5,759,036 A | 6/1998 | Hinds | |
| 5,782,918 A | 7/1998 | Klardie et al. | |
| 5,795,160 A | 8/1998 | Hahn et al. | |
| 5,829,977 A | 11/1998 | Rogers et al. | |
| 5,839,899 A | 11/1998 | Robinson | |
| 5,868,572 A * | 2/1999 | Lazzara et al. | 433/173 |
| 5,879,161 A | 3/1999 | Lazzara | |
| 5,915,967 A | 6/1999 | Clokie | |
| 5,967,777 A | 10/1999 | Klein et al. | |
| 5,989,025 A | 11/1999 | Conley | |
| 6,068,479 A | 5/2000 | Kwan | |
| 6,159,161 A | 12/2000 | Hodosh | |
| 6,200,289 B1 | 3/2001 | Hochman et al. | |
| 6,220,860 B1 * | 4/2001 | Hansson | 433/173 |
| 6,270,346 B1 * | 8/2001 | Grabenhofer et al. | 433/173 |
| 6,273,720 B1 | 8/2001 | Spalten | |
| 6,758,673 B2 | 7/2004 | Fromovich et al. | |
| 6,827,575 B1 | 12/2004 | Jörneus | |
| 6,939,135 B2 | 9/2005 | Sapian | |
| 7,100,476 B1 | 9/2006 | Feit | |
| 7,217,130 B2 | 5/2007 | Giorno | |
| 7,297,102 B2 | 11/2007 | Smith et al. | |
| 7,300,282 B2 | 11/2007 | Sapian | |
| 7,364,430 B2 | 4/2008 | Kitamura et al. | |
| 7,396,232 B2 | 7/2008 | Fromovich et al. | |
| 7,510,397 B2 | 3/2009 | Hochman | |
| 7,934,929 B2 * | 5/2011 | Better et al. | 433/174 |
| 8,029,284 B2 * | 10/2011 | Better et al. | 433/173 |
| 8,356,994 B2 | 1/2013 | Better et al. | |
| 8,388,343 B2 | 3/2013 | Better et al. | |
| 2003/0105469 A1 | 6/2003 | Karmon | |
| 2003/0175656 A1 | 9/2003 | Livne et al. | |
| 2003/0228556 A1 | 12/2003 | Giorno | |
| 2003/0232308 A1 | 12/2003 | Simmons | |
| 2004/0018471 A1 | 1/2004 | Giorno | |
| 2006/0020326 A9 | 1/2006 | Bolduc et al. | |
| 2006/0084034 A1 | 4/2006 | Hochman | |
| 2006/0172255 A1 * | 8/2006 | Hochman et al. | 433/144 |
| 2006/0210949 A1 | 9/2006 | Stoop | |
| 2007/0055257 A1 | 3/2007 | Vaccaro et al. | |
| 2007/0162024 A1 | 7/2007 | Siemonsmeier | |
| 2008/0108011 A1 | 5/2008 | Nahlieli | |
| 2008/0161934 A1 | 7/2008 | Yamada | |
| 2008/0213729 A1 | 9/2008 | Hochman | |
| 2008/0215010 A1 | 9/2008 | Silver et al. | |
| 2008/0293010 A1 * | 11/2008 | Song | 433/165 |
| 2008/0319466 A1 | 12/2008 | Eder | |
| 2009/0136898 A1 * | 5/2009 | Kim | 433/165 |
| 2009/0142731 A1 | 6/2009 | Kim | |
| 2009/0239200 A1 | 9/2009 | Brajnovic et al. | |
| 2010/0047733 A1 | 2/2010 | Nahlieli | |
| 2010/0081111 A1 | 4/2010 | Better et al. | |
| 2010/0196841 A1 | 8/2010 | Nahlieli et al. | |
| 2010/0266984 A1 | 10/2010 | Jung | |
| 2010/0324561 A1 | 12/2010 | Watzek et al. | |
| 2011/0008746 A1 | 1/2011 | Kim | |

FOREIGN PATENT DOCUMENTS

| | | |
|---|---|---|
| WO | WO2007114553 A1 | 10/2007 |
| WO | WO2007080595 A3 | 4/2009 |
| WO | WO2010035270 A3 | 5/2010 |

OTHER PUBLICATIONS

An International Search Report and a Written Opinion both dated Mar. 23, 2010, which issued during the prosecution of Applicant's PCT/IL09/00931.

An International Preliminary Report on Patentability dated Mar. 29, 2011, which issued during the prosecution of Applicant's PCT/IL09/00931.

Sotirakis E, "A different method for elevation of the floor of the maxillary sinus: Experimental study and reference to 1 some cases", Mediterranean Dental Implant Congress (Athens, Greece), Scientific programme MDIC 2004—an D abstract.

Chen L et al., "An 8-year retrospective study: 1,100 patients receiving 1 '557 implants using the minimally invasive hydraulic sinus condensing technique" J. Periodontol 76:482-491,2005.

Muronoi M et al., "Simplified procedure for augmentation of the sinus floor using a haemostatic nasal balloon", British Jounal of Oral & Maxillofacial Surgery 41 (2): 120-121, 2003.

Vercellotli T, "Piezoelectric surgery in implantology: a case report—a new piezoelectric ridge expansion technique", Int J Periodontics Restorative Dent 20(4):358-65, 2000—an abstract.

Vercellotli T, "The Piezoelectric bony window osteotomy and sinus membrane elevation: Intriduction of a new technique for simplification of the sinus augmentation procedure", Int J Periodontics Restorative Dent 21 (6):561-7, D 2001—an abstract.

Flanagan D, "Important arterial supply of the Mandible, Control of an Arterial Hemorrhage, and Report of a Hemorrhagic Incident", J OralImplantol29(4): 165-73,2003.

U.S. Appl. No. 60/619,542, Oct. 2004.

Riley et al., "The Episure syring: a novel loss of resistance syringe for locating the epidural space," Anesth Analg. 105 (4): 1164-6 (Oct. 2007).

An Office Action dated Oct. 16, 2012, which issued during the prosecution of U.S. Appl. No. 12/661,795.

An International Preliminary Report on Patentability dated Dec. 16, 2011, which issued during the prosecution of Applicant's PCT/IL10/00252.

An Office Action dated Mar. 19, 2013, which issued during the prosecution of U.S. Appl. No. 13/409,631.

An Office Action dated Mar. 29, 2013, which issued during the prosecution of U.S. Appl. No. 13/228,564.

An Office Action dated Jun. 24, 2013, which issued during the prosecution of U.S. Appl. No. 13/314,818.

An Office Action dated Jun. 26, 2013, which issued during the prosecution of U.S. Appl. No. 13/760,206.

An Office Action dated Jun. 26, 2013, which issued during the prosecution of U.S. Appl. No. 13/409,631.

Notice of Allowance issued Nov. 25, 2013 in U.S. Appl. No. 13/314,740.

English translation of Office Action mailed Jul. 30, 2013 in Chinese Patent Application No. 200980147751.3.

* cited by examiner

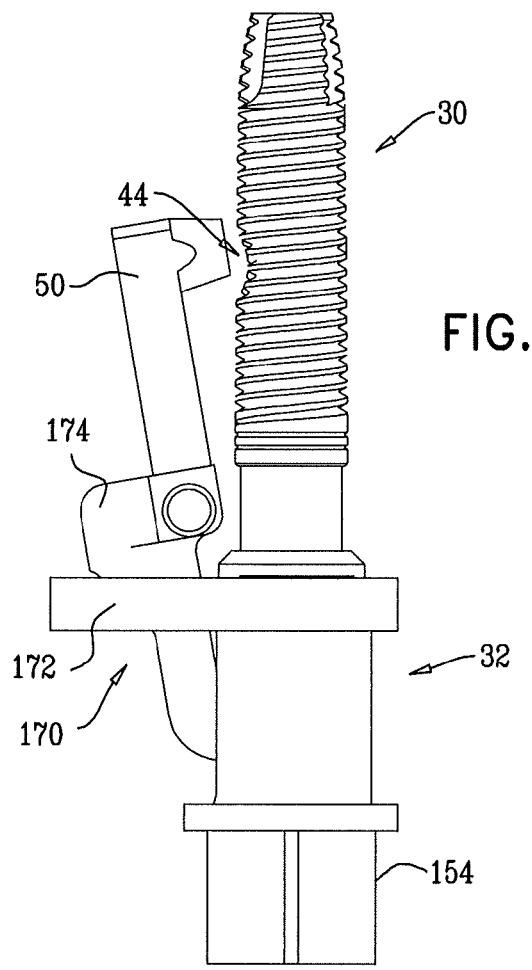
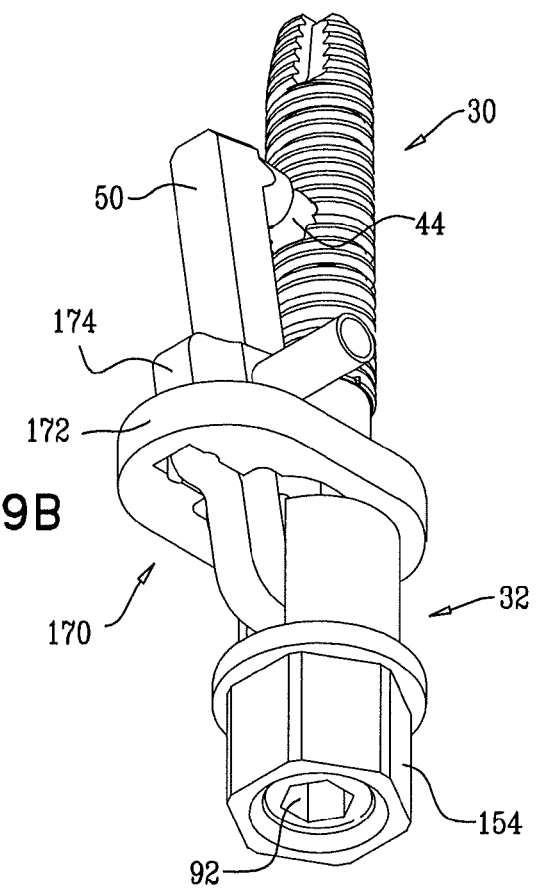

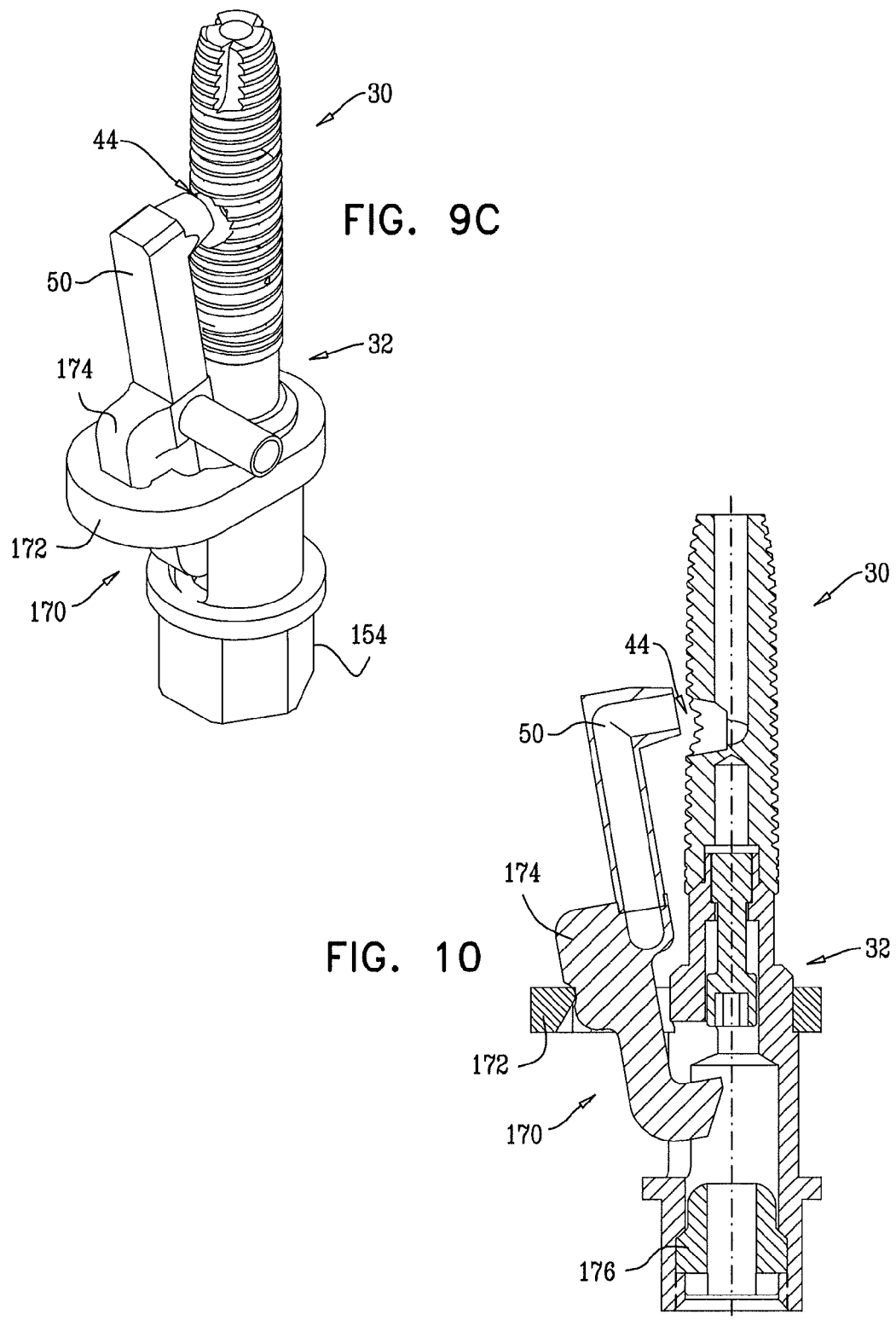

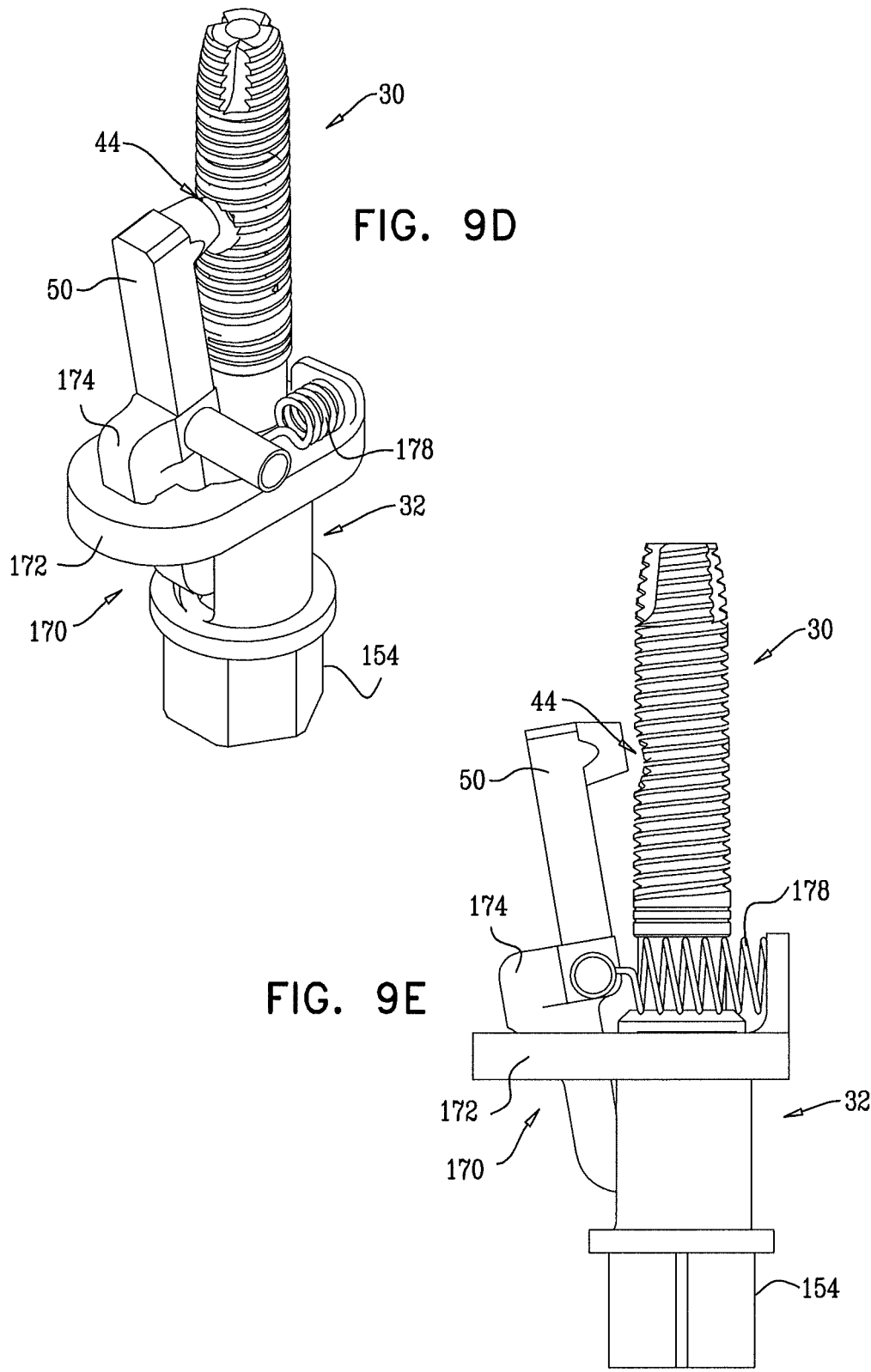

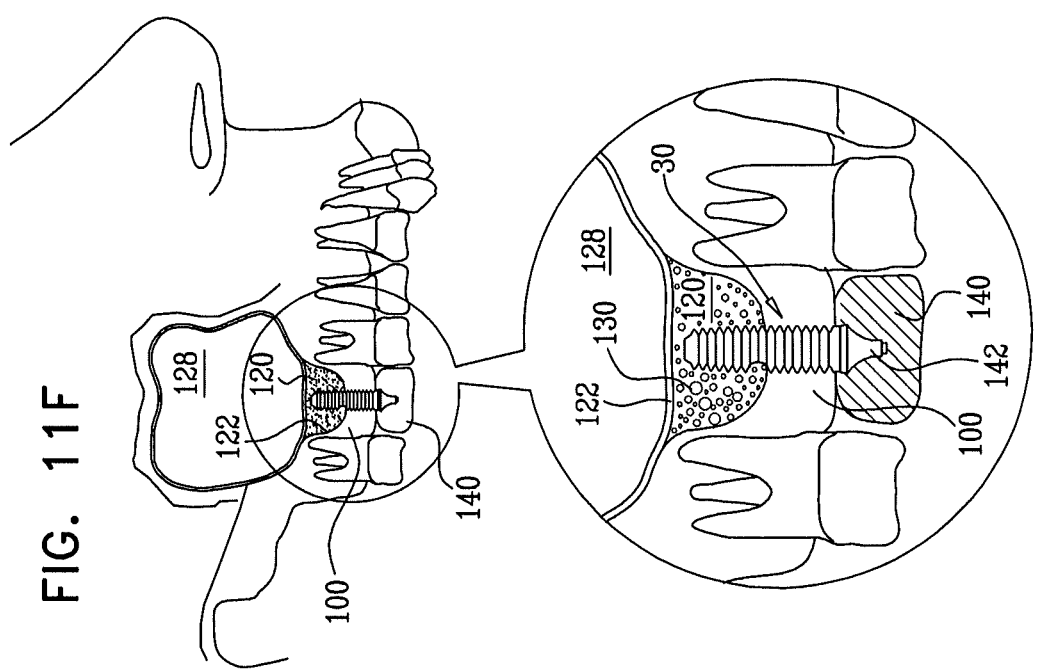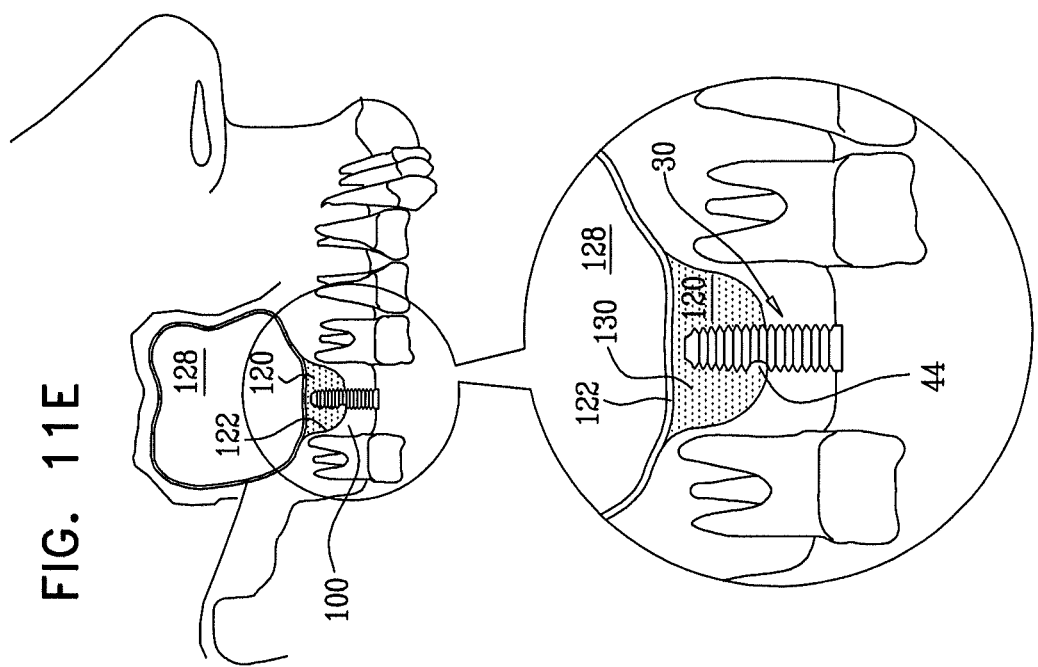

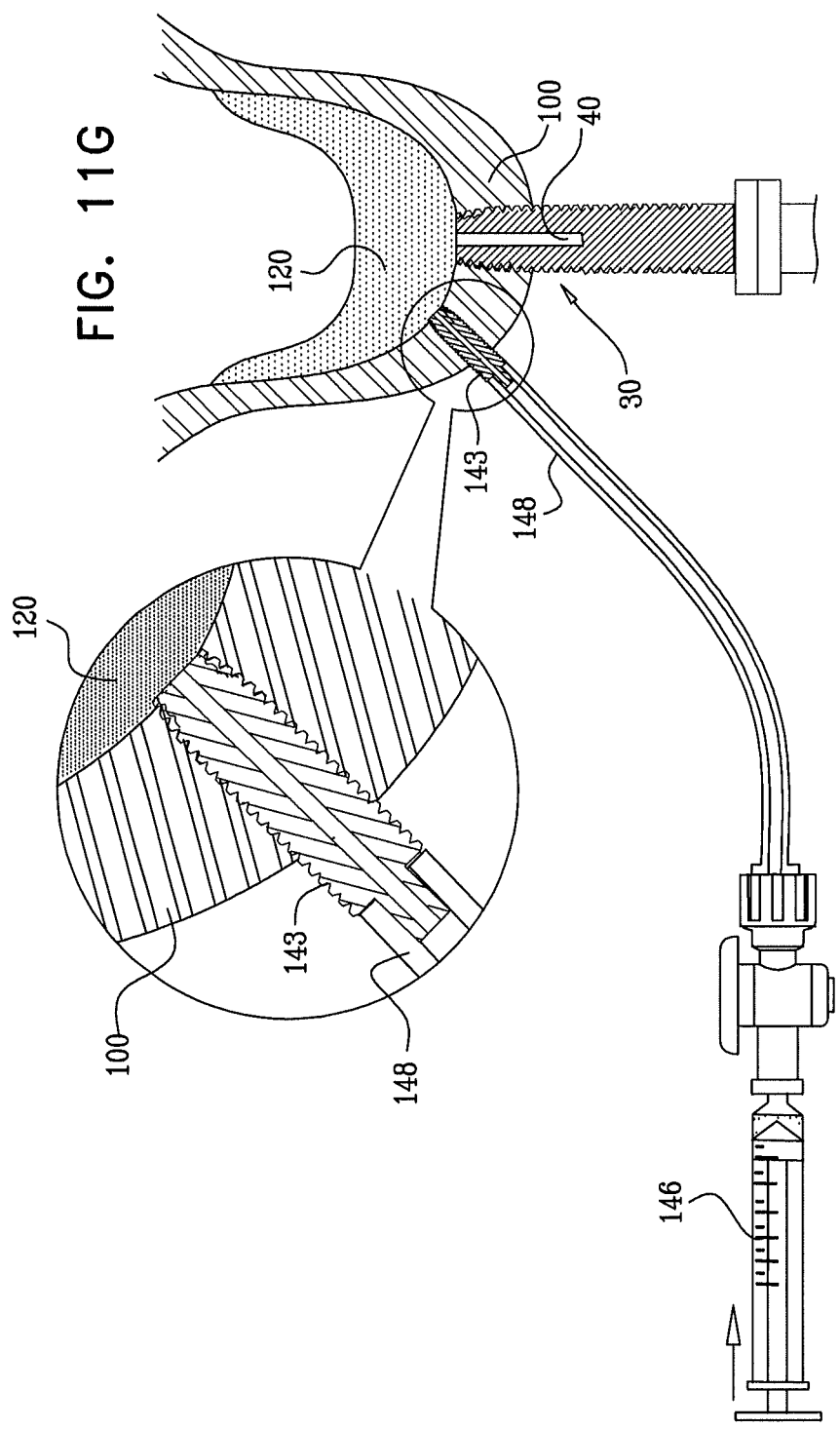

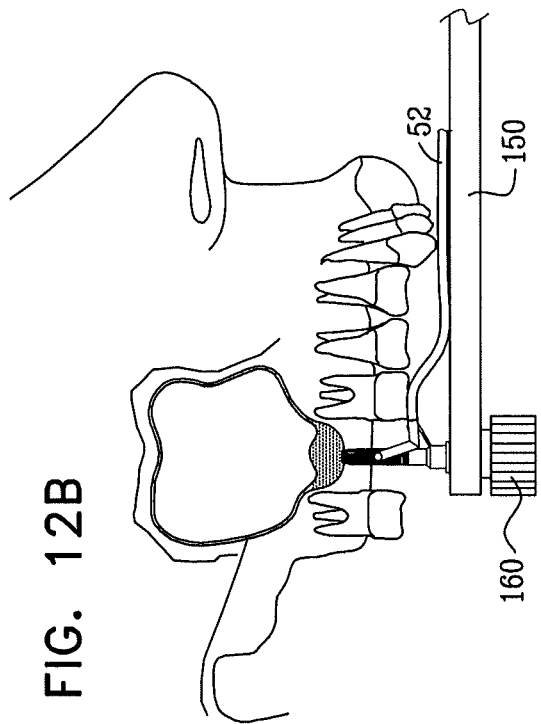
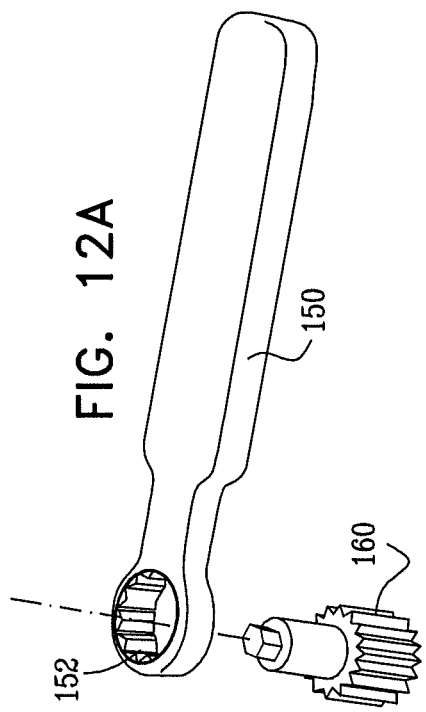

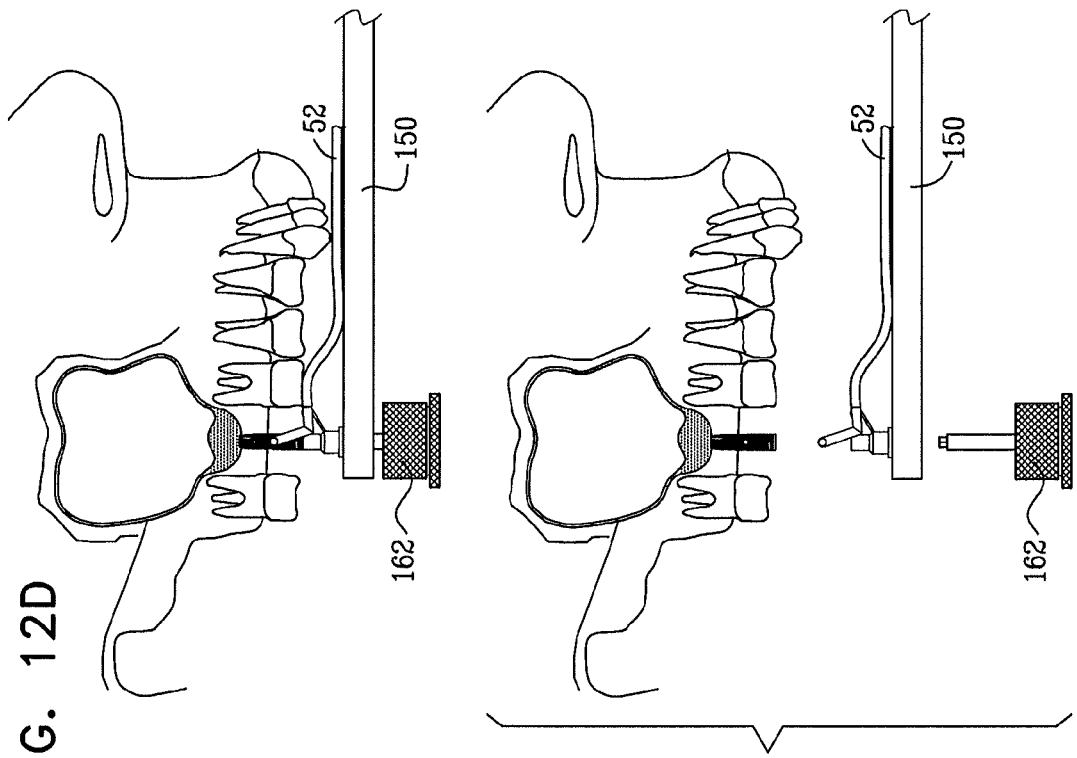
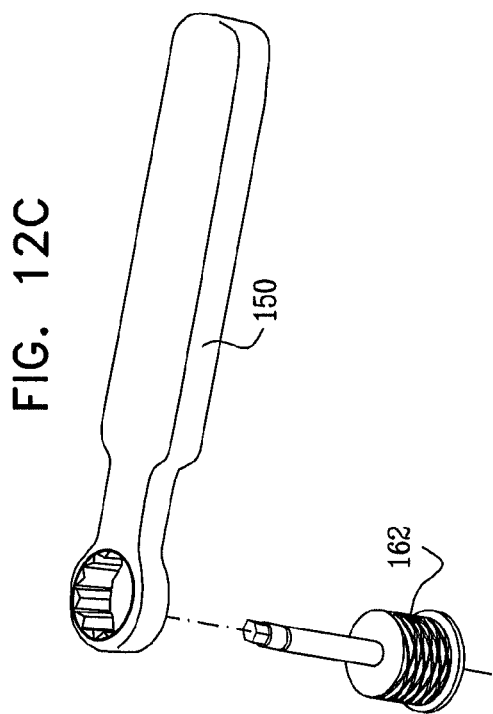
FIG. 12D
FIG. 12E
FIG. 12C

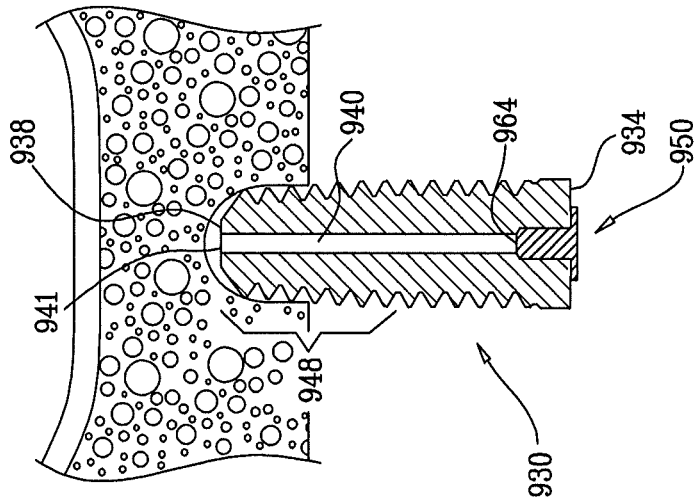
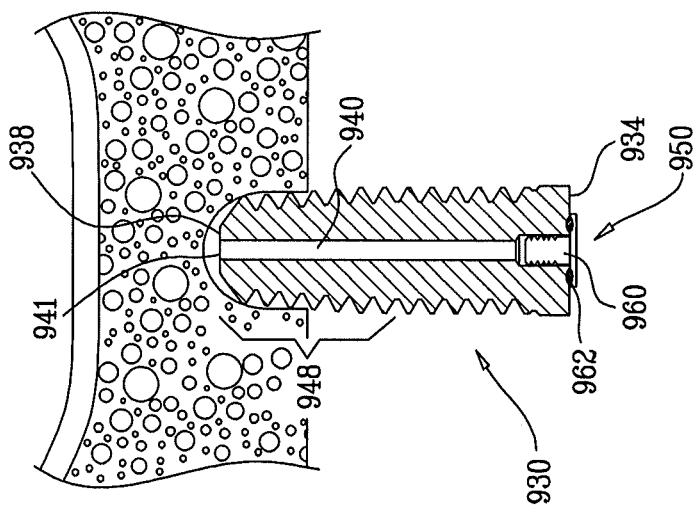

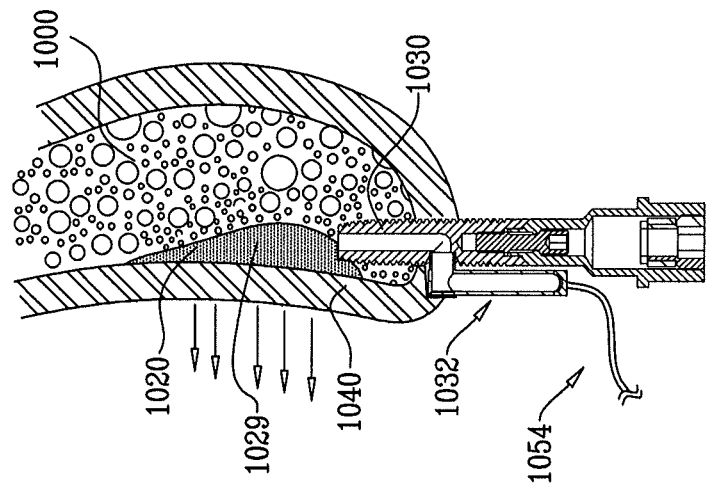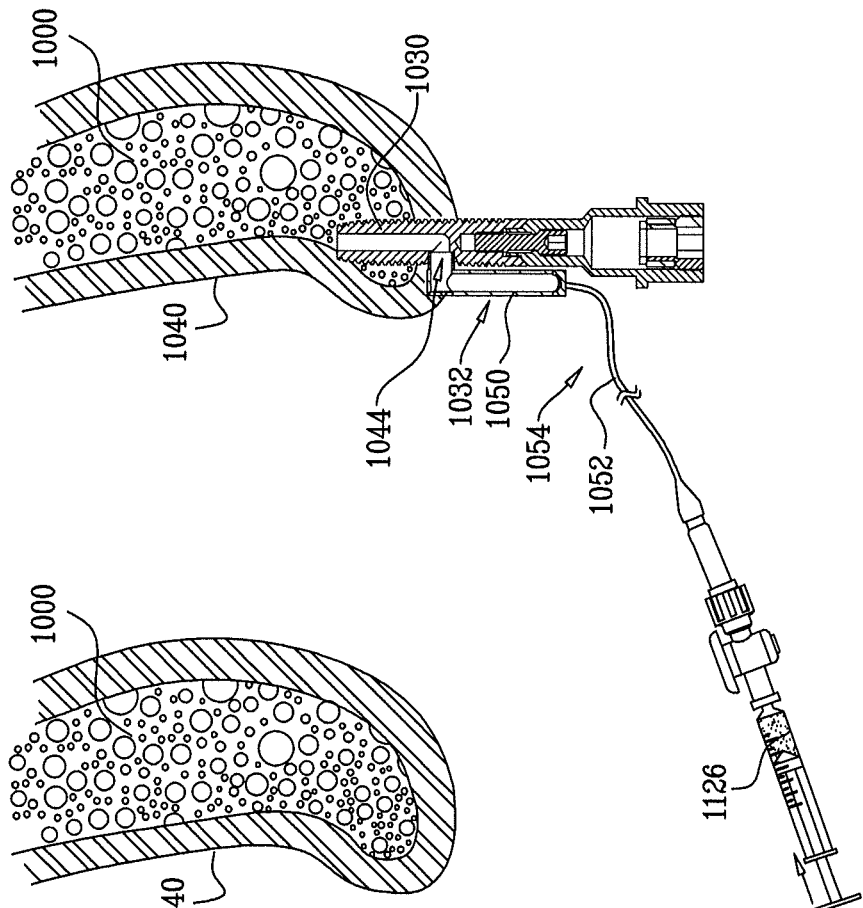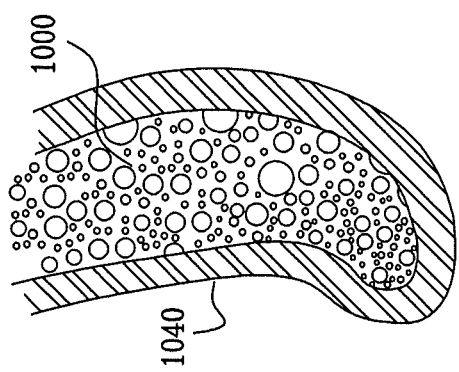

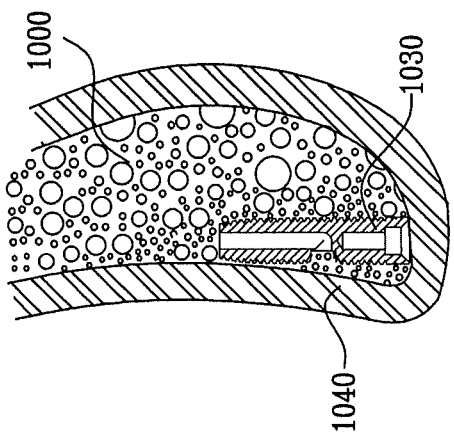
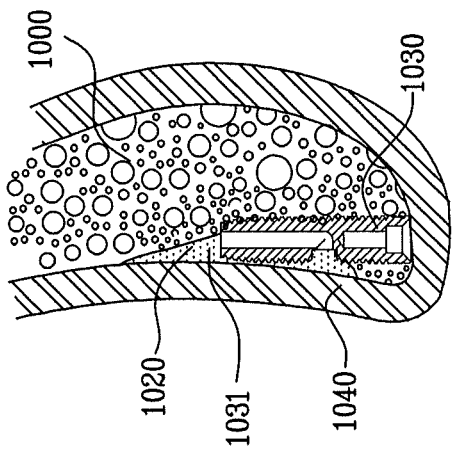
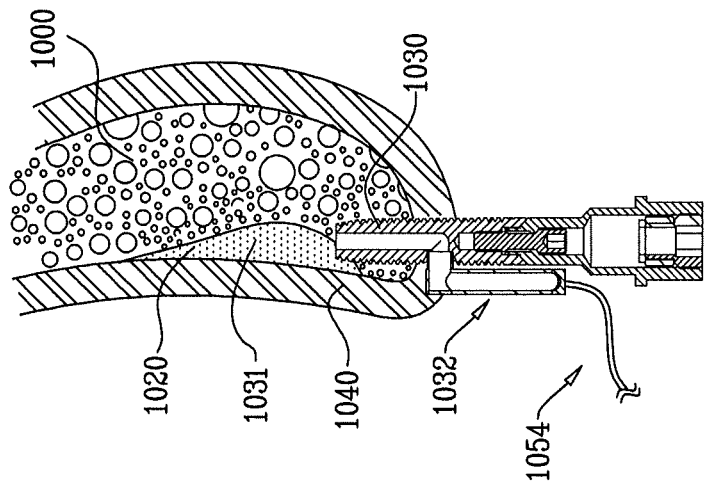

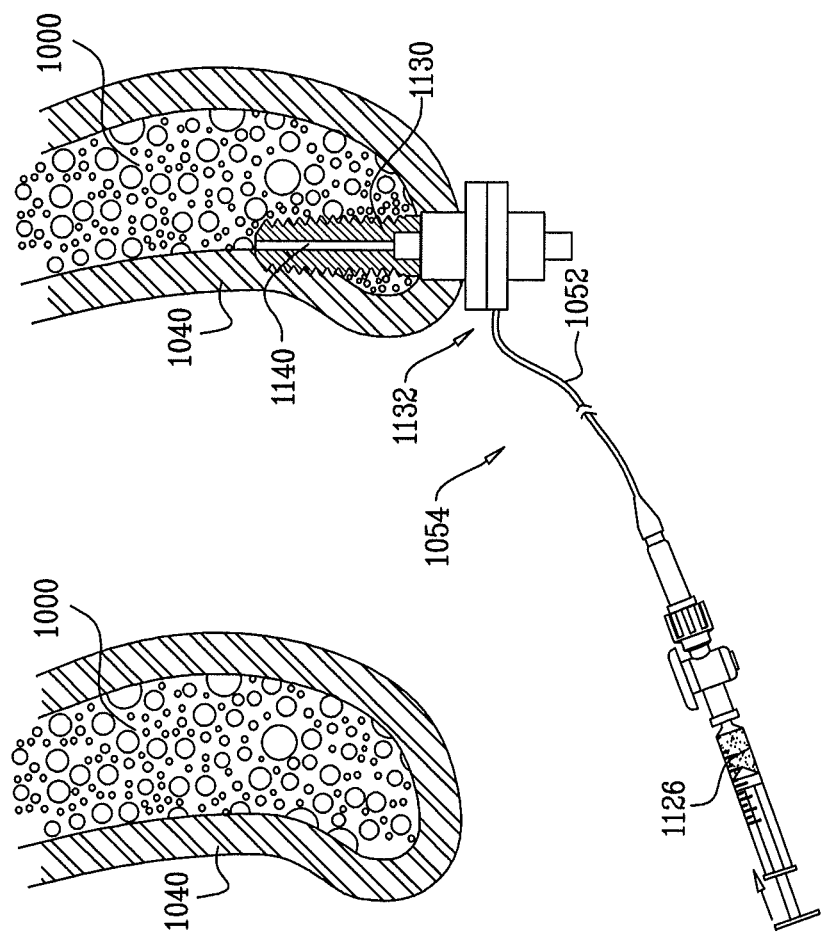

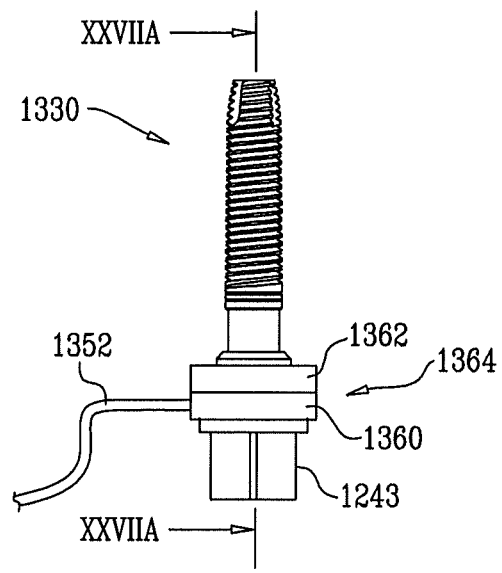
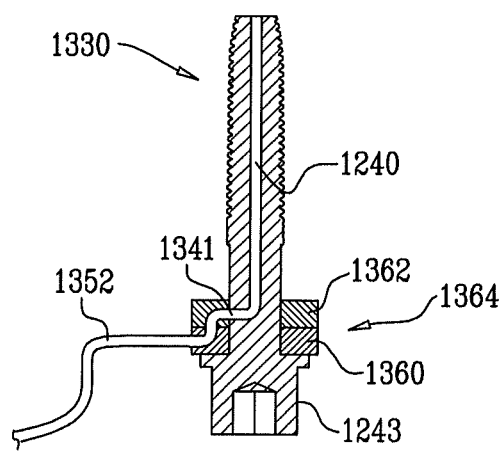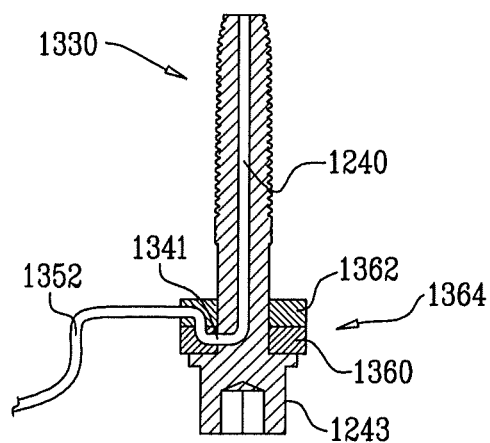

DENTAL IMPLEMENTS HAVING END MILL CUTTER SURFACES

CROSS-REFERENCE TO RELATED APPLICATIONS

The present application is a continuation of U.S. patent application Ser. No. 12/485,199, filed Jun. 16, 2009, now U.S. Pat. No. 8,029,284.

FIELD OF THE INVENTION

The present invention relates generally to dental implants and implantation methods, and specifically to minimally-invasive sinus lift implants and implantation methods.

BACKGROUND OF THE INVENTION

Osseointegrated dental implants are typically metallic or ceramic screws that are placed in the jawbone for supporting artificial teeth after the loss of natural teeth. Replacement of the maxillary teeth is often a challenging surgical procedure when the remaining maxillary bone has insufficient height to support the implant. One surgical technique for augmenting the maxillary bone includes injecting a regenerative material, such as autogenic, allogeneic, xenogeneic, or synthetic bone graft, into the vicinity of the maxillary bone. The regenerative material forms additional bone mass that integrates with the existing maxillary bone, providing the necessary alveolar height to support the implant.

Bone augmentation procedures are often surgically difficult to perform, and are associated with complications, including infection of the maxillary sinus. The top of the maxillary alveolar ridge forms the floor of the maxillary sinus, and is covered by a thin membrane known as the Schneiderian or subantral membrane. In one surgical procedure, known as a closed or internal sinus lift or elevation procedure, the surgeon drills a bore through the maxillary alveolar ridge from the oral cavity at the desired location of the implant. The bore penetrates the ridge to below the Schneiderian membrane. The surgeon injects the regenerative material through the bore to below the membrane, forming a cavity defined by the top of the ridge and the bottom of the membrane, which cavity occupies a portion of the space initially occupied by the maxillary sinus.

To prevent potentially serious complications, the surgeon must be careful not to perforate the Schneiderian membrane. This is often difficult, because of the delicacy of the membrane, and the restricted access afforded by the closed approach.

Sotirakis E, in an article entitled, "A different method for elevation of the floor of the maxillary sinus: Experimental study and reference to some cases," Mediterranean Dental Implant Congress (Athens, Greece), Scientific Programme MDIC (2004), which is incorporated herein by reference, describes a surgical procedure for elevating the antral floor using hydraulic pressure applied with a medical syringe. The procedure was first tested experimentally on hen's eggs as a surrogate sinus, and subsequently on human cadaver preparations.

Chen L et al., in an article entitled, "An 8-year retrospective study: 1,100 patients receiving 1,557 implants using the minimally invasive hydraulic sinus condensing technique," J Periodontol 76:482-491 (2005), which is incorporated herein by reference, describe an internal crestal approach for performing sinus lift and placing endosseous implants. Sinus burs and condensers of increasing width were used in conjunction with pliable atraumatic bone grafting mixture and hydraulic pressure from a surgical handpiece. The risk of membrane perforation was reduced using the surgeon's tactile skill administered in a two-stage process to first loosen and then graft bone particulate under the Schneiderian membrane. Threaded implants were placed during the same procedure, and secured via primary closure.

US Patent Application Publication 2006/0084034 to Hochman, which is incorporated herein by reference, describes techniques for providing implants in the upper jaw. A sleeve is inserted through the alveolar ridge to the maxillary sinus. The sleeve is used to raise the subantral membrane and form a cavity. A filler, such as a bone growth stimulant, is injected through the sleeve into the cavity. In the process, the sleeve also can cut and/or condense the bone around itself so that the bone can hold an implant. Optionally, the bone growth stimulant is also introduced into the bone surrounding the sleeve. During the injection, the pressure within the sleeve or the cavity is monitored to detect and prevent the rupture of the subantral membrane.

US Patent Application Publication 2006/0172255 to Hochman et al., which is incorporated herein by reference, describes a surgical tool used for preparing a surgical sinus-lift osteotomy. The tool has a defined thread geometry in series with an osteotome tip to cut, crack and push bone from the sinus floor upward into the sinus cavity in a tactual, gentle and controlled motion. The apical osteotome tip is driven into a pre-drilled pilot osteotomy after the cutting threads are engaged and rotated until the sinus floor is cracked free. Once the bony sinus floor is cracked free, a fluid passageway can be pressurized with a sterile fluid at a defined pressure to release and push the sinus membrane upward into the sinus cavity to create a desired apical cavity for grafting.

US Patent Application Publication 2007/0162024 to Siemonsmeier, which is incorporated herein by reference, describes an implant comprising at least one shaft area for anchoring in a bony structure, and at least one opening at the distal end of the shaft area in which the shaft area has a continuous bore extending from the opening to at least one outlet at the apical end, so that targeted introduction of material at least into the periapical area is possible with a stable anchoring in the bone structure even after implantation.

U.S. Pat. No. 5,711,315 to Jerusalmy, which is incorporated herein by reference, describes a method for subantral augmentation including the steps of lifting the Schneiderian membrane from the antral floor, and placing graft material between the Schneiderian membrane and the antral floor, without fracturing the lateral maxillary wall.

U.S. Pat. No. 5,575,650 to Niznick et al., which is incorporated herein by reference, describes a twist-bladed dental drill with an enhanced cutting tip for preparing surgical sites for endosseous implants. The drill includes a central, axially-extending internal passageway for carrying fluid through the shank of the drill to the outer surfaces of the drill.

U.S. Pat. No. 6,758,673 to Fromovich et al., which is incorporated herein by reference, describes techniques for gradual displacing of the periosteal tissue covering bones. The gap developing between the bone and the displaced periosteal tissue will be filled with bone callus as it is in distraction osteogenesis. The techniques allow formation of bone in distraction osteogenesis without cutting a segment of the bone.

The following references may be of interest:
U.S. Pat. No. 4,431,416 to Niznick
U.S. Pat. No. 5,261,818 to Shaw
U.S. Pat. No. 5,456,601 to Sendax
U.S. Pat. No. 5,575,650 to Niznick et al.

U.S. Pat. No. 5,685,716 to Linkow
U.S. Pat. No. 5,759,036 to Hinds
U.S. Pat. No. 5,782,918 to Klardie et al.
U.S. Pat. No. 5,795,160 to Hahn et al.
U.S. Pat. No. 5,829,977 to Rogers et al.
U.S. Pat. No. 5,839,899 to Robinson
U.S. Pat. No. 5,879,161 to Lazzara
U.S. Pat. No. 5,967,777 to Klein et al.
U.S. Pat. No. 6,068,479 to Kwan
U.S. Pat. No. 7,297,102 to Smith et al.
U.S. Pat. No. 7,364,430 to Kitamura et al.
U.S. Pat. No. 7,396,232 to Fromovich et al.
US Patent Application Publication 2003/0105469 to Karmon
US Patent Application Publication 2003/0232308 to Simmons, Jr.
U.S. Provisional Application 60/619,542 to Hochman
PCT Publication WO 07/080,595 to Levi et al.
PCT Publication WO 07/114,553 to Ahn
Riley ET et al., "The Episure syringe: a novel loss of resistance syringe for locating the epidural space," Anesth Analg. 105(4):1164-6 (October 2007)
Muronoi M et al., "Simplified procedure for augmentation of the sinus floor using a haemostatic nasal balloon," British Journal Of Oral & Maxillofacial Surgery 41(2):120-121 (2003)
Vercellotti T, "Piezoelectric surgery in implantology: a case report—a new piezoelectric ridge expansion technique," Int J Periodontics Restorative Dent 20(4):358-65 (2000)
Vercellotti T et al., "The Piezoelectric Bony Window Osteotomy and Sinus Membrane Elevation Introduction of a New Technique for Simplification of the Sinus Augmentation Procedure," Int J Periodontics Restorative Dent 21(6):561-7 (2001)
Flanagan D, "Important arterial supply of the mandible, control of an arterial hemorrhage, and report of a hemorrhagic incident," J Oral Implantol 29(4):165-73 (2003)

SUMMARY OF THE INVENTION

Some embodiments of the present invention provide a self-tapping osseointegrated dental implant and minimally-invasive closed sinus lift techniques for augmenting the maxillary alveolar ridge while reducing the risk of perforating the Schneiderian membrane and of infection. The dental implant is shaped so as to define a lumen therethrough having a distal opening through a distal external surface of a distal portion of the implant. During an implantation procedure, a surgeon simultaneously forms a bore through the maxillary alveolar ridge and advances the implant into the bore by screwing the implant into the ridge. For some applications, while the surgeon screws the implant, a fluid is provided under monitored pressure to the distal implant portion via the lumen. A drop in the pressure is detected as the distal implant end forms an opening through the top of the ridge to below the Schneiderian membrane, thereby bringing the distal opening into fluid communication with a surface of the membrane facing the ridge. Upon detection of the pressure drop, the surgeon ceases screwing the implant to avoid perforating the membrane.

The surgeon gently lifts and separates the membrane from the top of the ridge by injecting a fluid under controlled pressure via the lumen, so as to form a cavity below the membrane between the ridge and the membrane. The surgeon injects a regenerative material, such as liquid or gel bone graft, via the lumen into the cavity. Alternatively, the surgeon forms a second bore through the ridge, and injects the regenerative material into the cavity through this second bore. The surgeon further screws the implant into the regenerative material in the cavity. After bone grows into the regenerative material, a dental appliance, such as a crown, is coupled to the implant.

In some embodiments of the present invention, a proximal end of the lumen of the implant has a lateral opening through a lateral external surface of the implant, and is not open to a proximal external surface of the implant within 2 mm of the proximal-most part of the implant. The implant typically is permanently closed within 3 mm of the proximal-most part. During the implantation procedure, the additional screwing of the implant into the regenerative material advances the lateral external surface of the implant until the lateral opening is positioned entirely within the bore in the ridge and/or within the regenerative material in the cavity between the ridge and the membrane. Such positioning of both ends of the lumen within bone (current or future) substantially reduces the risk of infection, because the proximal end of the implant that is exposed to the oral cavity or gingiva is permanently closed.

In some embodiments of the present invention, a delivery tube is coupled to the lumen via the lateral opening. After injecting the regenerative material into the cavity from the delivery tube via the lumen, the surgeon decouples the delivery tube from the implant before further rotating the implant to bring the lateral opening entirely within the bore in the ridge and/or the cavity.

In some embodiments of the present invention, the distal end of the delivery tube is initially welded to the implant. A portion of the wall of the delivery tube is thinner than the wall immediately adjacent to the portion, such that application of a breaking torque to the delivery tube breaks the delivery tube at the thinner portion, thereby decoupling the delivery tube from the implant. The thinner portion is typically recessed into the lateral external surface of the implant, below the raised helical rib of screw thread. As a result, the small distal broken portion of the delivery tube that remains coupled to the implant after the delivery tube is broken does not interfere with the functioning of the screw thread.

In some embodiments of the present invention, the distal portion of the implant is shaped so as to define at least one end mill cutter surface, at least one self-tapping surface, or both the at least one end mill cutter surface and the at least one self-tapping surface. Unlike conventional end mill and self-tapping surfaces, the end mill cutter and self-tapping surfaces do not extend into a central area of the implant that defines a lumen that opens through a center of the distal end of the implant. This confining of the surfaces to the outer area of the implant accommodates the distal opening and lumen.

For some applications, the implant system comprises a swivel joint having proximal and distal joint portions, which define proximal and distal joint ports, respectively. The joint is arranged so as to define a fluid path from the proximal joint port to the distal joint port via the proximal and distal joint portions. The proximal and distal joint portions are arranged to be rotatable with respect to one another such that the fluid path is preserved during rotation. The proximal end of the delivery tube is coupled to the distal joint port, and a supply tube, which is coupled to a source of fluid, is coupled to the proximal joint port, such that the delivery tube and the supply tube are in fluid communication with one another via the swivel joint.

In some embodiments of the present invention, the implant comprises a valve arranged in a fluid path defined by the lumen, or in a fluid path defined by the delivery tube. For some applications, the valve is configured to allow passage of material through the lumen in a direction from the lateral opening toward the distal implant end, and to prevent the passage in an opposite direction. Alternatively, the valve may be configured to be bidirectional.

In some embodiments of the present invention, an applicator is removably coupled to the proximal end of the implant during a portion of an implantation procedure. The applicator comprises a chamber that is in fluid communication with the lumen, and an elastic pressure-applying element that is configured to apply pressure to the chamber. While the surgeon screws the implant into the ridge, pressure is applied by fluid in the chamber to the distal implant portion via the lumen. A drop in the pressure is detected as the distal implant end forms an opening through the top of the ridge to below a Schneiderian membrane, thereby bringing the distal opening into fluid communication with a surface of the membrane facing the ridge. Upon detection of the pressure drop, the surgeon ceases to screw the implant.

For some applications, the pressure is applied by initially inflating a balloon that defines the chamber with the fluid to greater than atmospheric pressure. Alternatively or additionally, the pressure is applied by the surgeon squeezing the chamber in conjunction with screwing the implant. For other applications, the elastic pressure-applying element comprises a piston and a spring configured to apply pressure to the chamber. For some applications, the chamber contains a fluid, and the applicator comprises an indicator element that is arranged with the piston to indicate when the pressure applied to the chamber has caused ejection of at least a portion of the fluid from the chamber out of the distal implant portion via the lumen.

For some applications, the implant comprises a plug removably coupled to the implant so as to seal the distal lumen end. The plug comes loose during the implantation procedure by friction generated by the screwing of the implant, allowing the fluid to escape from the chamber as the distal implant end forms the opening from the top of the ridge to below the membrane.

In some embodiments of the present invention, a minimally-invasive closed lateral ridge augmentation surgical procedure is provided for implanting a dental implant. The procedure is typically employed when a patient's maxillary or mandibular alveolar ridge lacks sufficient bone width to support a dental implant. A dental implement is provided that has a distal portion that extends from a distal end along up to 50% of a longitudinal length of the implement. The implement is shaped so as to define a lumen therethrough having at least one distal opening through a distal external surface of the distal portion. The surgeon forms a bore in bone of an alveolar ridge, and inserts the implement into the bore at least until the distal opening comes into fluid communication with periosteal tissue covering a lateral surface of the bone. The surgeon delaminates the periosteal tissue from the bone by injecting a fluid through the lumen to form a cavity between the bone and the periosteal tissue. After delaminating the periosteal tissue, the surgeon injects a regenerative material into the cavity via the lumen. The dental implement typically comprises the dental implant, a dental osteotome, or a dental drilling element.

There is therefore provided, in accordance with an embodiment of the present invention, apparatus including:

a dental implant having a proximal-most part, a lateral external surface, and a distal implant portion that extends from a distal implant end along up to 50% of a longitudinal length of the implant, the implant being shaped so as to define a lumen therethrough (a) having at least one distal opening through a distal external surface of the distal implant portion, (b) having a lateral opening through the lateral external surface, and (c) not open to a proximal external surface of the implant within 2 mm of the proximal-most part of the implant.

For some applications, the lumen is not open to the proximal external surface of the implant within 3 mm of the proximal-most part of the implant.

Typically, the at least one distal opening is located on the distal external surface at one or more locations selected from the group consisting of: a center of the distal implant end, a location on the distal implant end other than the center, and a location on the distal implant portion other than on the distal implant end.

Typically, the dental implant is permanently closed within 3 mm of the proximal-most part of the implant.

For some applications, the longitudinal length is less than 20 mm, and the implant has a greatest diameter of less than 10 mm.

For some applications, the lateral opening is at least 1.5 mm from the distal implant end, such as at least 2 mm from the proximal implant end, or at least 3 mm from the proximal implant end.

For some applications, at least a portion of the lateral external surface is shaped so as to define a cutting surface. For some applications, the lateral opening is within the portion of the lateral external surface that defines the cutting surface.

For some applications, at least a portion of the lateral external surface is shaped so as to define a screw thread. For some applications, the lateral opening is within the portion of the lateral external surface that defines the screw thread.

For some applications, the implant includes a valve arranged in a fluid path defined by the lumen. Typically, the valve is configured to allow passage of material through the lumen in a direction from the lateral opening toward the distal implant end, and to prevent the passage in an opposite direction.

In an embodiment, the apparatus further includes a delivery tube having a proximal tube end and a distal tube end, which distal tube end is removably coupled to the implant such that the delivery tube is in fluid communication with the lumen via the lateral opening when the delivery tube is coupled to the implant. For some applications, the delivery tube includes a valve arranged in a fluid path defined by the delivery tube. For some applications, the apparatus further includes a swivel joint having distal and proximal joint portions defining distal and proximal joint ports, respectively, the swivel joint arranged so as to define a fluid path from the proximal joint port to the distal joint port via the proximal and distal joint portions, which are arranged to be rotatable with respect to one another such that the fluid path is preserved during rotation, and the proximal tube end is coupled to the distal joint port. For some applications, the apparatus further includes an applicator, which is removably coupled to a proximal implant end of the implant, and the swivel joint defines a bore therethrough, in which at least a portion of the applicator is positioned.

There is further provided, in accordance with an embodiment of the present invention, a method including:

providing a dental implant having a proximal-most part, a lateral external surface, and a distal implant portion that extends from a distal implant end along up to 50% of a longitudinal length of the implant, the implant shaped so as to define a lumen therethrough (a) having at least one distal opening through a distal external surface of the distal implant portion, (b) having a lateral opening through the lateral external surface, and (c) not open to a proximal external surface of the implant within 2 mm of the proximal-most part of the implant;

forming a bore through a maxillary alveolar ridge;

inserting the implant into the bore at least until the distal opening comes into fluid communication with a surface of a Schneiderian membrane facing the ridge; and raising the membrane to form a cavity between the ridge and the membrane.

Typically, forming the bore includes forming at least a portion of the bore by inserting the implant into the ridge and rotating the implant. For some applications, forming the bore includes forming a preparatory portion of the bore using a dental drill, and subsequently forming the at least a portion of the bore by inserting the implant into the ridge and rotating the implant.

In an embodiment, the method further includes: after raising the membrane, injecting a regenerative material into the cavity via the lumen; and, after injecting the material, further rotating the implant until the lateral opening is positioned entirely within at least one location selected from the group consisting of: the bore in the ridge, and the cavity between the ridge and the membrane. For some applications, injecting includes injecting the regenerative material via the lumen from a delivery tube removably coupled to the implant such that the delivery tube is in fluid communication with the lumen via the lateral opening when the delivery tube is coupled to the implant, and the method further includes, after injecting the material and before the lateral opening is positioned entirely within the at least one location, decoupling the delivery tube from the implant. For some applications, raising the membrane includes injecting a fluid through the bore, and measuring a volume of the injected fluid, and injecting the regenerative material includes determining an amount of the regenerative material to inject into the cavity responsively to the measured volume of the fluid.

There is still further provided, in accordance with an embodiment of the present invention, a method including:

providing a dental implant having a proximal-most part, a lateral external surface, and a distal implant portion that extends from a distal implant end along up to 50% of a longitudinal length of the implant, the implant shaped so as to define a lumen therethrough having at least one distal opening through a distal external surface of the distal implant portion, having a lateral opening through the lateral external surface, and not open to a proximal external surface of the implant within 2 mm of the proximal-most part of the implant;

forming a bore through a maxillary alveolar ridge;

inserting the implant into the bore at least until the distal opening comes into fluid communication with a surface of a nasal floor membrane facing the ridge; and raising the membrane to form a cavity between the ridge and the membrane.

There is additionally provided, in accordance with an embodiment of the present invention, apparatus including:

a dental implant having a proximal implant end, a lateral external surface, and a distal implant portion that extends from a distal implant end along up to 50% of a longitudinal length of the implant, wherein the lateral external surface is indented so as to define a channel along the lateral external surface between (a) a first location on the distal implant portion on the lateral external surface and (b) a second location on the lateral external surface between the first location and the proximal implant end, not inclusive; and a delivery tube, a distal portion of which is positioned within the channel.

For some applications, the second location is at least 2 mm from the proximal implant end.

For some applications, at least a portion of the lateral external surface is shaped so as to define a screw thread including a raised helical rib going around the implant, and the channel crosses the rib at a plurality of sites on the lateral external surface.

For some applications, the apparatus further includes a swivel joint having distal and proximal joint portions defining distal and proximal joint ports, respectively, the swivel joint arranged so as to define a fluid path from the proximal joint port to the distal joint port via the proximal and distal joint portions, which are arranged to be rotatable with respect to one another such that the fluid path is preserved during rotation, and a proximal end of the delivery tube is coupled to the distal joint port.

For some applications, the longitudinal length is less than 20 mm, and the implant has a greatest diameter of less than 10 mm.

There is yet additionally provided, in accordance with an embodiment of the present invention, a method including:

providing (i) a dental implant having a proximal implant end, a lateral external surface, and a distal implant portion that extends from a distal implant end along up to 50% of a longitudinal length of the implant, wherein the lateral external surface is indented so as to define a channel along the lateral external surface between (a) a first location of the distal implant portion on the lateral external surface and (b) a second location on the lateral external surface between the first location and the proximal implant end, not inclusive, and (ii) a delivery tube, a distal portion of which is positioned within the channel;

forming a bore through a maxillary alveolar ridge;

inserting the implant into the bore at least until the first location comes into fluid communication with a surface of a Schneiderian membrane facing the ridge; and raising the membrane to form a cavity between the ridge and the membrane.

Typically, forming the bore includes forming at least a portion of the bore by inserting the implant into the ridge and rotating the implant. For some applications, forming the bore includes forming a preparatory portion of the bore using a dental drill, and subsequently forming the at least a portion of the bore by inserting the implant into the ridge and rotating the implant.

In an embodiment, the method further includes: after raising the membrane, injecting a regenerative material into the cavity via a delivery tube, a distal portion of which is positioned within the channel; and, after injecting the material, further rotating the implant until the second location is positioned entirely within at least one location selected from the group consisting of: the bore in the ridge, and the cavity between the ridge and the membrane. For some applications, the method further includes, after injecting the material and before the second location is positioned entirely within the at least one location, removing the delivery tube from the channel. For some applications, raising the membrane includes injecting a fluid through the bore, and measuring a volume of the injected fluid, and injecting the regenerative material includes determining an amount of the regenerative material to inject into the cavity responsively to the measured volume of the fluid.

There is also provided, in accordance with an embodiment of the present invention, a method including:

providing a dental implant having a lateral external surface and a distal implant portion that extends from a distal implant end along up to 50% of a longitudinal length of the implant, the implant shaped so as to define a lumen therethrough having at least one distal opening through a distal external surface of the distal implant portion;

forming a bore through an alveolar ridge by inserting the implant into the ridge and rotating the implant;

while forming the bore, providing a fluid under pressure to the distal implant portion via the lumen, and monitoring the pressure of the fluid; and detecting a drop in the pressure as the distal opening comes into fluid communication with the area beyond the ridge.

For some applications, the alveolar ridge is a maxillary alveolar ridge, forming the bore includes forming the bore through the maxillary alveolar ridge, and detecting includes detecting the drop in the pressure as the distal opening comes into the fluid communication with a surface of a Schneiderian membrane facing the ridge.

For some applications, the alveolar ridge is a mandibular alveolar ridge, forming the bore includes forming the bore through the mandibular alveolar ridge, and detecting includes detecting the drop in the pressure as the distal opening comes into fluid communication with an area beyond the mandibular alveolar ridge.

For some applications, the alveolar ridge is a maxillary alveolar ridge, forming the bore includes forming the bore through the maxillary alveolar ridge, and detecting includes detecting the drop in the pressure as the distal opening comes into the fluid communication with a surface of a nasal floor membrane facing the ridge.

Typically, rotating the implant includes ceasing to rotate the implant responsively to detecting the pressure drop.

For some applications, providing the implant includes providing the implant shaped such that the lumen is open to the lateral external surface and not open to a proximal external surface of the implant within 2 mm of a proximal-most part of the implant.

There is further provided, in accordance with an embodiment of the present invention, a method including:

providing a dental implement having (a) a distal portion that extends from a distal end along up to 6 mm of a longitudinal length of the bit, and (b) a lateral external surface that is shaped so as to define a cutting surface at least in a vicinity of the distal end, the implement shaped so as to define a lumen therethrough having at least one distal opening through a distal external surface of the distal portion;

forming a bore through a bone by inserting the implement into the bone and rotating the implement;

while forming the bore, providing a fluid under pressure to the distal portion via the lumen, and monitoring the pressure of the fluid; and detecting a drop in the pressure as the distal opening comes into fluid communication with an area beyond the bone.

In an embodiment, wherein providing the dental implement comprises providing a dental drill bit.

In an embodiment, providing the dental implement comprises providing a dental osteotome For some applications, the distal portion extends from the distal end along up to 4 mm of the longitudinal length of the implement, such as along up to 2 mm of the longitudinal length of the implement.

For some applications, the bone is a maxillary alveolar ridge, forming the bore includes forming the bore through the maxillary alveolar ridge, and detecting includes detecting the drop in the pressure as the distal opening comes into the fluid communication with a surface of a Schneiderian membrane facing the ridge.

For some applications, the bone is a mandibular alveolar ridge, forming the bore includes forming the bore through the mandibular alveolar ridge, and detecting includes detecting the drop in the pressure as the distal opening comes into the fluid communication with the area beyond the mandibular alveolar ridge.

For some applications, the bone is a maxillary alveolar ridge, forming the bore includes forming the bore through the maxillary alveolar ridge, and detecting includes detecting the drop in the pressure as the distal opening comes into the fluid communication with a surface of a nasal floor membrane facing the ridge.

For some applications, the bone is an alveolar ridge, forming the bore includes forming a first bore with an inclined entry at a first location on the ridge, and the method further includes: injecting a regenerative material through the first bore; forming a second bore at a second location on the ridge; and inserting a dental implant into the second bore.

For some applications, the bone is a palate, wherein forming the bore includes forming a first bore at a first location on the palate, and the method further includes: injecting a regenerative material through the first bore; forming a second bore at a second location on a maxillary alveolar ridge; and inserting a dental implant into the second bore.

Typically, rotating the implement includes ceasing to rotate the bit responsively to detecting the pressure drop.

There is still further provided, apparatus including:

a dental implant having a distal implant portion that extends from a distal implant end along up to 50% of a longitudinal length of the implant, the implant shaped so as to define a lumen through the implant, which lumen has at least one distal opening through a distal external surface of the distal implant portion; and a swivel joint having first and second joint portions defining first and second joint ports, respectively, the swivel joint arranged so as to define a fluid path from the second joint port to the first joint port via the second and first joint portions, which are arranged to be rotatable with respect to one another such that the fluid path is preserved during rotation, wherein the fluid path through the swivel joint is in fluid communication with the lumen via the first joint port.

In an embodiment, the first joint portion is positioned distal to the second joint portion. For some applications, the implant is shaped such that the lumen has a lateral opening through a lateral external surface of the dental implant, and the apparatus further includes a delivery tube having (a) a proximal tube end that is coupled to the first joint port, and (b) a distal tube end that is removably coupled to the implant such that the delivery tube is in fluid communication with the lumen via the lateral opening when the delivery tube is coupled to the implant.

In an embodiment, the first joint portion is positioned proximal to the second joint portion.

For some applications, the apparatus further includes an applicator, which is removably coupled to a proximal implant end of the dental implant, and the swivel joint defines a bore therethrough, in which at least a portion of the applicator is positioned.

For some applications, the implant is shaped such that the lumen is open to a proximal end of the dental implant through a proximal opening of the implant.

For some applications, the first joint port is positioned on a surface of the first joint portion facing the dental implant, and a proximal end of the lumen has a lateral opening through a lateral external surface of the implant, which lateral opening is in fluid communication with the first joint port.

For some applications, the longitudinal length is less than 20 mm, and the implant has a greatest diameter of less than 10 mm.

There is additionally provided, in accordance with an embodiment of the present invention, apparatus including:

a dental implant having a distal implant portion that extends from a distal implant end along up to 50% of a longitudinal length of the implant, the implant being shaped so as to define a lumen therethrough having a proximal opening and a distal opening through a distal external surface of the distal implant portion, and the implant including a valve arranged in a fluid path defined by the lumen.

For some applications, the valve is configured to allow passage of material through the lumen in a direction from the proximal opening toward the distal opening, and to prevent the passage in an opposite direction.

For some applications, the longitudinal length is less than 20 mm, and the implant has a greatest diameter of less than 10 mm.

For some applications, the implant is shaped such that the proximal opening is through a lateral external surface of the implant, and the apparatus further includes a delivery tube removably coupled to the implant such that the delivery tube is in fluid communication with the lumen via the proximal opening when the delivery tube is coupled to the implant. For some applications, the valve is configured to allow bidirectional flow through the lumen when the valve is in an open position, and to block the flow when the valve is in a closed position. For some applications, the valve is configured to assume the open position by being pushed open by the delivery tube when the delivery tube is coupled to the implant, and to assume the closed position when the delivery tube is not coupled to the implant. For some applications, the valve includes an opening/closing control element that is accessible from outside of the implant.

There is still additionally provided, in accordance with an embodiment of the present invention, a method including:

providing a dental implant having a distal implant portion that extends from a distal implant end along up to 50% of a longitudinal length of the implant, the implant shaped so as to define a lumen therethrough having a proximal opening and a distal opening through a distal external surface of the distal implant portion, and the implant including a valve arranged in a fluid path defined by the lumen; and forming a bore through a portion of a maxillary alveolar ridge by inserting the implant into the ridge and rotating the implant at least until the distal opening comes into fluid communication with a surface of a Schneiderian membrane facing the ridge.

For some applications, the valve is configured to allow passage of material through the lumen in a direction from the proximal opening toward the distal opening, and to prevent the passage in an opposite direction.

For some applications, the implant is shaped such that the proximal opening is through a lateral external surface of the implant, and the method further includes:

after the distal opening comes into the fluid communication with the surface of the membrane, injecting a regenerative material into the cavity via the lumen from a delivery tube removably coupled to the implant such that the delivery tube is in fluid communication with the lumen via the proximal opening when the delivery tube is coupled to the implant;

after injecting the material, decoupling the delivery tube from the implant; and after injecting the material, further rotating the implant to further advance the distal implant end.

There is also provided, in accordance with an embodiment of the present invention, apparatus including:

a dental implant having a proximal implant end, a distal implant end, and a lateral external surface; and a removable sheath covering at least a portion of the lateral external surface, such that at least a portion of the distal implant end is exposed.

For some applications, the implant is shaped so as to define a lumen therethrough having at least one distal opening through a distal external surface of a distal implant portion that extends from the distal implant end along up to 50% of a longitudinal of the implant.

For some applications, the implant has a longitudinal length of less than 20 mm and a greatest diameter of less than 10 mm.

There is further provided, in accordance with an embodiment of the present invention, a method including:

providing (a) a dental implant having a proximal implant end, a distal implant end, and a lateral external surface, and (b) a removable sheath covering at least a portion of the lateral external surface, such that at least a portion of the distal implant end is exposed;

inserting the implant into an alveolar ridge; and inhibiting infection, by removing the sheath from the implant in conjunction with the inserting.

There is still further provided, in accordance with an embodiment of the present invention, apparatus including:

a dental implant having a distal implant portion that extends from a distal implant end along up to 50% of a longitudinal length of the implant, the implant shaped so as to define a lumen therethrough having at least one distal opening through a distal external surface of the distal implant portion; and an applicator, which is removably coupled to the proximal implant end, and which includes a chamber that is in fluid communication with the lumen, and an elastic pressure-applying element that is configured to apply pressure to the chamber.

For some applications, the applicator is sized to be positioned entirely within an oral cavity.

For some applications, the elastic pressure-applying element includes a balloon shaped so as to define the chamber.

For some applications, the apparatus further includes a fluid with which the chamber is filled at a pressure greater than atmospheric pressure.

For some applications, the lumen has a proximal opening through a proximal external surface of a proximal implant end of the implant.

For some applications, the longitudinal length is less than 20 mm, and the implant has a greatest diameter of less than 10 mm.

For some applications, the apparatus further includes a plug removably coupled to the implant so as to seal the distal opening. For some applications, the plug is removable from the implant by friction generated during screwing of the dental implant. For some applications, the plug includes a biodegradable material. For some applications, the plug includes a regenerative material.

In an embodiment, the lumen has a proximal opening through a lateral external surface of the implant, and the lumen is not open to a proximal external surface of the implant within 2 mm of a proximal-most part of the implant. For some applications, the apparatus further includes a delivery tube having (a) a proximal tube end that is in fluid communication with the chamber, and (b) a distal tube end that is removably coupled to the implant such that the chamber is in fluid communication with the lumen via the delivery tube via the proximal opening when the delivery tube is coupled to the implant.

In an embodiment, the elastic pressure applying element includes a piston and a spring configured to apply pressure to the chamber. For some applications, the chamber contains a fluid, and the applicator includes an indicator element that is arranged with the piston to indicate when the pressure applied to the chamber has caused ejection of at least a portion of the fluid from the chamber out of the distal opening via the lumen.

There is additionally provided, in accordance with an embodiment of the present invention, a method including:

providing (a) a dental implant having a distal implant portion that extends from a distal implant end along up to 50% of longitudinal length of the implant, the implant shaped so as to define a lumen therethrough having at least one distal opening through a distal external surface of the distal implant portion, (b) an applicator, which is removably coupled to the proximal implant end, and which includes a chamber that is in fluid communication with the lumen, and (c) a fluid contained within the chamber;

forming a bore through a portion of a maxillary alveolar ridge by inserting the applicator into an oral cavity of the subject, inserting the implant into the ridge, and rotating the implant;

while forming the bore, applying pressure by the fluid to the distal implant portion via the lumen, and monitoring the pressure of the fluid; and detecting a drop in the pressure as the distal opening comes into fluid communication with a surface of a Schneiderian membrane facing the ridge.

For some applications, inserting the applicator into the oral cavity includes inserting the entire applicator, including the entire chamber, into the oral cavity.

For some applications, applying the pressure includes squeezing the chamber in conjunction with rotating the implant.

Typically, the method further includes ceasing to rotate the implant responsively to detecting the pressure drop.

For some applications, applying the pressure includes providing a balloon shaped so as to define the chamber. For some applications, applying the pressure includes initially inflating the balloon with the fluid to greater than atmospheric pressure.

There is still additionally provided, in accordance with an embodiment of the present invention, a method including:

providing a plurality of dental implants having respective lateral external surfaces and respective distal implant portions that extend from respective distal implant ends along up to 50% of respective longitudinal lengths of the implants, the implants shaped so as to define respective lumens therethrough having respective distal openings through respective distal external surfaces of the distal implant portions;

forming a respective plurality of bores through respective portions of a maxillary alveolar ridge by, for each of the bores, inserting one of the implants into the ridge and rotating the implant; and after forming the bores, lifting a Schneiderian membrane by injecting a material under the Schneiderian membrane through each of the implants in turn.

For some applications, forming each of the bores using a respective one of the implants includes:

while forming the bore, providing a fluid under pressure to the distal implant portion via the lumen, and monitoring the pressure of the fluid;

detecting a drop in the pressure as the distal opening comes into fluid communication with a surface of the Schneiderian membrane facing the ridge; and ceasing to rotate the implant responsively to detecting the pressure drop.

There is also provided, in accordance with an embodiment of the present invention, apparatus including a dental sleeve, which is configured to be inserted into a bore formed through a portion of a maxillary alveolar ridge, and which includes:

a tubular portion having proximal and distal ends, and shaped so as to define a lumen therethrough; and a biodegradable valve coupled to the distal end of the tubular portion, and configured to allow flow through the lumen in a direction from the proximal end to the distal end, and to prevent flow in an opposite direction.

For some applications, the valve includes a duckbill check valve.

For some applications, the tubular portion is biodegradable.

For some applications, the tubular portion and valve are configured to be readily separated from one another.

For some applications, the dental sleeve has a longitudinal length of less than 20 mm and a greatest diameter of less than 10 mm.

There is further provided, in accordance with an embodiment of the present invention, a method including:

forming a bore through a maxillary alveolar ridge;

lifting a Schneiderian membrane via the bore to form a cavity between the ridge and the membrane;

after lifting the membrane, inserting into the bore a dental sleeve including (a) a tubular portion having proximal and distal ends, and shaped so as to define a lumen therethrough, and (b) a biodegradable valve coupled to the distal end of the tubular portion, and configured to allow flow through the lumen in a direction from the proximal end to the distal end, and to prevent the flow in an opposite direction;

after inserting the sleeve, injecting a regenerative material through the lumen and valve into the cavity; and after inserting the sleeve, leaving the valve in place to biodegrade.

In an embodiment, the method further includes mounting a dental implant in the bore by rotating the implant at least until a distal portion thereof breaks through the valve into the cavity between the ridge and the membrane.

For some applications, the tubular portion is biodegradable, and leaving the valve in place further includes leaving the tubular portion in place.

For some applications, leaving the valve in place includes separating the tubular portion from the valve, withdrawing the tubular portion from the bore, and leaving the valve in place to biodegrade.

For some applications, the valve includes a duckbill check valve.

There is still further provided, in accordance with an embodiment of the present invention, apparatus for use with a subject, the apparatus including:

a dental drilling element having a distal end;

a light source, which is configured to emit light into a body cavity of the subject;

a light sensor, which is configured to sense a level of illumination at the distal end of the drilling element; and an output unit, which is configured to generate an output responsively to the level of the illumination.

For some applications, the light source is configured to be placed at least partially within the body cavity. Alternatively, the light source is configured to be placed outside of the body cavity.

For some applications, the light source is configured to emit the light from the distal end of the drilling element.

There is additionally provided, in accordance with an embodiment of the present invention, apparatus for use with a subject, the apparatus including:

a dental drilling element having a distal end;

a light source, which is configured to emit light from the distal end of the drilling element;

a light sensor, which is configured to sense a level of illumination within a body cavity of the subject; and an output unit, which is configured to generate an output responsively to the level of the illumination.

For some applications, the light sensor is configured to be placed at least partially within the body cavity. Alternatively, the light sensor is configured to be placed outside of the body cavity.

There is yet additionally provided, in accordance with an embodiment of the present invention, a method including:

forming a bore in a maxillary alveolar ridge of a subject by inserting a dental drilling element into the ridge and rotating the drilling element;

emitting light into a body cavity of the subject;

sensing a level of illumination at a distal end of the drilling element; and generating an output responsively to the level of the illumination.

For some applications, the method further includes ceasing to rotate the drilling element responsively to ascertaining that the level of illumination passes a threshold level.

For some applications, emitting the light includes placing a light source at least partially within the body cavity, and emitting the light from the light source. Alternatively, emitting the light includes emitting the light at a location outside of the body cavity in a vicinity thereof.

For some applications, emitting the light includes emitting the light from the distal end of the drilling element.

There is also provided, in accordance with an embodiment of the present invention, a method including:

forming a bore in a maxillary alveolar ridge of a subject by inserting a dental drilling element into the ridge and rotating the drilling element;

emitting light from a distal end of the drilling element;

sensing a level of illumination within a body cavity of the subject; and generating an output responsively to the level of the illumination.

For some applications, the method further includes ceasing to rotate the drilling element responsively to ascertaining that the level of illumination passes a threshold level.

For some applications, sensing includes sensing the level of illumination by placing a light sensor at least partially within the body cavity and sensing using the light sensor. Alternatively, sensing includes sensing the level of illumination within the body cavity from outside the body cavity in a vicinity thereof.

There is further provided, in accordance with an embodiment of the present invention, a regenerative composition including:

a physiological solution; and solid bone graft particles mixed with the physiological solution at a volume concentration of less than 50%.

For some applications, the volume concentration of the particles is less than 25%.

For some applications, the particles include freeze-dried bone allograft (FDBA).

For some applications, the physiological solution is selected from the group consisting of: saline solution, blood, and diluted blood.

There is still further provided, in accordance with an embodiment of the present invention a method including:

forming at least one bore through a bone from a first side of the bone to a second side of the bone;

raising a membrane on the second side of the bone to form a cavity between the second side of the bone and the membrane; and injecting into the cavity via the bore a composition including saline solution and solid bone graft particles mixed with the saline solution at a volume concentration of less than 50%.

For some applications, forming the bore includes forming the bore through a maxillary alveolar ridge, and raising the membrane includes raising a Schneiderian membrane.

For some applications, forming the at least one bore includes forming first and second bores through the bone, and injecting includes injecting the composition into the cavity via the first bore, such that at least a portion of the saline solution drains from the cavity via the second bore, leaving at least a portion of the solid bone graft particles in the cavity.

For some applications, the volume concentration of the particles is less than 25%.

For some applications, the particles include freeze-dried bone allograft (FDBA).

For some applications, the physiological solution is selected from the group consisting of: saline solution, blood, and diluted blood.

There is additionally provided, in accordance with an embodiment of the present invention, apparatus including:

a dental implant having a proximal implant end and a lateral external surface, the implant being shaped so as to define a lumen therethrough having a lateral opening through the lateral external surface; and an applicator, which is removably coupled to the proximal implant end, and which includes a delivery tube having a distal tube end that is removably coupled to the implant such that the delivery tube is in fluid communication with the lumen via the lateral opening.

In an embodiment, the distal tube end is welded to the implant, and a portion of a wall of the delivery tube is thinner than the wall immediately adjacent to the portion, such that application of a breaking torque to the delivery tube breaks the delivery tube at the thinner portion, thereby decoupling the delivery tube from the implant, and the thinner portion is within 3 mm of the distal tube end. For some applications, the delivery tube is shaped so as to be circumscribed with a groove that defines the thinner portion.

For some applications, the thinner portion has a width of less than 0.1 mm. Typically, the portion of the delivery tube is sufficiently thin such that the application of the breaking torque of less than 50 Newton centimeters breaks the delivery tube at the thinner portion.

Typically, at least a portion of the lateral external surface that includes the lateral opening is shaped so as to define a screw thread including a raised helical rib going around the implant, and the thinner portion is recessed into the lateral external surface below the raised helical rib.

In an embodiment, the applicator is configured to break the delivery tube at the thinner portion by rotating the distal tube end with respect to the lateral opening. Typically, the applicator is configured to apply a torque of greater than 50 Newton centimeters to the delivery tube, when rotating the distal tube end with respect to the lateral opening.

For some applications, the applicator includes a lever arm, which is coupled to the delivery tube and arranged to rotate the distal tube end with respect to the lateral opening. For some applications, the delivery tube is shaped so as to define a bend at between 5 and 20 mm from the distal tube end, the bend having an angle of between 85 and 180 degrees, and the lever arm is coupled to the delivery tube at a location proximal to the bend. For some applications, the applicator includes a rotatable surface accessible from a proximal end of the applicator, which rotatable surface is rotatable with respect to a portion of the applicator, rotation of which rotatable surface rotates the distal tube end by extending the lever arm.

In an embodiment, the applicator includes: a connecting screw, which removably couples the applicator to the proximal implant end; and a rotatable surface accessible from a proximal end of the applicator, which rotatable surface is rotatable with respect to a portion of the applicator, and the applicator is configured such that rotation of the rotatable surface both (a) applies the breaking torque to the delivery tube that breaks the delivery tube at the thinner portion, and (b) rotates the screw to decouple the applicator from the proximal implant end.

In an embodiment, when the delivery tube is coupled to the implant, a portion of the delivery tube runs alongside the implant such that a greatest distance between a longitudinal axis of the implant and a surface of the portion of the delivery tube furthest from the longitudinal axis is less than 6 mm, such as less than 5 mm.

In an embodiment, the applicator includes an applicator body, which includes a rotatable surface accessible from a proximal end of the applicator, rotation of which rotatable surface with respect to a portion of the applicator body causes the delivery tube to become decoupled from the implant, and the applicator is shaped so as to define a stabilization surface accessible from the proximal end of the applicator, application to which stabilization surface of a stabilizing force stabilizes the implant during rotation of the rotatable surface. For some applications, the rotatable surface and the stabilization surface are configured to facilitate on-axis rotation of the rotatable surface, thereby minimizing any off-axis force that the rotation may cause the apparatus to apply to its surroundings.

For some applications, the apparatus further includes a stabilization tool, which is configured to be removably coupled to the stabilization surface of the applicator body, and to apply the stabilizing force to the stabilization surface. For some applications, the stabilization tool defines an opening, and the apparatus further includes a driver tool, which is configured to be removably coupled to the rotatable surface through the opening of the stabilization tool, and to rotate the rotatable surface. For some applications, the driver tool is permanently coupled to the stabilization tool.

Typically, the delivery tube includes a rigid material.

For some applications, the delivery tube has a proximal tube end, and the apparatus further includes a flexible supply tube coupled to the proximal tube end.

For some applications, the delivery tube is shaped so as to define a bend within 10 mm of the distal tube end, the bend having an angle of between 85 and 95 degrees.

In an embodiment, the applicator further includes a retaining element, which is configured to assume a first position in which the retaining element prevents the distal tube end from separating from the implant, and a second position in which the retaining element does not prevent the distal tube end from separating from the implant. For some applications, the distal tube end is shaped so as to define a cone. For some applications, the cone has an opening angle of between 0 and 60 degrees. Alternatively or additionally, the cone is shaped so as to define a Morse taper.

For some applications, the delivery tube is configured to pivot with respect to the applicator.

For some applications, the applicator further includes a spring, which is configured to apply a force that separates the distal tube end from the implant when the retaining element assumes the second position. For some applications, the applicator includes a sealing element, which is configured to removably sealingly couple the delivery tube to the implant.

For some applications, the applicator includes a sealing element, which is configured to removably sealingly couple the delivery tube to the implant.

For some applications, the lateral opening is at least 3 mm from the proximal implant end.

For some applications, the implant has a distal implant portion that extends from a distal implant end along up to 50% of a longitudinal length of the implant, and the lumen is shaped so as to define at least one distal opening through a distal external surface of the distal implant portion. For some applications, the at least one distal opening is located on the distal external surface at one or more locations selected from the group consisting of: a center of the distal implant end, a location on the distal implant end other than the center, and a location on the distal implant portion other than on the distal implant end. For some applications, the implant has a proximal-most part, and the lumen is not open to a proximal external surface of the implant within 2 mm of the proximal-most part of the implant. For some applications, the dental implant is permanently closed within 3 mm of the proximal-most part of the implant.

Typically, at least a portion of the lateral external surface is shaped so as to define a cutting surface. For some applications, the lateral opening is within the portion of the lateral external surface that defines the cutting surface.

There is yet additionally provided, a method including:
providing (a) a dental implant having a proximal implant end and a lateral external surface, the implant being shaped so as to define a lumen therethrough having a lateral opening through the lateral external surface, and (b) an applicator, which is removably coupled to the proximal implant end, and which includes a delivery tube having a distal tube end that is removably coupled to the implant such that the delivery tube is in fluid communication with the lumen via the lateral opening;
forming a bore in an alveolar ridge;
inserting the implant into the bore;
injecting a fluid through the lumen; and
decoupling the delivery tube from the implant.

In an embodiment, the distal tube end is initially welded to the implant, a portion of a wall of the delivery tube is thinner than the wall immediately adjacent to the portion, the thinner portion is within 3 mm of the distal tube end, and decoupling the delivery tube from the implant includes breaking the delivery tube at the thinner portion by applying a breaking torque to the delivery tube. Typically, applying the breaking torque includes applying a breaking torque of less than 50 Newton centimeters.

For some applications, breaking the delivery tube at the thinner portion includes using the applicator to break the delivery tube at the thinner portion by rotating the distal tube end with respect to the lateral opening.

In an embodiment, the applicator includes an applicator body, which includes a rotatable surface accessible from a proximal end of the applicator; decoupling the delivery tube from the implant includes rotating the rotatable surface with respect to a portion of the applicator body; the applicator is shaped so as to define a stabilization surface accessible from the proximal end of the applicator; and rotating the rotatable surface includes stabilizing the implant by applying a stabilizing force to the stabilization surface. For some applications, stabilizing the implant includes removably coupling a stabilization tool to the stabilization surface of the applicator body, and applying the stabilizing force to the stabilization surface using the stabilization tool.

In an embodiment, the applicator further includes a retaining element, which is configured to assume a first position in which the retaining element prevents the distal tube end from separating from the implant, and a second position in which the retaining element does not prevent the distal tube end from separating from the implant, and decoupling the delivery tube from the implant includes positioning the retaining element in the second position. For some applications, the distal tube end is shaped so as to define a cone.

For some applications, the implant has a distal implant portion that extends from a distal implant end along up to 50% of a longitudinal length of the implant, and the lumen is shaped so as to define at least one distal opening through a distal external surface of the distal implant portion.

For some applications, the implant has a proximal-most part, and the lumen is not open to a proximal external surface of the implant within 2 mm of the proximal-most part of the implant.

There is also provided, in accordance with an embodiment of the present invention, apparatus including:

a dental implement, having a distal portion that extends from a distal end along up to 50% of a longitudinal length of the implement, the implement being shaped so as to define a lumen therethrough having at least one distal opening through a center of the distal end, and the implement having a greatest diameter no more than 8 mm and a length of at least 3 mm, wherein at least a portion of a lateral external surface of the implement is shaped so as to define a cutting surface, wherein at least a portion of the distal portion is shaped so as to define at least one surface selected from the group consisting of: at least one end mill cutter surface, at least one self-tapping surface, and both the at least one end mill cutter surface and the at least one self-tapping surface, and wherein the selected at least one surface does not extend into a central area of the implement that defines the lumen.

In an embodiment, the distal portion is shaped so as to define both the at least one end mill cutter surface and the at least one self-tapping surface. Alternatively, the distal portion is shaped so as to define the at least one self-tapping surface. Further alternatively, the distal portion is shaped so as to define the at least one end mill cutter surface.

For some applications, the distal portion is shaped so as to define a plurality of end mill cutting surfaces that are distributed about a central axis of the implement, such that lines respectively defined by the cutting surfaces are tangential to a circle having a center which is intersected by the central axis of the implement.

For some applications, the selected at least one surface does not extend into a cylindrical area of the implement, a central axis of which area coincides with a central axis of the implement, which area extends along the entire length of the implement, and which cylindrical area has a diameter of at least 0.3 mm.

For some applications, the selected at least one surface is tripartite.

In an embodiment, the dental implement includes a dental implant.

In an embodiment, the dental implement includes a dental osteotome.

In an embodiment, the dental implement includes a dental drilling element.

In an embodiment, the dental implement further includes a swivel joint having first and second joint portions defining first and second joint ports, respectively, the swivel joint arranged so as to define a fluid path from the lumen to the second joint port via the first joint port, the first joint portion, and the second joint portion, which joint portions are arranged to be rotatable with respect to one another such that the fluid path is preserved during rotation.

For some applications, the implement has a proximal-most part, a lateral surface, and a proximal external surface, and the implement is shaped such that the lumen has a lateral opening through the lateral external surface, and the lumen is not open to the proximal external surface of the implement within 2 mm of the proximal-most part of the implement.

There is further provided, in accordance with an embodiment of the present invention, apparatus including:

a dental implement having a distal portion that extends from a distal end of the implement, the implement shaped so as to define a lumen through the implement, which lumen has at least one distal opening through a distal external surface of the distal portion, and at least a portion of a lateral external surface of the implement is shaped so as to define a cutting surface; and a swivel joint having first and second joint portions defining first and second joint ports, respectively, the swivel joint arranged so as to define a fluid path from (a) the lumen, to (b) the first joint port, to (c) the first joint portion, to (d) the second joint portion, to (e) the second joint port, and the first and second joint portions are arranged to be rotatable with respect to one another such that the fluid path is preserved during rotation.

In an embodiment, the dental implement includes a dental osteotome.

In an embodiment, the dental implement includes a dental drilling element.

For some applications, the first joint portion is positioned distal to the second joint portion. Alternatively, the first joint portion is positioned proximal to the second joint portion.

For some applications, the first joint port is positioned on a surface of the first joint portion facing the dental implement, and a proximal end of the lumen has a lateral opening through the lateral external surface of the implement, which lateral opening is in fluid communication with the first joint port.

For some applications, a proximal end of the lumen has a lateral opening through the lateral external surface of the implement, and the swivel joint further includes a delivery tube that couples the lateral opening to the first joint port in fluid communication.

There is still further provided, in accordance with an embodiment of the present invention, a method including:

forming a first bore through an alveolar ridge at a first bore location;

lifting a Schneiderian membrane to form a cavity between the ridge and the membrane by injecting a liquid under the Schneiderian membrane via the first bore;

forming a second bore through the ridge at a second bore location at least 1 mm from the first bore location; and introducing a regenerative material into the cavity via the second bore.

For some applications, forming the first bore includes inserting a dental implement into the ridge and rotating the implement to form the first bore, and injecting the liquid includes injecting the liquid via a lumen of the implement.

For some applications, inserting the dental implement includes inserting a dental implant.

For some applications, inserting the dental implement includes inserting a dental osteotome.

For some applications, inserting the dental implement includes inserting a dental drilling element.

There is additionally provided, in accordance with an embodiment of the present invention, a method including:

providing a dental implant having a proximal implant end, and a distal implant portion that extends from a distal implant end along up to 50% of a longitudinal length of the implant, the implant shaped so as to define a lumen therethrough (a) having at least one distal opening through a distal external surface of the distal implant portion, and (b) open to the proximal a proximal implant end through a proximal opening;

forming a bore through a ridge;

inserting the implant into the bore; and after inserting the implant into the bore, sealing the proximal opening of the implant.

For some applications, forming the bore includes forming at least a portion of the bore by inserting the implant into the ridge and rotating the implant.

In an embodiment, sealing the proximal opening includes placing a filling material in the proximal opening.

In an embodiment, sealing the proximal opening includes sealingly coupling a mechanical plug to the proximal opening. For some applications, the mechanical plug is shaped so as to define a male Morse taper, the proximal opening is shaped so as to form a corresponding female Morse taper, and sealing includes inserting the male Morse taper of the plug into the female Morse taper of the opening.

In an embodiment, sealing the proximal opening includes sealingly coupling a screw covering to the proximal opening using a gasket.

In an embodiment, sealing the proximal opening includes welding a covering to the opening.

In an embodiment, sealing the proximal opening includes crimping a covering to the opening.

There is yet additionally provided, in accordance with an embodiment of the present invention, apparatus including a dental kit, which includes:

a dental implant having a proximal implant end, and a distal implant portion that extends from a distal implant end along up to 50% of a longitudinal length of the implant, the implant shaped so as to define a lumen therethrough (a) having at least one distal opening through a distal external surface of the distal implant portion, and (b) open to the proximal a proximal implant end through a proximal opening; and a sufficient quantity of filling material to seal the proximal opening of the implant.

For some applications, the filling material includes a material selected from the group consisting of: rubber and glue.

There is also provided, in accordance with an embodiment of the present invention, apparatus including a dental kit, which includes:

a dental implant having a proximal implant end, and a distal implant portion that extends from a distal implant end along up to 50% of a longitudinal length of the implant, the implant shaped so as to define a lumen therethrough (a) having at least one distal opening through a distal external surface of the distal implant portion, and (b) open to the proximal a proximal implant end through a proximal opening; and a mechanical plug, wherein the proximal opening and the plug are configured such that plug the can be sealingly coupled to the proximal opening.

For some applications, the mechanical plug is shaped so as to define a male Morse taper, and the proximal opening is shaped so as to form a corresponding female Morse taper.

There is further provided, in accordance with an embodiment of the present invention, a method including:

providing a dental implement having a distal portion that extends from a distal end along up to 50% of a longitudinal length of the implement, the implement shaped so as to define a lumen therethrough having at least one distal opening through a distal external surface of the distal portion;

forming a bore in bone of an alveolar ridge;

inserting the implement into the bore at least until the distal opening comes into fluid communication with periosteal tissue covering a lateral surface of the bone; and delaminating the periosteal tissue from the bone by injecting a fluid through the lumen to form a cavity between the bone and the periosteal tissue.

In an embodiment, providing the dental implement includes providing a dental implant.

In an embodiment, providing the dental implement includes providing a dental osteotome.

In an embodiment, providing the dental implement includes providing a dental drilling element.

For some applications, forming the bore includes forming at least a portion of the bore by inserting the implement into the ridge and rotating the implement.

For some applications, forming the bore includes forming a preparatory portion of the bore using a dental drill, and subsequently forming the at least a portion of the bore by inserting the implement into the ridge and rotating the implement.

For some applications, the method further includes, after delaminating the periosteal tissue, injecting a regenerative material into the cavity via the lumen. For some applications, providing the dental implement includes providing a dental implant, and the method further includes, after injecting the regenerative material, advancing the dental implant into the cavity. For some applications, injecting the fluid includes measuring a volume of the injected fluid, and injecting the regenerative material includes determining an amount of the regenerative material to inject into the cavity responsively to the measured volume of the fluid.

In an embodiment, the alveolar ridge is a maxillary alveolar ridge, and forming the bore includes forming the bore in the bone of the maxillary alveolar ridge. Alternatively, the alveolar ridge is a mandibular alveolar ridge, and forming the bore includes forming the bore in the bone of the mandibular alveolar ridge.

The present invention will be more fully understood from the following detailed description of embodiments thereof, taken together with the drawings, in which:

BRIEF DESCRIPTION OF THE DRAWINGS

FIGS. 7, 8, 9A-E, and 10 are schematic illustrations of the implant of FIG. 1 and an applicator comprising a retaining element, in accordance with an embodiment of the present invention;

FIGS. 11A-I are schematic illustrations of several steps of a minimally-invasive closed sinus lift surgical procedure for implanting the dental implant of FIG. 1, in accordance with an embodiment of the present invention;

FIGS. 12A and 12B are schematic illustrations of tools and techniques, respectively, for decoupling a delivery tube from the implant of FIGS. 3A-D, 4A-B, 5, and 6, in accordance with an embodiment of the present invention;

FIGS. 12C and 12D-E are schematic illustrations of a tool and techniques, respectively, for decoupling the applicator from the implant of FIGS. 3A-D, 4A-B, 5, and 6, in accordance with an embodiment of the present invention;

FIGS. 21A-E are schematic illustrations of another dental implant, in accordance with respective embodiments of the present invention;

FIGS. 22A-F are schematic illustrations of several steps of a minimally-invasive closed lateral ridge augmentation surgical procedure for implanting a dental implant, in accordance with an embodiment of the present invention;

FIGS. 23A-F are schematic illustrations of several steps of another minimally-invasive closed lateral ridge augmentation surgical procedure for implanting a dental implant, in accordance with an embodiment of the present invention;

FIGS. 26 and 27A-B are schematic illustrations of another liquid osteotome, in accordance with an embodiment of the present invention.

DETAILED DESCRIPTION OF EMBODIMENTS

Figure 1:
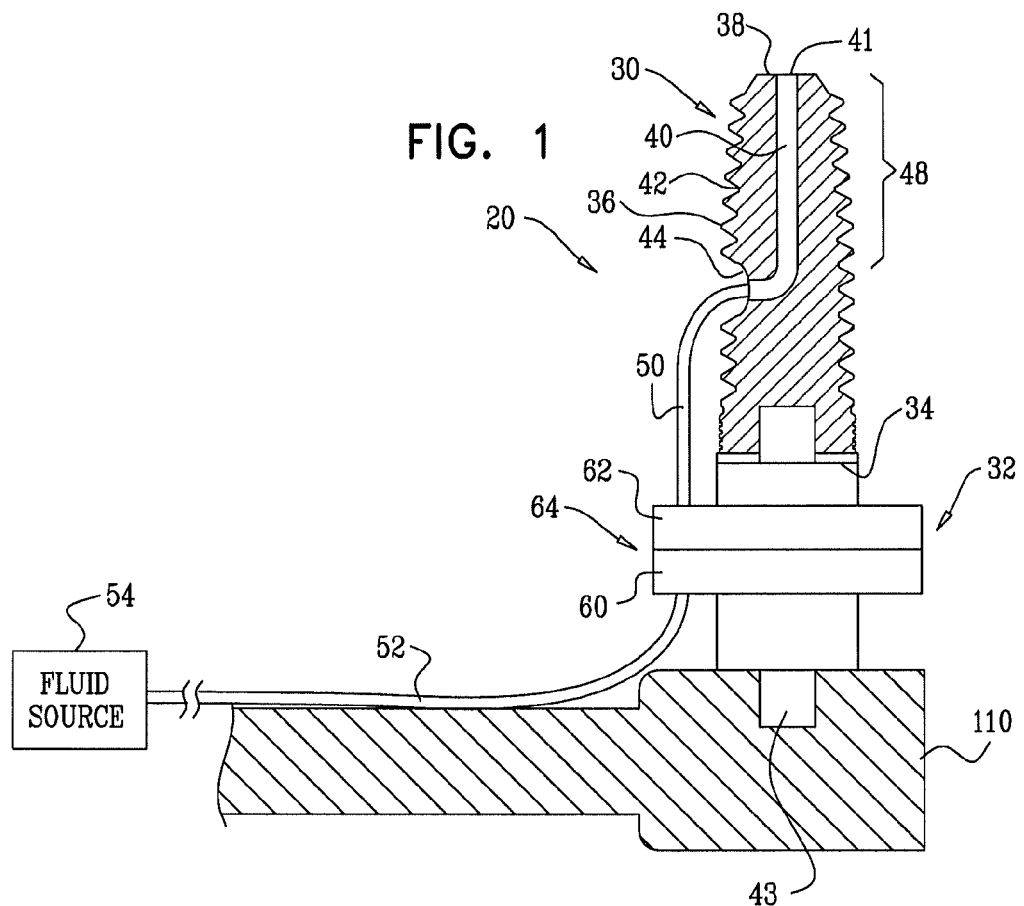
FIG. 1 is a schematic illustration of a dental implant system, in accordance with an embodiment of the present invention.

FIG. 1 is a schematic illustration of a dental implant system 20, in accordance with an embodiment of the present invention. System 20 comprises a dental implant 30, which is typically shaped so as to define a lumen 40 therethrough that is open through a distal opening 41 to a distal portion 48 of the implant that extends from a distal implant end 38 of the implant along up to 50% of a longitudinal length of the implant, such as up to 30% of the length, up to 15% of the length, or up to 5% of the length. For some applications, distal portion 48 has a longitudinal length of up to 6 mm, such as up to 4 mm, or up to 2 mm. As used herein, including in the claims, the "distal" end of the implant is the end that is inserted first into a bone, such as an alveolar ridge, and is sometimes referred to in the art as the apical end, and the "proximal" end of the implant is the end of the implant opposite the distal end, e.g., that faces the oral cavity, and is sometimes referred to in the art as the coronal end. Similarly, "distal" means situated toward the distal end of the implant, and "proximal" means situated toward the proximal end of the implant.

Distal opening 41 may be located at distal implant end 38, such as centered on the distal implant end, e.g., at a distal tip of distal implant end 38, or not centered on the distal implant end (and thus located at a location other than the distal tip), such as described hereinbelow with reference to FIG. 2A. Alternatively, distal opening(s) 41 may be located at one or more locations along distal implant portion 48, including at locations on lateral surface 42. For some applications, the lumen is open to the distal end via a plurality of openings 41, which for some applications results in a more even distribution of regenerative material in the cavity between the ridge and the Schneiderian membrane, as described hereinbelow, and/or permits passage of the regenerative material even if some of the openings should become blocked with bone particles. Dental implant 30 is typically generally cylindrical, tapered, or conic in shape, other than the lumen, and typically comprises a metal such as titanium, or a ceramic, such as a zirconia (zirconium dioxide) ceramic. The implant may have a greatest diameter of between about 2 and about 7 mm, and may be provided in a variety of longitudinal lengths, e.g., between about 7 and about 18 mm, e.g., between about 12 and about 16 mm, such as about 15 mm. For some applications, the implant has a longitudinal length of less than 20 mm and a greatest diameter of less than 10 mm.

In an embodiment of the present invention, dental implant 30 comprises a self-tapping osseointegrated dental implant. In this embodiment, at least a portion of a lateral external surface 42 of implant 30 is typically shaped so as to define a cutting surface, e.g., a screw thread 36, or other connecting element. For example, the portion may be in a vicinity of a distal end 38 of the implant, or may include all or nearly all of the lateral surface.

In an embodiment of the present invention, system 20 comprises an applicator 32 that is removably coupled to a proximal end 34 of implant 30. For some applications, applicator 32 is shaped so as to define a distal male coupling element, e.g., a hexagonal head, that is inserted into a correspondingly shaped proximal female coupling element, e.g., a hexagonal socket, defined by dental implant 30. Friction between the head and socket removably couples the implant to the applicator. Alternatively, another coupling element removably couples the implant to the applicator. A proximal end of applicator 32 is typically shaped so as to define a coupling element 43, such as a male coupling element (as shown in FIG. 1), e.g., a hexagonal head, or a female coupling element (configuration not shown), e.g., a hexagonal socket. Typically, implant 30 comprises a two-stage implant. The surgeon couples an abutment to the proximal end of the implant after osseointegration of the implant, as is known in the art, such as described hereinbelow with reference to FIG. 11F. Alternatively, implant 30 comprises a single-stage transgingival implant, which is shaped so as to define an integrated abutment, as is known in the art.

In an embodiment of the present invention, as shown in FIG. 1, a proximal end of lumen 40 has a lateral opening 44 through lateral external surface 42 of the implant, and the lumen is not open to a proximal external surface of the implant within 2 mm of a proximal-most part of implant 30. For some applications, the lumen is not open to the proximal external surface within 3 mm of the proximal-most part of the implant. Implant 30 is typically permanently closed within 3 mm of the proximal-most part of the implant, in this embodiment. Alternatively, the proximal end of lumen 40 is open to proximal implant end 34, such as described hereinbelow with reference to FIG. 15A, 15C, 16, 21A-E, or 23A-F. Typically, the lateral opening is at least 1.5 mm from distal implant end 38, such as at least 2 mm (e.g., 8 mm from the distal implant end). Typically, the lateral opening is at least 2 mm from the proximal implant end, such as at least 3 mm or at least 4 mm.

System 20 further comprises a delivery tube 50, a distal end of which is coupled to lumen 40 via lateral opening 44. For example, the delivery tube may be coupled to the lumen using a miniature luer connector, by friction, using a removable coupling element (such as described hereinbelow with reference to FIG. 2F), or as described hereinbelow with reference to FIGS. 3A-D, 4A-B, 5, and 6, or FIGS. 7, 8, 9A-E, and 10. Alternatively, the tube may screw into the lumen, so as to be rotationally secured to the implant throughout the implantation procedure. Further alternatively or additionally, the distal end of delivery tube 50 comprises a sealing element, which is configured to removably sealingly couple delivery tube 50 to implant 30. For example, the sealing element may comprise an o-ring or a gasket. Typically, a proximal end of delivery tube 50 is coupled to applicator 32 during at least a portion of an implantation procedure. Delivery tube 50 is in fluid communication with a supply tube 52, which in turn is in fluid communication with a source of fluid 54. Alternatively, delivery tube 50 is coupled directly to fluid source 54, and supply tube 52 is not provided. Fluid source 54 may comprise a syringe or powered drug delivery device.

In an embodiment of the present invention, implant system 20 comprises a swivel joint 64 having proximal and distal joint portions 60 and 62, which define proximal and distal joint ports, respectively. Joint 64 is arranged so as to define a fluid path from the proximal joint port to the distal joint port via proximal and distal joint portions 60 and 62. Proximal and distal joint portions 60 and 62 are arranged to be rotatable with respect to one another such that the fluid path is preserved during rotation. The proximal end of delivery tube 50 is coupled to the distal joint port, and supply tube 52 is coupled to the proximal joint port, such that delivery tube 50 and supply tube 52 are in fluid communication with one another via swivel joint 64. Alternatively, joint 64 is arranged so as to define the fluid path from the distal joint port to the proximal joint port via the distal and proximal joint portions, such as described hereinbelow regarding the swivel joint described with reference to FIG. 27B.

For some applications, as shown in FIG. 1, swivel joint 64 defines a bore therethrough, in which at least a portion of applicator 32 is positioned. The proximal and distal portions of the joint are independently rotatable around the portion of the applicator in the bore. Rotation of coupling element 43 at the proximal end of the applicator causes corresponding rotation of the distal end of the applicator and implant 30. Such rotation of the implant causes corresponding rotation of lateral opening 44 and delivery tube 50, which rotates distal joint portion 62 of swivel joint 64. However, supply tube 52 tends to prevent rotation of proximal joint portion 60 of the swivel joint, causing the proximal and distal joint portions to rotate with respect to one another. Alternatively, the applicator may be rotated by grasping it near or at its distal end. Optionally, distal joint portion 62 of swivel joint 64 is fixed to the body of applicator 32.

For some applications, lumen 40 is open to proximal implant end 34 rather than lateral surface 42. For these applications, the distal joint port may open to the bore of the swivel joint, and be in fluid communication with lumen 40 via a central lumen of the applicator (configuration not shown).

For some applications in which distal joint portion 62 of swivel joint 64 is fixed to the body of applicator 32, the implant is rotated by rotating the distal joint portion. For example, an external surface of the distal joint portion may be shaped so as to define a hexagon that is larger than proximal joint portion 60, and the distal joint portion may be rotated using a hexagonal ratchet wrench.

In an embodiment of the present invention, system 20 does not comprise applicator 32. System 20 comprises swivel joint 64, which, for some applications, is coupled to implant 30 only by delivery tube 50. To rotate the implant, a head of a wrench or other tool (e.g., a straight hexagonal screwdriver having a length of about 3 to 4 cm, optionally with a knurled handle) is temporarily inserted through the bore of the swivel joint, and coupled to the coupling element of the implant, which may be a hexagonal socket, for example. Alternatively, the swivel joint is removably coupled to the implant, and removed when delivery tube 50 is decoupled from the implant, as described hereinbelow with reference to FIG. 11E. For some applications in which the swivel joint is removably coupled to the implant, distal joint portion 62 is shaped so as to define a coupling element, such as a hexagonal coupling element, and the implant is rotated by rotating the coupling element using a wrench or hexagonal screwdriver.

Figure 2A:
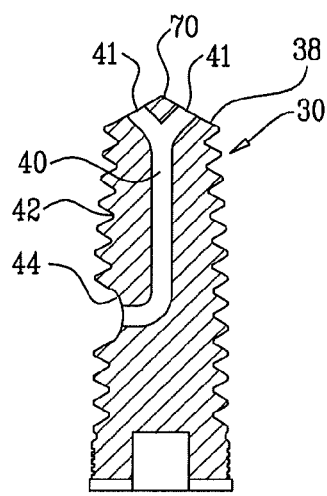
FIGS. 2A-C are schematic illustrations of alternative configurations of a dental implant of the dental implant system of FIG. 1, in accordance with respective embodiments of the present invention.
Figure 2B:
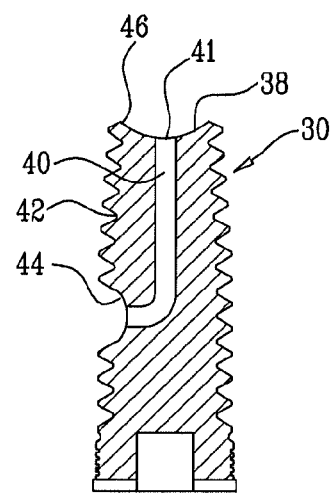
Figure 2C:
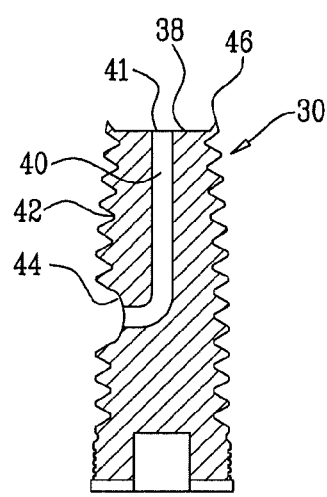

Reference is made to FIGS. 2A-C, which are schematic illustrations of alternative configurations of dental implant 30, in accordance with respective embodiments of the present invention. In the configuration shown in FIG. 2A, distal opening 41 of lumen 40 is located on distal implant end 38 at a location other than a distal tip 70 of the implant. For some applications, the location is within 3 mm of distal tip of 70, as measured along the surface of the distal tip. As mentioned above with reference to FIG. 1, for some applications, lumen 40 is open to the distal end via a plurality of distal openings 41, as shown in FIG. 2A. One or more of the openings may be at a location other than distal tip 70, including at one or more locations at distal implant end 38 and/or elsewhere on distal implant portion 48. Alternatively, lumen 40 is open to distal implant end 38 or distal implant portion 48 via exactly one opening (configuration not shown in FIG. 2A).

In the configuration shown in FIG. 2B, distal implant end 38 is concave, such that the raised edge of the concavity defines a sharp cutting surface 46. In the configuration shown in FIG. 2C, distal implant end 38 is generally flat, and the distal end is shaped so as to define sharp cutting surface 46, typically near the edge of the distal end.

Figure 2D:
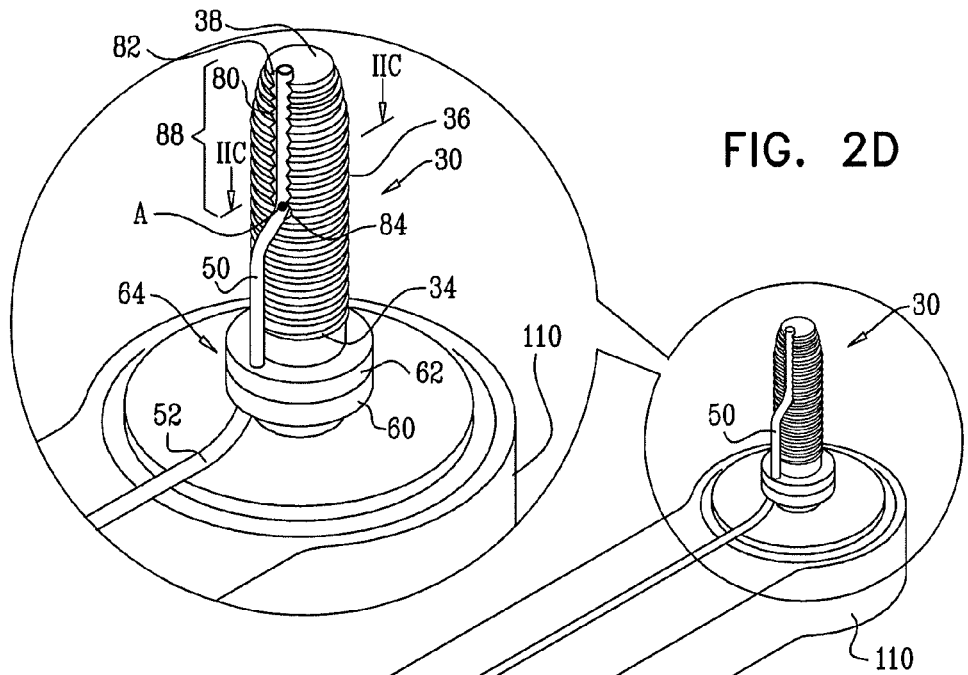
FIG. 2D is a schematic illustration of yet another configuration of the dental implant of FIG. 1.
Figure 2E:
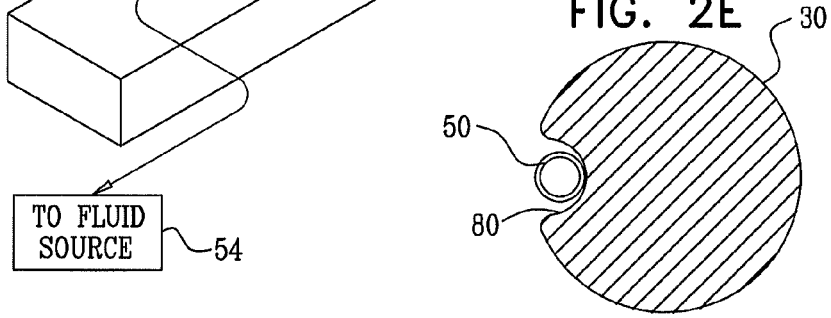
FIG. 2E is a cross-sectional view taken along line IIC-IIC of FIG. 2D, in accordance with an embodiment of the present invention.

Reference is made to FIG. 2D, which is a schematic illustration of yet another configuration of dental implant 30, and FIG. 2E, which is a cross-sectional view taken along line IIC-IIC of FIG. 2D, in accordance with an embodiment of the present invention. In this embodiment, lateral surface 42 of dental implant 30 is indented so as to define a channel 80 along the lateral surface between a first location 82 on the lateral surface in a vicinity of distal implant end 38, and a second location 84 on the lateral surface between distal implant end 38 and proximal implant end 34, not inclusive (i.e., the channel typically does not extend all of the way to the proximal implant end). A distal portion 88 of delivery tube 50 is positioned within the channel, such that the distal end of the delivery tube is open to distal end 38 of the implant. Alternatively, the distal end of the delivery tube is open to a location along the channel, such as a location on distal implant portion 48. For example, the distal end of the delivery tube may reach a point A in a vicinity of second location 84, such that only a small portion of the delivery tube is positioned within the channel. Typically, at least a portion of lateral surface 42 is shaped so as to define screw thread 36, at least a portion of which may or may not act as a cutting surface, and which comprises a raised helical rib going around implant 30. Channel 80 crosses the rib at a plurality of sites on the lateral surface. Typically, the second location is at least 2 mm from proximal implant end 34, such as at least 3 mm or at least 4 mm.

A number of embodiments of the present invention include positioning of lateral opening 44 (e.g., in ridge 100 and/or in regenerative material 130). The techniques of the embodiment described with reference to FIG. 2D may be performed in combination with the techniques of these embodiments by substituting second location 84 for lateral opening 44.

Figure 2F:
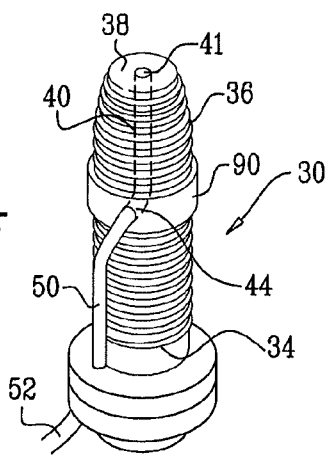
FIG. 2F is a schematic illustration of a removable coupling element coupled to the dental implant of FIG. 1, in accordance with an embodiment of the present invention.
Figures 3A, 3B:
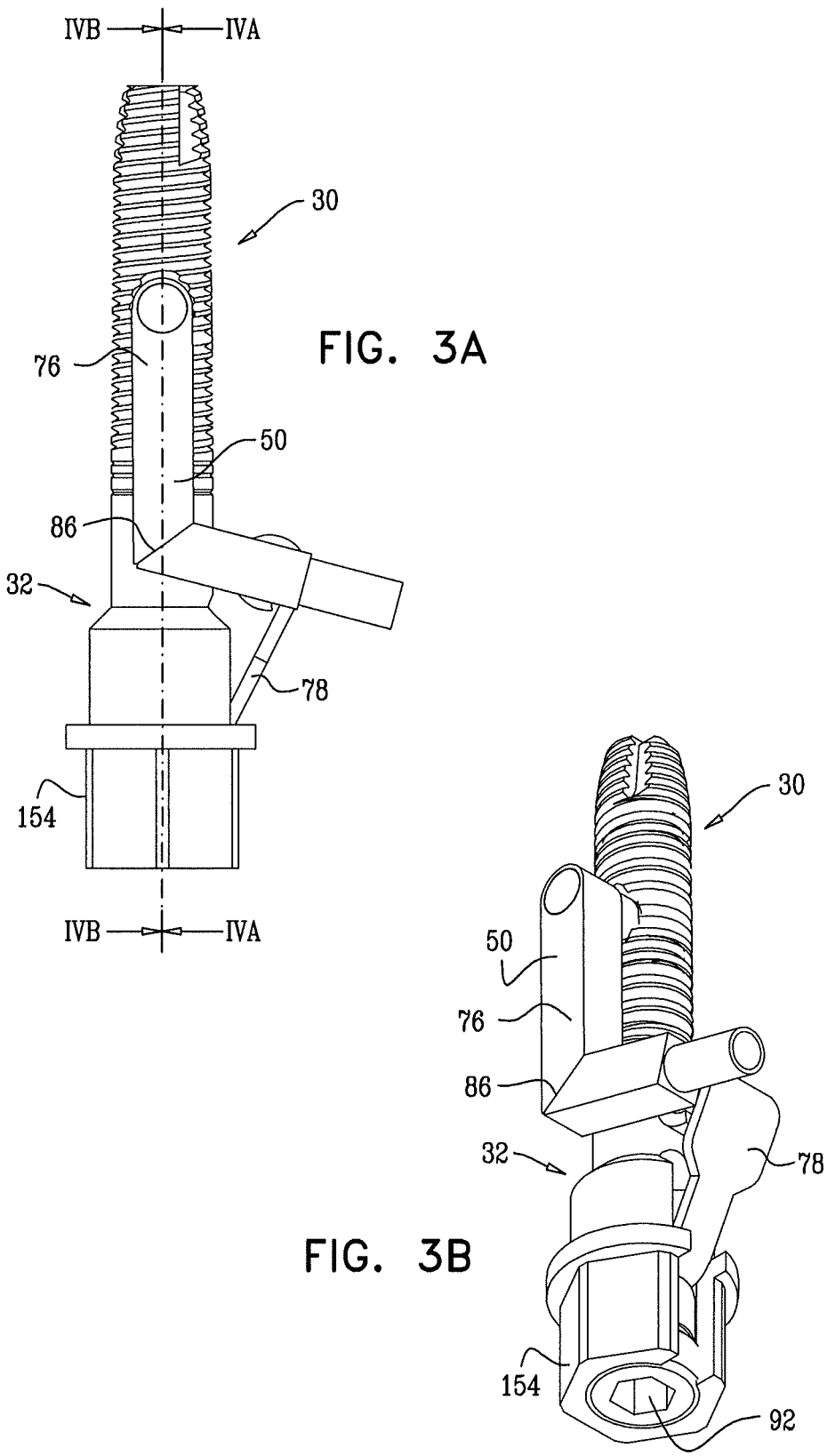
FIGS. 3A-D, 4A-B, 5, and 6 are schematic illustrations of the implant of FIG. 1 and an applicator in which the distal end of a delivery tube is initially welded to the implant, in accordance with an embodiment of the present invention.
Figure 3C:
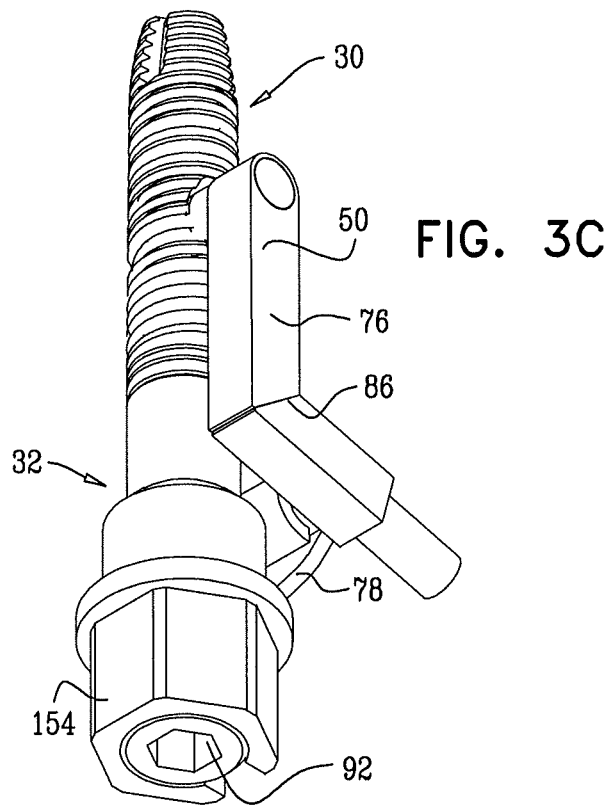
Figure 3D:
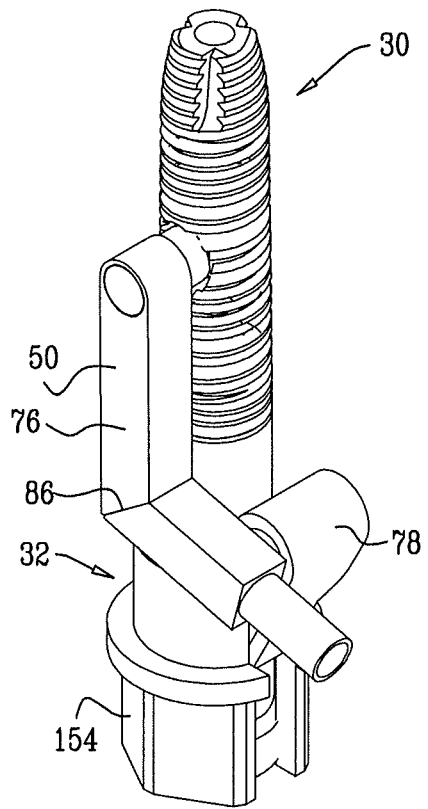

Reference is made to FIG. 2F, which is a schematic illustration of a removable coupling element 90 coupled to implant 30, in accordance with an embodiment of the present invention. Removable coupling element 90 removably secures delivery tube 50 to lateral opening 44. When the surgeon decouples delivery tube 50 from implant 30, as described hereinbelow with reference to FIG. 11E, the surgeon also decouples coupling element 90 from the implant. The coupling element is typically removably coupled to an external surface of the implant. For some applications, coupling element 90 is configured to be placed around at least a portion of the circumference of the implant, such as the entire circumference.

In an embodiment, coupling element 90 comprises an elastic band that is placed around the entire circumference of the implant, as shown in FIG. 2F. The distal end of delivery tube 50 may pass through an opening in the band, such that the band holds the tube in place coupled to lateral opening 44. For other applications, coupling element 90 comprises a more rigid material.

Figure 4A:
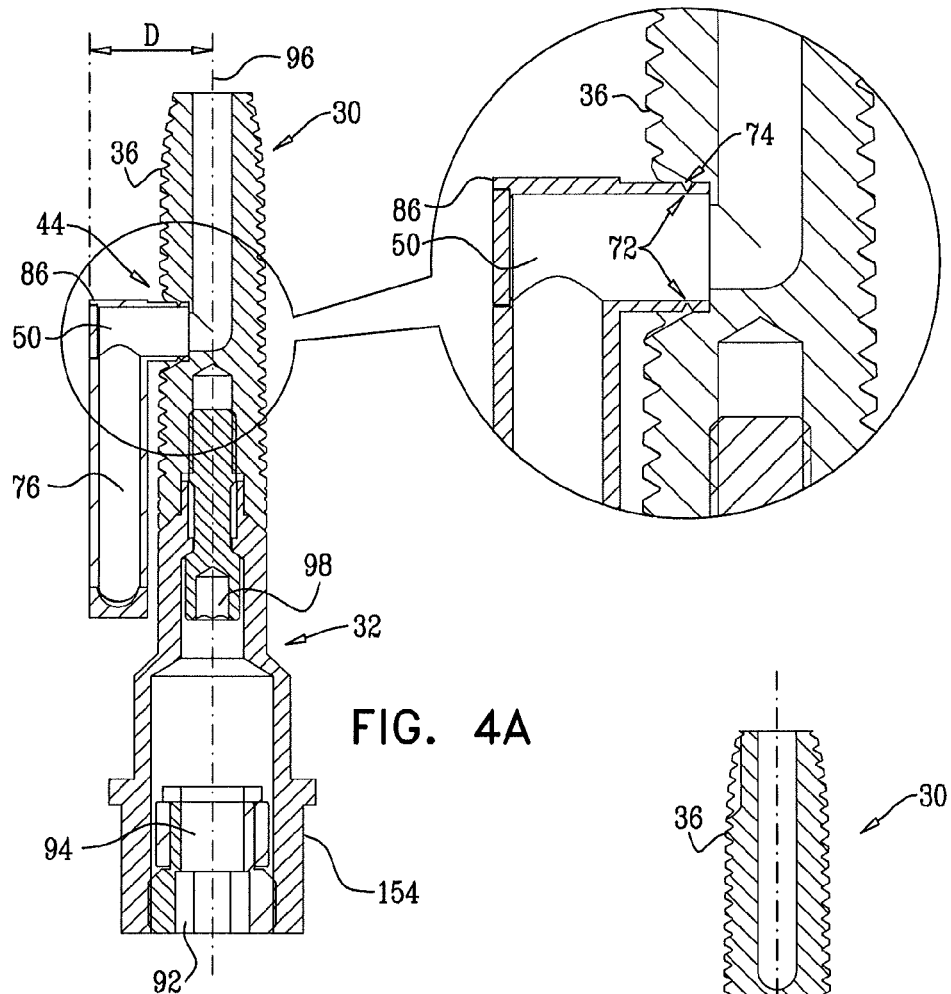
Figure 4B:
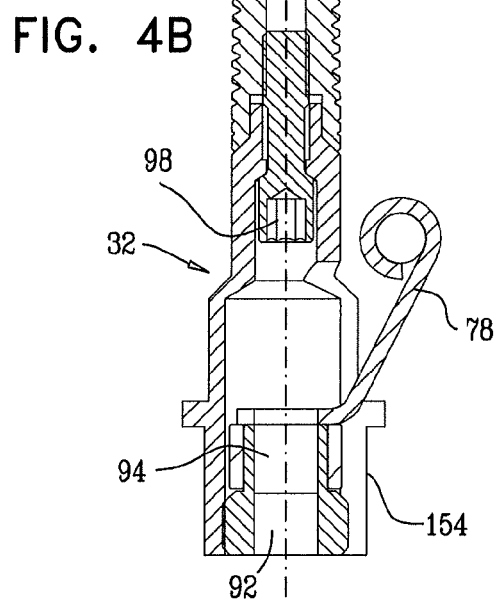
Figure 5:
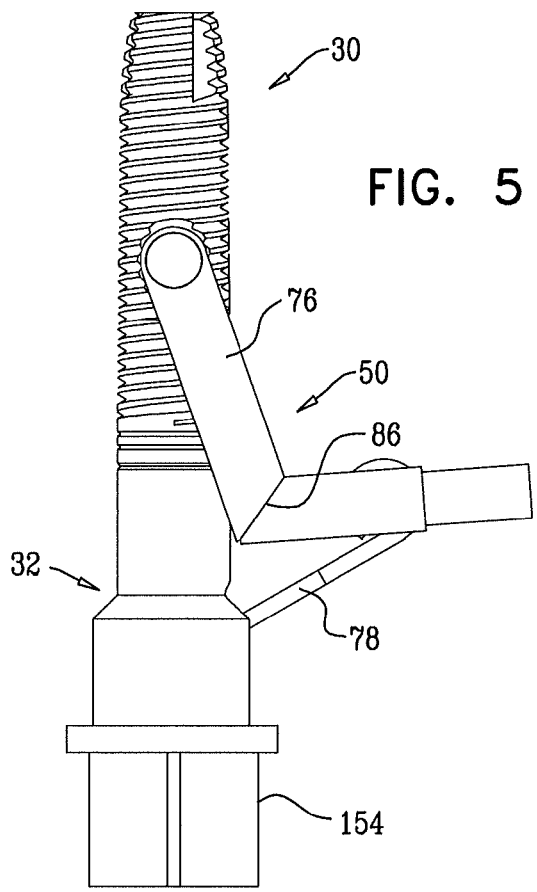
Figure 6:
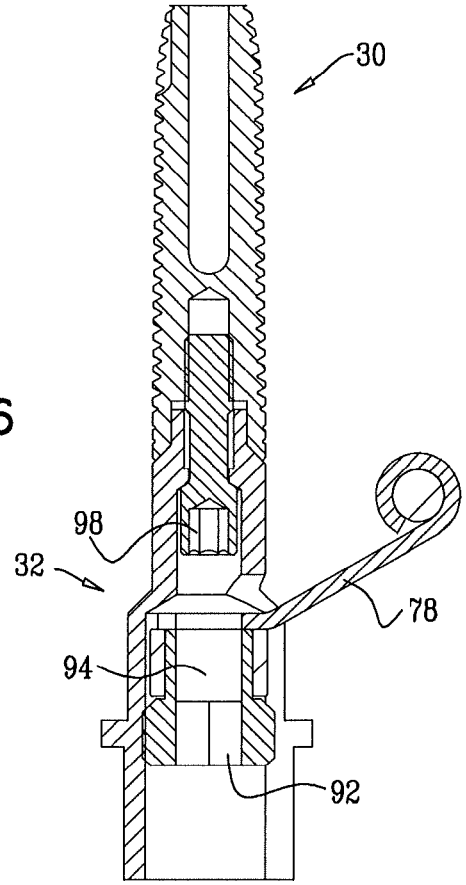

Reference is made to FIGS. 3A-D, 4A-B, 5, and 6, which are schematic illustrations of dental implant 30 and applicator 32 in which the distal end of delivery tube 50 is initially welded to implant 30, in accordance with an embodiment of the present invention. FIGS. 3A-D are views from respective directions of the implant and applicator in which delivery tube 50 is coupled to the implant, such that the delivery tube is in fluid communication with lumen 40 of implant 30 via lateral opening 44 of implant 30. FIGS. 4A-B are cross-sectional views taken along lines IVA-IVA and IVB-IVB of FIG. 3A, respectively. FIG. 5 shows the implant and applicator after the delivery tube has been broken, as described hereinbelow, and FIG. 6 is a cross-sectional view of FIG. 5.

The welding of delivery tube 50 to implant 30 provides a strong seal that is able to withstand the pressure of the fluid provided by fluid source 54 (as described hereinbelow with reference to FIGS. 11B and 11C) and the injection of a regenerative material (as described hereinbelow with reference to FIG. 11D). The delivery tube may be welded to implant 30 by laser welding overlapping spots around the circumference of the delivery tube.

As best seen in the blow-up in FIG. 4A, a portion 72 of the wall of delivery tube 50 is thinner than the wall immediately adjacent to the portion, such that application of a breaking torque to the delivery tube breaks the delivery tube at the thinner portion, thereby decoupling the delivery tube from the implant. Typically, the thinner portion is within 3 mm of the distal end of the delivery tube, such as within 2 mm or within 1 mm of the distal end. The thinner portion is typically recessed into lateral external surface 42 of the implant. For some applications, at least a portion of the lateral surface that includes lateral opening 44 is shaped so as to define screw thread 36, as described hereinabove with reference to FIG. 1. For these applications, the thinner portion is recessed into the lateral external surface below the raised helical rib of screw thread 36. As a result, the small distal broken portion of the delivery tube that remains coupled to the implant after the delivery tube is broken does not interfere with the functioning of screw thread 36.

Typically, thinner portion 72 of delivery tube 50 is sufficiently thin such that the application of a breaking torque of less than 50 Newton centimeters (Ncm) breaks the delivery tube at the thinner portion. For some applications, the thinner portion has a width of less than 0.1 mm, such as less than 0.05 mm.

In this embodiment, delivery tube 50 typically comprises a rigid material, such as metal. For some applications, the delivery tube is shaped so as to be circumscribed with a groove 74 that defines thinner portion 72. For example, the tube may be manufactured by scoring the implant to form the groove that serves as the thinner portion. Typically, the groove is V-shaped, such that application of the breaking torque causes a concentration of force to be applied at the tip of the V, thereby breaking the delivery tube at the groove.

For some applications, the delivery tube is shaped so as to define a bend 86 at between about 5 and about 20 mm from the distal tube end, such as within about 10 mm of the distal tube end. For example, the bend may have an angle of between about 85 and about 95 degrees.

In an embodiment of the present invention, applicator 32 is configured to break delivery tube 50 at thinner portion 72 by rotating the distal end of the delivery tube with respect to lateral opening 44 of the implant. Typically, applicator 32 is configured to apply a torque of greater than 50 Newton centimeters to the delivery tube, when rotating the distal tube end with respect to the lateral opening. The applicator typically applies the torque to the delivery tube without applying any meaningful torque to the implant itself, and thus does not dislodge or misalign the implant, which has been precisely placed in a bore in the ridge, as described hereinbelow with reference to FIG. 11B. For some applications, a portion 76 of delivery tube 50 is initially positioned generally parallel to a central longitudinal axis 96 of implant 30 before thinner portion 72 is broken, as shown in FIGS. 3A-D and 4A-B. Applicator 32 rotates the distal end of the delivery tube by rotating portion 76 between about 5 and about 20 degrees, e.g., about 10 degrees, until thinner portion 72 breaks, as shown in FIGS. 5 and 6.

Typically, when delivery tube 50 is coupled to the implant prior to breaking of thinner portion 72, portion 76 of the delivery tube runs alongside the implant such that, as shown in FIG. 4A, a greatest distance D between longitudinal axis 96 of the implant and a surface of portion 76 of the delivery tube furthest from the longitudinal axis is less than 6 mm, such as less than 5 mm. Such a small distance allows the implant and delivery tube to be readily placed between adjacent teeth during an implantation procedure, such as described hereinbelow with reference to FIGS. 11B-D.

For some applications, applicator 32 comprises a lever arm 78, which is coupled to delivery tube 50 and arrange to rotate the distal tube end with respect to lateral opening 44. For some applications, the delivery tube is shaped so as to define bend 86 at between about 5 and about 20 mm from the distal tube end, and lever arm 78 is coupled to the delivery tube at a location proximal to the bend. For these applications, the bend typically has an angle of between 85 and 180 degrees. For some applications, applicator 32 comprises a rotatable surface 92 accessible from a proximal end of the applicator, which rotatable surface is rotatable with respect to a portion of the applicator. Rotation of rotatable surface 92 rotates the distal tube end by extending lever arm 78. For example, rotation of the rotatable surface may distally advance a transfer element 94 that extends the lever arm. For example, rotatable surface 92 may define an internal hex, e.g., having an internal width of about 2.4 mm (the hex width is the distance between parallel sides of the hexagon).

In an embodiment of the present invention, applicator 32 comprises a connecting element, which removably couples the applicator to the proximal implant end. For some applications, the connecting element comprises a connecting screw 98. Typically, the head of screw 98 is accessible from a channel than passes through rotatable surface 92, such that the head can be rotated with a screwdriver tool inserted through the proximal end of the applicator, in order to decouple the applicator from the implant. For example, the connecting screw may define an internal hex that has an internal width less than that of rotatable surface 92, e.g., about 1.25 mm. For some applications, the applicator is configured such that rotation of rotatable surface 92 both (a) applies the breaking torque to the delivery tube that breaks the delivery tube at the thinner portion, and (b) rotates screw 98 to decouple the applicator from the proximal implant end.

For other applications, the connecting element does not comprise a screw, and instead comprises one or more surfaces, such as conical surfaces, that are configured to removably couple the applicator to the proximal implant end by friction. For example, the applicator may comprises a male coupling element, that is configured to be coupled to a female coupling element of the implant.

Figures 7, 8:
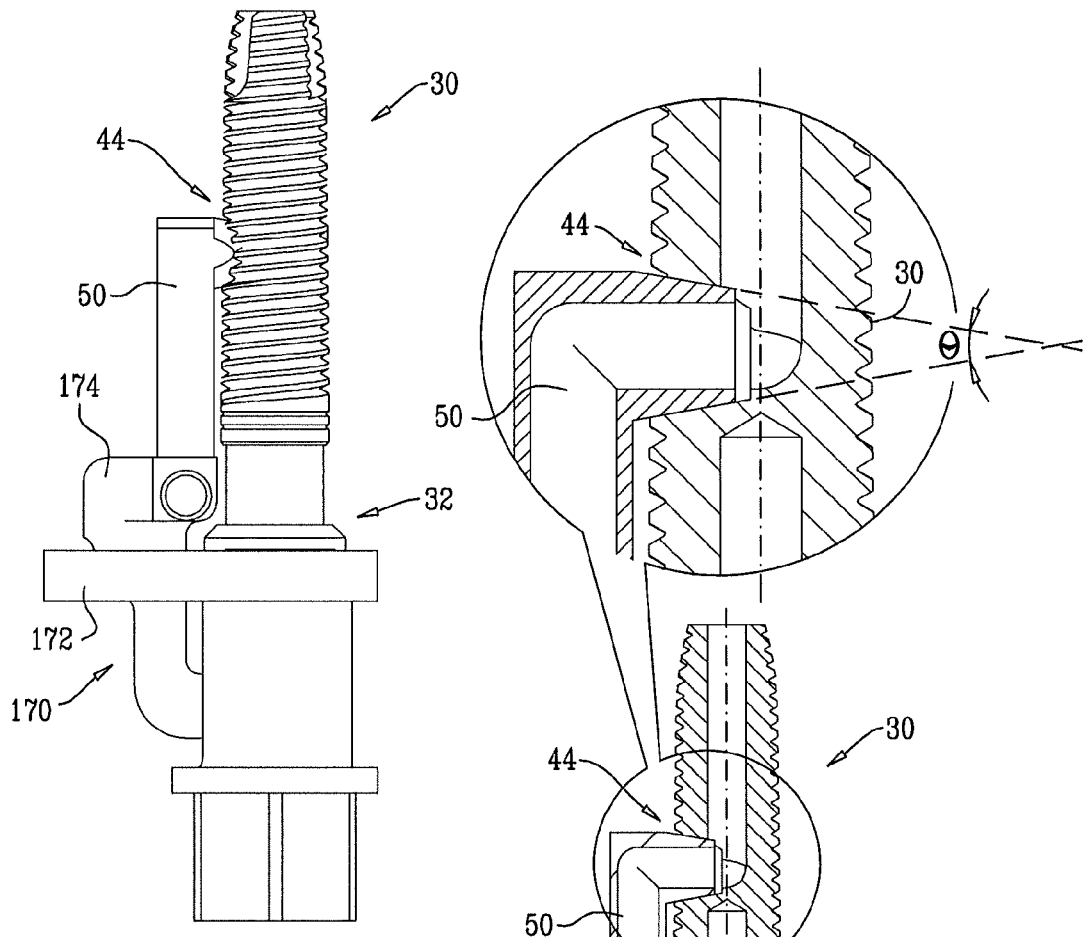

Reference is made to FIGS. 7, 8, 9A-E, and 10, which are schematic illustrations of dental implant 30 and applicator 32 comprising a retaining element 170, in accordance with an embodiment of the present invention. FIG. 7 and FIG. 8 (a cross-section view of FIG. 7) show retaining element 170 in a first position in which the retaining element prevents the distal end of delivery tube 50 from separating from implant 30. Retaining element 170 thus holds the distal end of delivery tube 50 sealingly coupled to implant 30 such that the delivery tube is in fluid communication with lumen 40 of implant 30 via lateral opening 44 of implant 30.

FIGS. 9A-E are views from respective directions in which retaining element 170 assumes a second position in which the retaining element does not prevent the distal tube end from separating from the implant, such that delivery tube 50 becomes decoupled from the implant. FIG. 10 is a cross-sectional view of FIG. 9A. Retaining element 170 provides a strong seal that is able to withstand the pressure of the fluid provided by fluid source 54, (as described hereinbelow with reference to FIGS. 11B and 11C) and the injection of a regenerative material (as described hereinbelow with reference to FIG. 11D).

For some applications, the distal end of delivery tube 50 is shaped so as to define a cone. For example, as shown in FIG. 8, the cone may have an opening angle θ (theta) of between 0 and 90 degrees, such as between about 0 and about 60 degrees. For some applications, the cone forms a Morse taper, in which case the distal end of delivery tube 50 must be removed with force when retaining element 170 assumes the second position.

For some applications, retaining element 170 comprises a retaining element body 172, a pivoting element 174, and a proximal blocking element 176. Delivery tube 50 is coupled to the pivoting element. The pivoting element is configured to pivot with respect to the retaining element body, such that the delivery tube also pivots with respect to the retaining element body, and thereby with respect to applicator 32.

Blocking element 176 can be advanced distally and withdrawn proximally within applicator 32, such as by rotating the blocking element. When in a distal position, the blocking element prevents pivoting element 174 from pivoting freely, thereby causing retaining element 170 to assume the first position in which the retaining element prevents the distal end of delivery tube 50 from separating from implant 30. When in a proximal position, the blocking element does not interfere with the pivoting of pivoting element 174, thereby allowing retaining element 170 to assume the second position in which the retaining element does not prevent the distal end of delivery tube 50 from separating from implant 30.

For some applications, as shown in FIGS. 9D-E, applicator 32 further comprises a spring 178, which is configured to apply a force that separates the distal tube end from the implant when the retaining element assumes the second position.

For some applications, the distal end of delivery tube 50 comprises a sealing element, which is configured to removably sealingly couple delivery tube 50 to implant 30. For example, the sealing element may comprise an o-ring or a gasket.

Figure 11A:
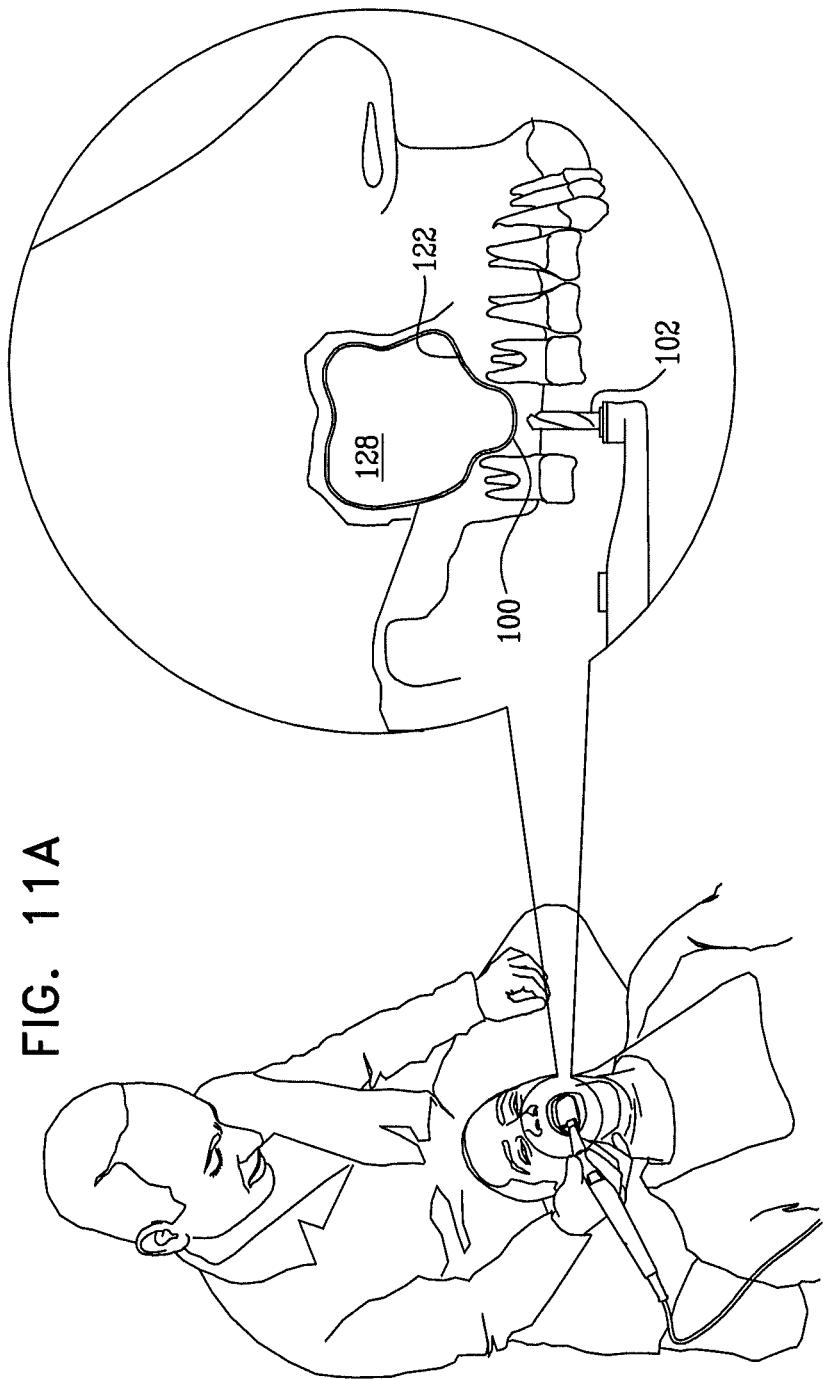

Reference is made to FIGS. 11A-F, which are schematic illustrations of several steps of a minimally-invasive closed sinus lift surgical procedure for implanting dental implant 30, in accordance with an embodiment of the present invention. The procedure is typically employed when a patient's maxillary alveolar ridge lacks sufficient bone mass to support a conventional dental implant. A surgeon begins the procedure by preparing the oral facial region, and administering a local anesthetic. Optionally, as shown in FIG. 11A, the surgeon initiates an osteotomy in a maxillary alveolar ridge 100 by making a preliminary portion of a bore using a dental drill, such as a conventional sinus bur 102. This preliminary bore portion typically has a diameter of between about 1 and about 7 mm, e.g., between about 2 and about 6 mm, and leaves residual bone thickness of between about 0.5 and about 5 mm, e.g., between about 1 and about 4 mm, or between about 0.5 and about 2 mm. Optionally, the surgeon widens the bore using a series of successively wider drill bits, until a desired bore diameters is achieved (for example, the largest drill bit may have a diameter of 3.65 mm for an implant having a diameter of 4.2 mm, or a diameter of 4.2 mm for an implant having a diameter of 5 mm). The bore may be measured using techniques known in the art, such as CT, x-ray, or x-ray with a depth guide. For some applications, a surgical guide is used to ensure clearance between the center of the osteotomy and the nearest tooth surfaces. Optionally, a pre-surgery radiograph (e.g., CT or x-ray) is performed, in order to enable the surgeon to estimate the height of the residual bone and plan the osteotomy accordingly.

Figure 11B:
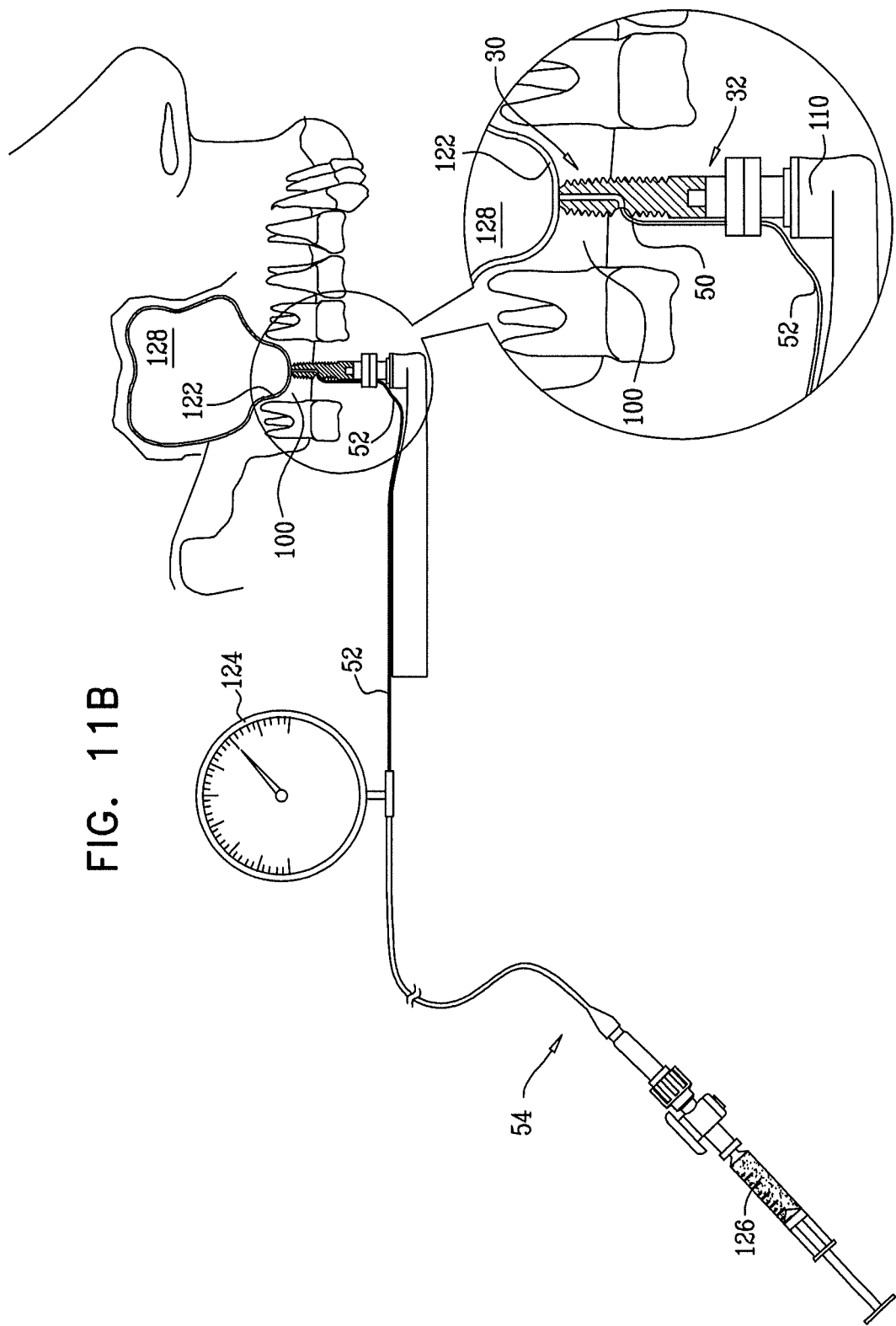

After drilling the preliminary bore portion, the surgeon advances dental implant 30 into the bore by screwing the implant into ridge 100 using a surgical screwing tool 110, as shown in FIG. 11B. Screwing tool 110 may comprise a conventional manual ratchet wrench, or a conventional drill or motor to which an appropriate drill head is attached, and which is operated at a low speed and at low torque. Alternatively, screwing tool 110 may comprise a conventional hexagonal tool with a knurled knob, such as a knurled hex screwdriver, and along its axis, a thin rod having a hexagonal head which fits into a female hexagonal socket defined by a proximal end of applicator 32.

While the surgeon screws the implant, fluid source 54 provides a fluid under monitored pressure to distal implant portion 48, such as distal implant end 38, via supply tube 52, delivery tube 50, and lumen 40. The fluid typically comprises a biocompatible solution such as normal saline solution, or a gas, e.g., air. Implant 30 functions as a cork that isolates the distal end of the bore from the oral cavity, allowing relatively high pressure to develop in the fluid distal to the implant, without being released to the oral cavity. A drop in the pressure is detected as distal implant end 38 forms an opening through the top of ridge 100 to below a Schneiderian membrane 122, thereby bringing distal opening(s) 41 into fluid communication with a surface of the membrane facing ridge 100, as shown in FIG. 11B. Upon detection of the drop, the surgeon ceases screwing implant 30 to avoid perforating the membrane. Distal implant end 38 typically does not pass through the top of ridge 100, at least at this stage in the procedure.

The drop in pressure may be detected using a separate pressure gauge 124, for example for applications in which fluid source 54 comprises a manual syringe 126, as shown in FIG. 11B. Such a gauge may be coupled to supply tube 52, as shown in the figure, or directly to the syringe (configuration not shown), as is known in the art, e.g., the Viceroy™ Inflation Syringe (Merit Medical Systems, Inc., South Jordan, Utah). Alternatively, for applications in which fluid source 54 comprises a powered drug delivery device, the drop in pressure may be detected using a pressure gauge integrated into the drug delivery device, as is known in the art (configuration not shown). For some applications, system 20 comprises an output unit that generates an output notifying the surgeon of the drop in pressure. The output may include an audio or visual signal. Alternatively or additionally, system 20 may display an indication of a numerical value of the measured pressure.

In an alternative embodiment, manual syringe 126 comprises a loss-of-resistance (LOR) syringe, such as known in the epidural art for locating the epidural space. The surgeon detects the drop in pressure by detecting a loss of resistance as distal implant end 38 forms an opening through the top of ridge 100 to below a Schneiderian membrane 122. For example, the Episure AutoDetect LOR Syringe (Indigo Orb, Inc., Irvine, Calif., USA) may be used.

Alternatively, instead of providing and measuring a pressure of a fluid, after the initial insertion of the implant into the bore, the surgeon uses a periapical radiograph to estimate remaining distance from implant tip to the sinus floor. The surgeon rotates the implant to penetrate into the sinus, such as by rotating the implant by a number of rotations equal to the remaining distance divided by a constant, e.g., 1.2 mm. Typically, the surgeon performs an additional periapical radiograph to ensure that the implant has penetrated into the sinus cavity.

Figure 11C:
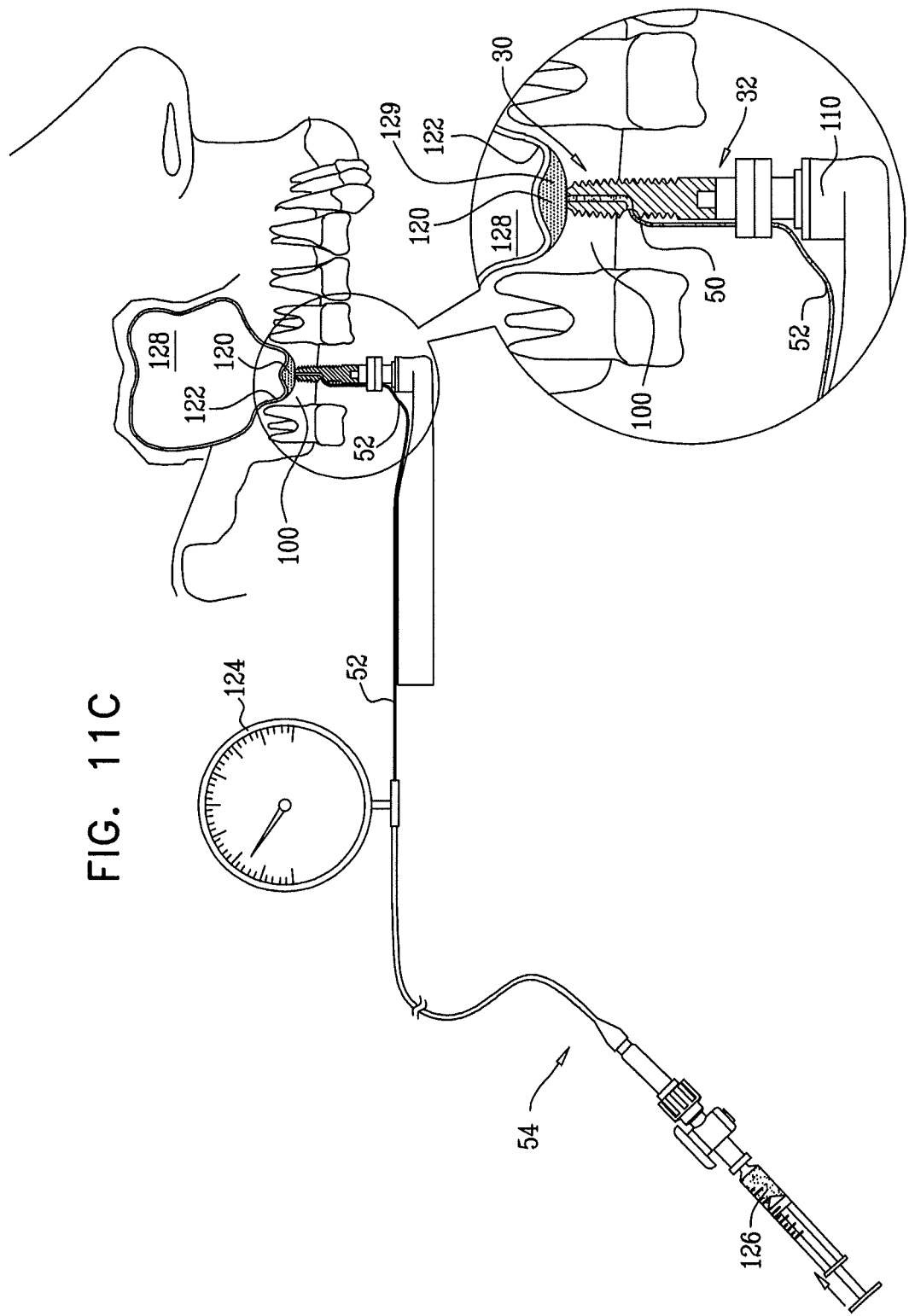

As shown in FIG. 11C, the surgeon gently lifts and separates membrane 122 from the top of ridge 100 into a maxillary sinus 128, by injecting a fluid 129, such as a biocompatible solution such as normal saline solution or a gas, from fluid source 54 under controlled pressure via supply tube 52, delivery tube 50, and lumen 40, so as to form a cavity 120 under the membrane between the ridge and the membrane (in FIG. 11C, the membrane is shown partially raised). System 20 generates an output indicative of a numerical value of the measured pressure, and/or a warning output if the measured pressure crosses a threshold value. An increase in the pressure generally indicates that the membrane is expanding and may perforate. Typically, the surgeon injects sufficient fluid 129 into cavity 120 to inflate the cavity to a vertical height of between about 2 and about 20 mm from the top of ridge 100, such as between about 2 and about 11 mm, e.g., between about 2 and about 8 mm. For some applications, a measured volume of fluid 129 is injected in order to achieve the desired cavity height, such as between about 0.5 and about 6 ml of fluid, e.g., between about 1 and about 4 ml, or between about 2 and about 4 ml.

Figure 11D:
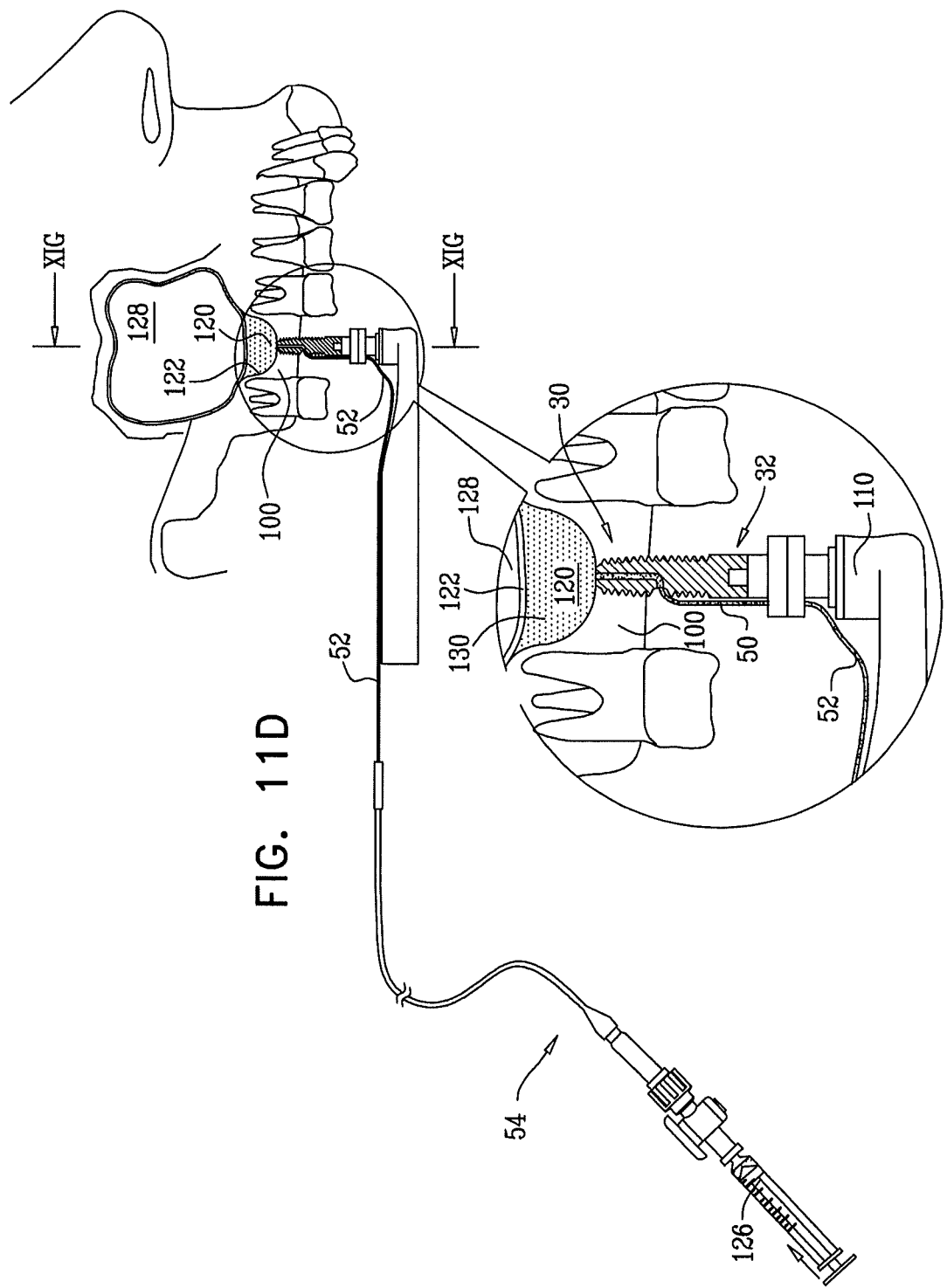

The fluid is typically drained from the cavity, and the surgeon injects a regenerative material 130, such as liquid or gel bone graft, into cavity 120, as shown in FIG. 11D. Fluid source 54 or a separate syringe or powered drug delivery device is used for injecting the regenerative material. If a separate syringe or device is used to inject the material, the material may be provided via supply tube 52, or via a separate supply tube coupled to proximal joint portion 60 of swivel joint 64, or coupled to supply tube 52 near the applicator. Alternatively, the material may be directly injected into lumen 40 by directly coupling the syringe to the implant. Regenerative material 130 may comprise an allograph, an autogeneous bone graft, or a xenograft, and may, for example, comprise a natural material, a synthetic material, or a mixture thereof. For example, regenerative material 130 may comprise one of the following commercially available fluid bone graft materials: DBX Paste (MTF), Allomatrix (Wright), Cerament (Bone Support), DynaGraft (C itagenix/ISOTIS), Fisiograft (Ghimas), Grafton (Osteotech), Optium DBM Gel (Lifenet/Depuy J&J), OsteoMax (Orthfix), PD VitalOs Cemen (VitalOs), or Regenafil® (Exactech). Alternatively, regenerative material 130 may comprise the composition described hereinbelow that comprises saline solution mixed with solid bone graft particles. Optionally, the system monitors and generates an output indicative of the pressure of the regenerative material as it is injected.

For some applications, system 20 measures the volume of fluid 129 injected into the cavity between the ridge and the membrane while forming cavity 120, at the step of the procedure described hereinabove with reference to FIG. 11C. Responsively to the measured volume, the surgeon determines an amount of regenerative material 130 to inject into cavity 120 at the step of the procedure described hereinabove with reference to FIG. 11D. Typically, the amount of regenerative material 130 is approximately equal to the volume of injected fluid 129, or slightly greater or less than the volume of the injected fluid. As a result, waste of regenerative material 130 is generally minimized, and the likelihood of perforating the membrane by injection of the regenerative material is generally reduced.

For some applications, the surgeon uses a flexible wire as a piston to help push the regenerative material through the supply tubes and/or lumen. This technique may be helpful when the regenerative material is viscous and thus difficult to inject using an ordinary syringe.

Alternatively, the surgeon injects regenerative material 130, rather than fluid 129, to lift membrane 122, thereby combining the steps of the procedure described hereinabove with reference to FIGS. 11C and 11D. In this case, the regenerative material typically comprises a liquid.

The surgeon decouples delivery tube 50 from implant 30, and further advances (e.g., by rotating or screwing) implant 30 into regenerative material 130 in cavity 120, as shown in FIG. 11E. The surgeon may decouple the delivery tube before or while further advancing the implant, and/or by advancing the implant until the tube becomes decoupled because of the rotation. For some applications, the surgeon decouples the delivery tube using the tools and techniques described hereinbelow with reference to FIGS. 12A and 12B. This additional advancing of the implant advances lateral surface 42 of implant 30 at least until lateral opening 44 is positioned entirely within the bore in ridge 100 and/or in regenerative material 130 in cavity 120. Such positioning of both ends of lumen 40 within bone substantially reduces the risk of infection, because proximal end 34 of implant 30 that is exposed to the oral cavity or gingiva is permanently closed. The surgeon decouples applicator 32 from implant 30, such as by pulling the male coupling element out of the female coupling element, or using the tool and techniques described hereinbelow with reference to FIG. 12C-E. Typically, the surgeon couples a cover screw to the proximal end of the implant using a hand driver, and sutures the gingiva.

As shown in FIG. 11F, after bone grows into regenerative material 130 and is integrated into ridge 100, an appliance 140, such as a crown, is coupled to implant 30, typically using an abutment 142 coupled to implant 30, as is known in the art. Alternatively, as mentioned above, implant 30 comprises a single-stage transgingival implant/abutment, as is known in the art.

Figure 11H:
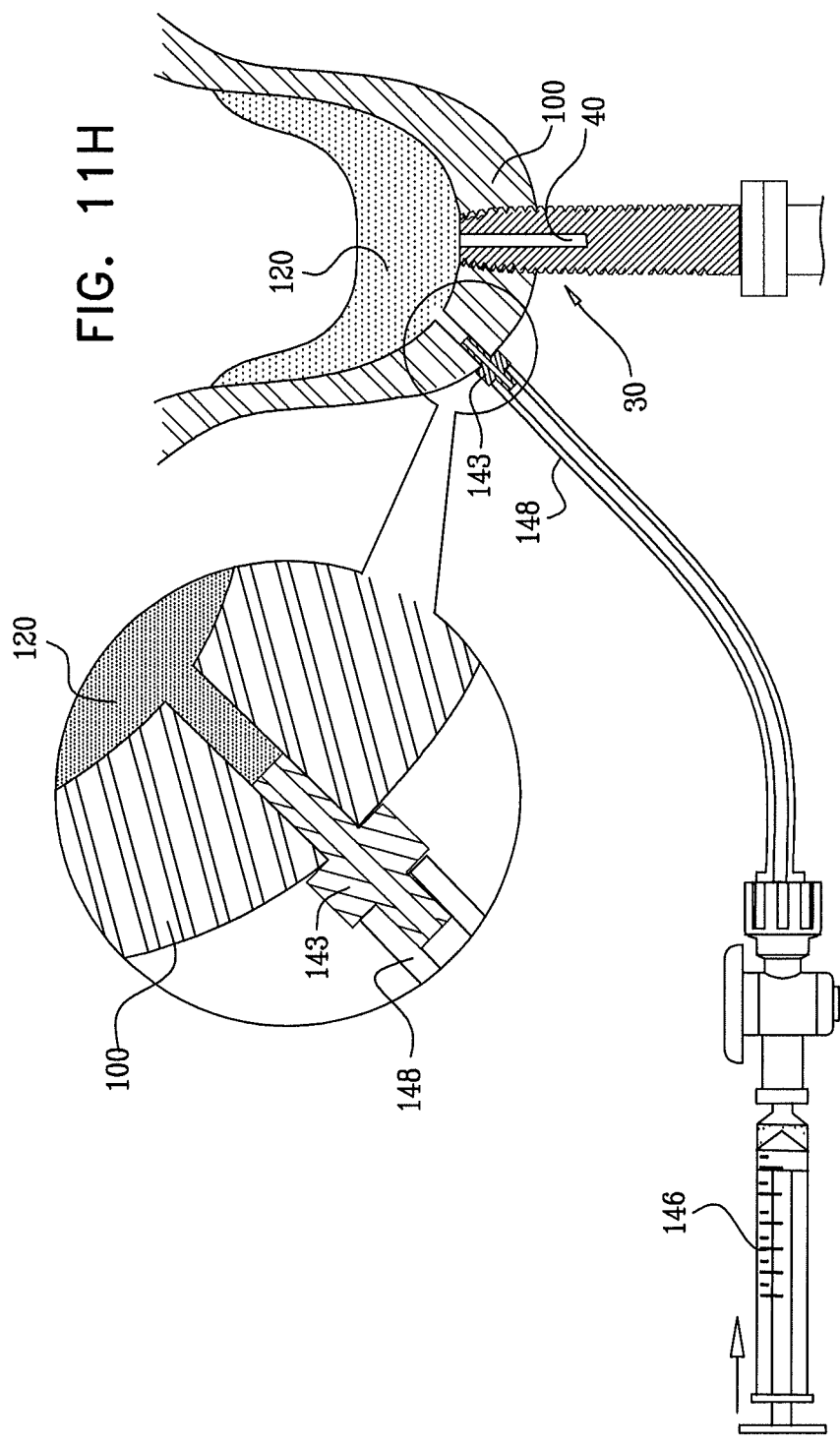
Figure 11I:
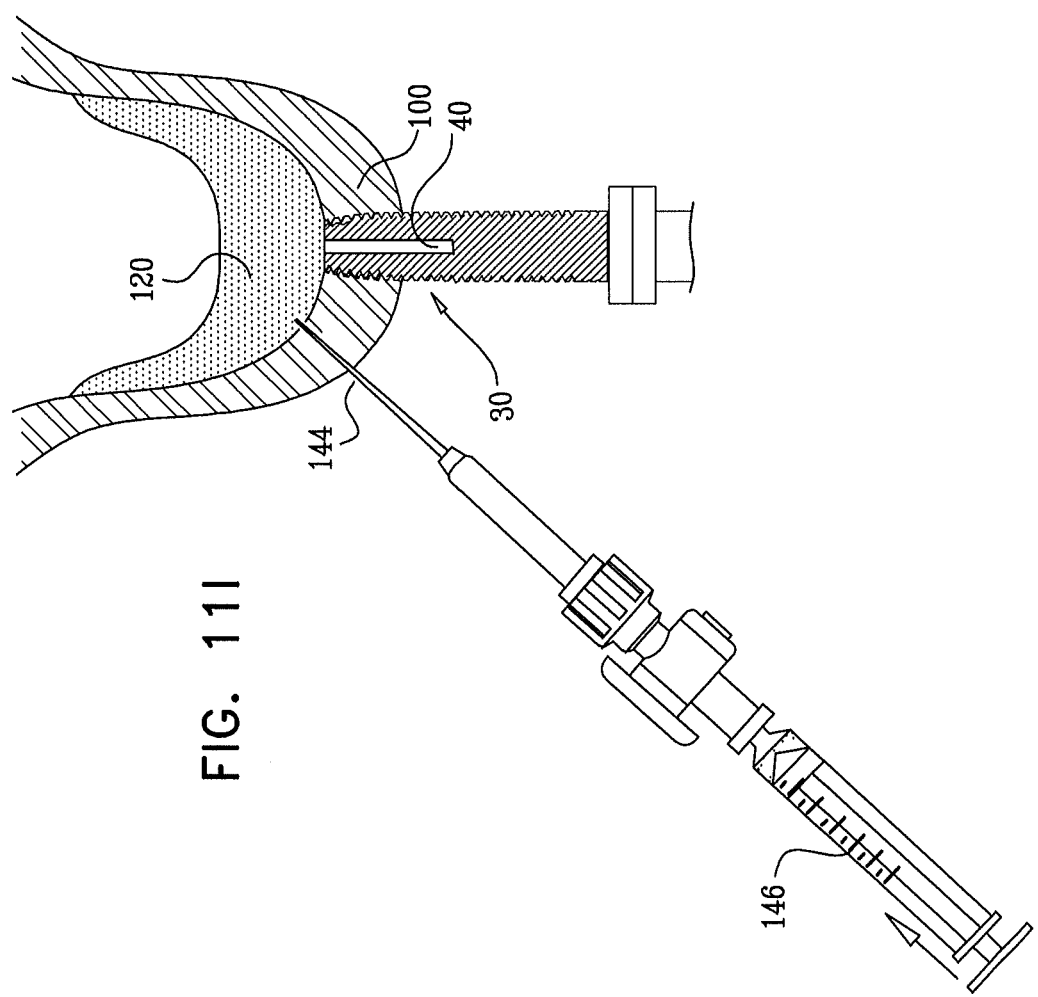

Reference is made to FIGS. 11G-I, which are schematic cross-sectional illustrations of alternative techniques for injecting regenerative material 130, taken along line XIG-XIG of FIG. 11D, in accordance with respective embodiments of the present invention. These techniques are used instead of or in addition to the injection technique described hereinabove with reference to FIG. 11D. In these techniques, after membrane 122 has been lifted from the top of ridge 100, as described hereinabove with reference to FIG. 11C, the surgeon forms a second bore through the ridge at a second bore location, e.g., using a dental drill. The second bore location is typically at least 1 mm, such as at least 2 mm or at least 3 mm, from a first bore location of the bore described hereinabove with reference to FIG. 11C. The surgeon injects regenerative material 130 into cavity 120, typically using a separate syringe 146 or powered drug delivery device, via a supply line 148.

For some applications, as shown in FIGS. 11G and 11H, the surgeon injects the regenerative material by inserting an adaptor 143 into the second bore. The adaptor is shaped so as to define a channel therethrough. Supply line 148 is coupled to the proximal end of the channel. For example, adaptor 143 may be threaded, as shown in FIG. 11G, in which case the surgeon screws the adaptor into the second bore. In this configuration, adaptor 143 is typically rigid, and may comprise a metal. Alternatively, the adaptor may not be threaded, as shown in FIG. 11H, in which case the surgeon presses the adaptor into the second bore. In this configuration, the adaptor may be rigid (e.g., may comprise a metal) or flexible (e.g., may comprise rubber). Optionally, the adaptor is conical.

For other applications, the surgeon injects the regenerative material using a needle 144, as shown in FIG. 11I. The surgeon may form the second bore using a dental drill, or form the second bore directly using the needle. For still other applications, the surgeon injects the material through a channel of a drill bit, such as described herein with reference to FIG. 4 or 20.

Insertion of the regenerative material through a separate bore allows the use of an implant having a narrower lumen 40 and/or delivery tube 50, because the lumen and delivery tube need only allow passage of the fluid as described hereinabove with reference to FIG. 11C, and not the regenerative material, which is generally more viscous than the fluid.

In an embodiment of the present invention, one of dental drills 300 or 820, described hereinbelow with reference to FIG. 14 or 20, respectively, is used to perform the sinus lift through a first bore, rather than implant 30. Alternatively, the sinus lift is performed using a conventional surgical drill with irrigation, such as internal irrigation, as is known in the art and commercially available. The regenerative material is injected through a second bore, as described hereinabove with reference to FIGS. 11G-I. In addition to allowing the use of a narrower lumen through the drill bit, insertion of the regenerative material through a separate bore allows the use of a narrower drill bit for performing the sinus lift through the first bore.

In an embodiment of the present invention, liquid osteotome 1230, described hereinbelow with reference to FIGS. 24A-C and 25, or FIGS. 26 and 27A-B, is used to perform the sinus lift through a first bore, rather than implant 30. The regenerative material is injected through a second bore, as described hereinabove with reference to FIGS. 11G-I. In addition to allowing the use of a narrower lumen through the osteotome, insertion of the regenerative material through a separate bore allows the use of a narrower osteotome for performing the sinus lift through the first bore.

Reference is made to FIGS. 12A and 12B, which are schematic illustrations of tools and techniques, respectively, for decoupling delivery tube 50 from implant 30, in accordance with an embodiment of the present invention. These tools and techniques are particularly useful for the configuration of delivery tube 50, implant 30, and applicator 32 described hereinabove with reference to FIGS. 3A-D, 4A-B, 5, and 6.

FIG. 12A shows a stabilization tool 150 and a driver tool 160. A distal end of the stabilization tool is shaped so as to define a coupling opening 152, having, for example, an internal hex width of 6.35 mm. Driver tool 160 may be a conventional hand driver having a hex width of 2.4 mm, for example. In an embodiment of the present invention, driver tool 160 is coupled to stabilization tool 150 within coupling opening 152, such that the driver tool is rotatable with respect to the distal end of the stabilization tool.

As shown in FIG. 12B, the surgeon stabilizes applicator 32 by coupling stabilization tool 150 to the proximal end of the applicator. Applicator 32, as shown hereinabove in FIGS. 3A-D and 4A-B, comprises an applicator body, which comprises rotatable surface 92 accessible from the proximal end of the applicator. Applicator 32 is also shaped so as to define a stabilization surface 154 accessible from the proximal end of the applicator. Application of a stabilizing force to stabilization surface 154 stabilizes the implant during rotation of rotatable surface 92. As a result, the decoupling of delivery tube 50 from implant 30 does not dislodge or misalign the implant, which has been precisely placed in a bore in the ridge, as described hereinabove with reference to FIG. 11B. Furthermore, application of the stabilizing force reduces or prevents the transfer of force to the bone from tools operating on the applicator and/or implant.

The outer diameter (or width, such as if the surface is hexagonal) of the stabilizing surface is approximately equal to the internal diameter (or width) of coupling opening 152 of stabilization tool 150, and the stabilizing surface and coupling opening have corresponding shapes.

The surgeon positions stabilization tool 150 such that coupling opening 152 is removably coupled to stabilization surface 154, and applies the stabilizing force to stabilization surface 154. For example, both the coupling opening and the stabilization surface may be hexagonal. Typically, rotatable surface 92 and stabilization surface 154 are configured to facilitate on-axis rotation of the rotatable surface, thereby minimizing any off-axis force that the rotation may cause the apparatus to apply to its surroundings.

In order to decouple delivery tube 50 from implant 30 by breaking thinner portion 72 of the delivery tube, while the stabilization tool stabilizes the applicator, the surgeon removably couples a driver tool 160 to rotatable surface 92 of applicator 32 through opening 152 of stabilization tool 150, and rotates the driver tool, thereby rotating the rotatable surface and breaking thinner portion 72, as described hereinabove with reference to FIGS. 3A-D, 4A-B, 5, and 6. For example, driver tool 160 may be a conventional dental hand driver having a hex width of 2.4 mm.

Reference is made to FIGS. 12C and 12D-E, which are schematic illustrations of a tool and techniques for decoupling applicator 32 from implant 30, respectively, in accordance with an embodiment of the present invention. This tool and these techniques are particularly useful for the configuration of delivery tube 50, implant 30, and applicator 32 described hereinabove with reference to FIGS. 3A-D, 4A-B, 5, and 6.

FIG. 12C shows a driver tool 162, such as a conventional hand driver having a hex width of 1.25 mm, for example.

As shown in FIG. 12D, the surgeon decouples applicator 32 from implant 30 by inserting driver tool 162 into the head of connecting screw 98, described hereinabove with reference to FIGS. 3A-D, 4A-B, 5, and 6. The surgeon rotates driver tool 162 (typically counterclockwise) to unscrew connecting screw 98, thereby decoupling applicator 32 from implant 30. Typically, stabilizing tool 150 remains coupled to stabilization surface 154 of implant 30 during this decoupling. FIG. 12E shows the applicator after it has been decoupled from the implant, leaving the implant in place in the ridge.

Figure 13A:
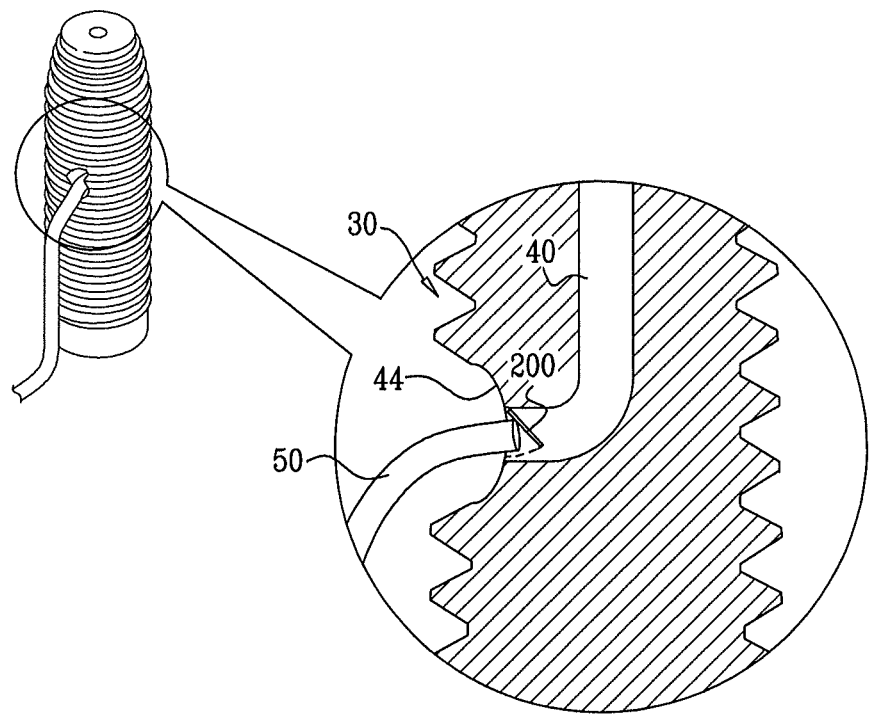
FIGS. 13A and 13B are schematic illustrations of respective configurations of the dental implant of FIG. 1 in which the implant comprises a valve, in accordance with respective embodiments of the present invention.
Figure 13B:
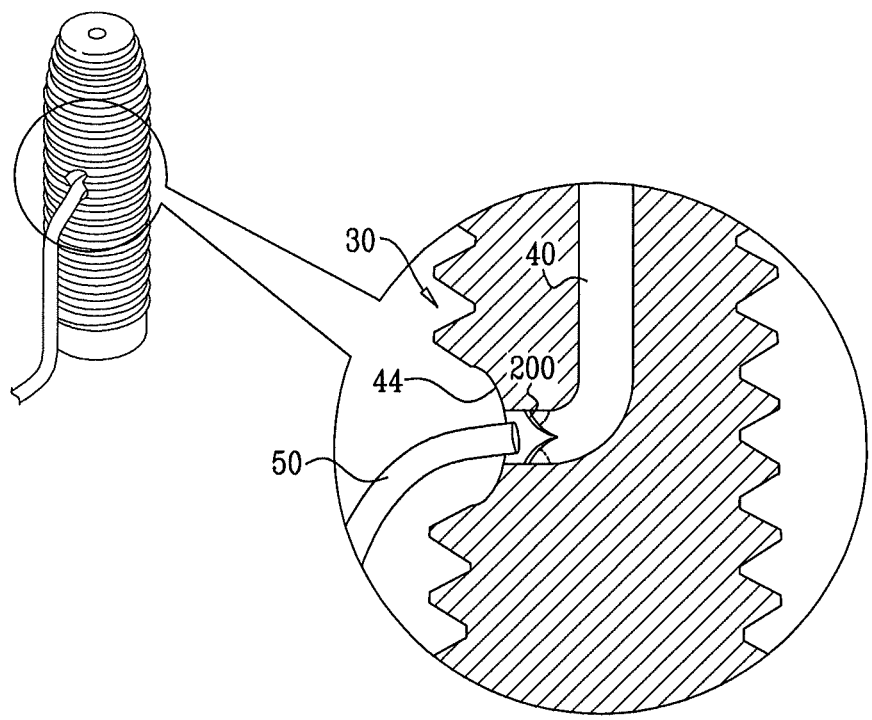

Reference is made to FIGS. 13A and 13B, which are schematic illustrations of respective configurations of dental implant 30 in which the implant comprises a valve 200, in accordance with respective embodiments of the present invention. In the configuration shown in FIG. 13A, valve 200 comprises a trap door valve positioned in a fluid path defined by lumen 40 near lateral opening 44. In the configuration shown in FIG. 13B, valve 200 is arranged in a fluid path defined by lumen 40. Alternatively, the valve may be arranged in delivery tube 50 (configuration not shown).

For some applications, valve 200 comprises a unidirectional valve that is configured to allow passage of material through lumen 40 or delivery tube 50 toward distal implant end 38, and to prevent the passage in an opposite direction. For these applications, valve 200 may be positioned at (a) any convenient location along lumen 40, as shown in FIG. 13A, such as in a vicinity of lateral opening 44, in a vicinity of a distal opening of the lumen, or at an intermediary location in the lumen, or (b) any convenient location along delivery tube 50 (configuration not shown).

For other applications, valve 200 is configured to allow bidirectional flow through lumen 40. For these applications, the valve may be positioned in a vicinity of lateral opening 44, and may comprise, for example, a trap door valve, a faucet valve, a duckbill check valve (e.g., comprising a biodegradable material), or a magnetic valve. The valve may comprise metal or silicone, or another biocompatible material. For some applications, the valve is configured to be opened by delivery tube 50 when the tube is coupled to implant 30, and to assume a closed position when the delivery tube is not coupled to the implant. The valve is opened during injection and drainage of fluid 129 (e.g., a biocompatible solution such as normal saline solution), as described hereinabove with reference to FIGS. 11C and 11D. For example, if the valve comprises a trap door, the trap door may be forced open by delivery tube 50. Regenerative material 130 is injected while the valve remains open, as described hereinabove with reference to FIG. 11D, and thereafter the valve is closed. For applications in which the valve comprises a trap door, the trap door may be closed by removing delivery tube 50.

For some applications, valve 200 serves to prevent regenerative material 130 from exiting cavity 120 once the material has been injected into the cavity, as described hereinabove with reference to FIG. 11D. For some applications, the sinus lift is performed by injecting fluid 129 (e.g., a biocompatible solution such as normal saline solution) using a separate dental sleeve. After cavity 120 has been formed between ridge 100 and membrane 122, the sleeve is removed, implant 130 is inserted, and regenerative material 130 is injected into the cavity via the implant.

For some applications, valve 200 is configured to be opened and closed using an open/close control accessible from outside of the implant. For example, the open/close control may comprise a thin rod that passes through the lateral surface of the implant. One end of the rod is accessible from the lateral surface, and is shaped so as to define a male or female coupling element, e.g., a hexagonal socket or a screw slot. The other end of the rod comprises an opening/closing element positioned within lumen 40. The opening/closing element is configured to block passage through the lumen when the rod is rotated in a first set of one or more rotational positions, and to allow passage through the lumen when the rod is rotated in a second set of one or more rotational positions.

Figure 14:
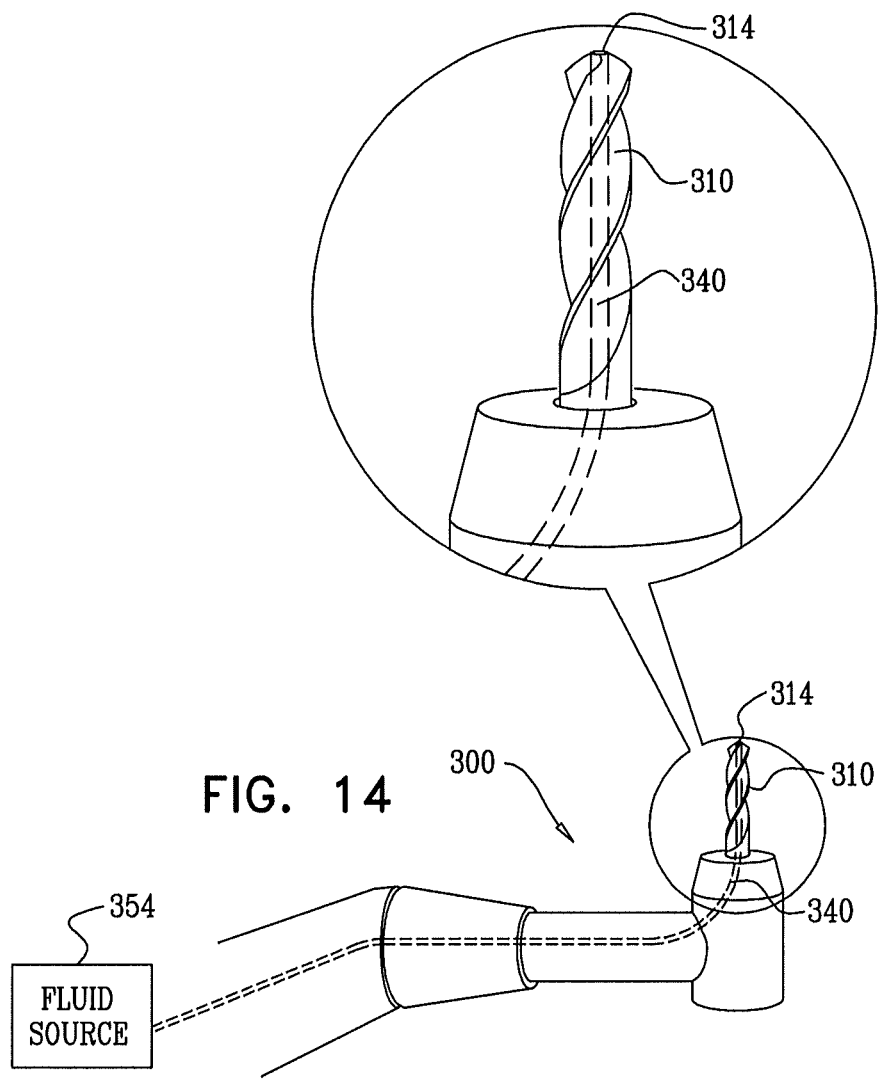
FIG. 14 is a schematic illustration of a dental drill, in accordance with an embodiment of the present invention.

Reference is made to FIG. 14, which is a schematic illustration of a dental drill 300, in accordance with an embodiment of the present invention. Drill 300 comprises a bit 310 which is shaped so as to define a lumen 340 therethrough that is open to a distal portion of the bit that extends from a distal end 314 of the bit along up to 8 mm of a longitudinal length of the bit, such as up to 6 mm of the length, up to 4 mm of the length, or up to 2 mm of the length. For some applications, lumen 340 is open to distal end 314 of the bit, either at the tip of the bit or in the general area of the distal end of the bit. The surgeon uses drill 300 to perform a sinus lift procedure (e.g., a controlled sinus lift procedure, such as described hereinabove with reference to FIGS. 11A-D), a lateral ridge augmentation (such as described hereinbelow with reference to FIGS. 22A-F or FIGS. 23A-F), or another dental procedure. Drill 300 is coupled to a source of pressure 354. While the surgeon drills a bore through the maxillary alveolar ridge, fluid source 354 provides a fluid under monitored pressure to the distal bit portion, such as distal bit end 314, via lumen 340. The fluid typically comprises a biocompatible solution such as normal saline solution, or a gas, e.g., air.

Bit 310 functions as a cork that isolates the distal end of the bore from the oral cavity, allowing the development of relatively high pressure in the fluid, as described hereinabove. Alternatively, an o-ring is provided around the bit to provide a seal. A drop in the pressure is detected as distal bit end 314 forms an opening through the top of ridge 100 to below a Schneiderian membrane (similar to the step of the earlier described procedure shown in FIG. 11B), thereby bringing the distal opening into fluid communication with a surface of the membrane facing the ridge. Upon detection of the pressure drop, the surgeon ceases drilling to avoid perforating the membrane. For some applications, the drill automatically ceases drilling upon detecting the drop in pressure, while for other applications, the drill generates an output notifying the surgeon of the drop in pressure. The output may include an audio or visual signal. Alternatively or additionally, the drill may display an indication of a numerical value of the measured pressure.

After penetrating the ridge, the surgeon performs a sinus lift, either using techniques described herein (such as injecting a fluid under controlled pressure), or using techniques known in the art. For some applications, the surgeon inserts dental implant 30 into the bore, which is not necessarily provided with swivel joint 64. For other applications, the surgeon inserts a conventional dental implant into the bore.

In an embodiment of the present invention, this controlled pressure-based penetration is performed using an osteotome, rather than bit 310. For example, the osteotome may comprise osteotome 1230, described hereinbelow with reference to FIGS. 24A-C and 25, or osteotome 1330, described hereinbelow with reference to FIGS. 26 and 27A-B.

Figure 15:
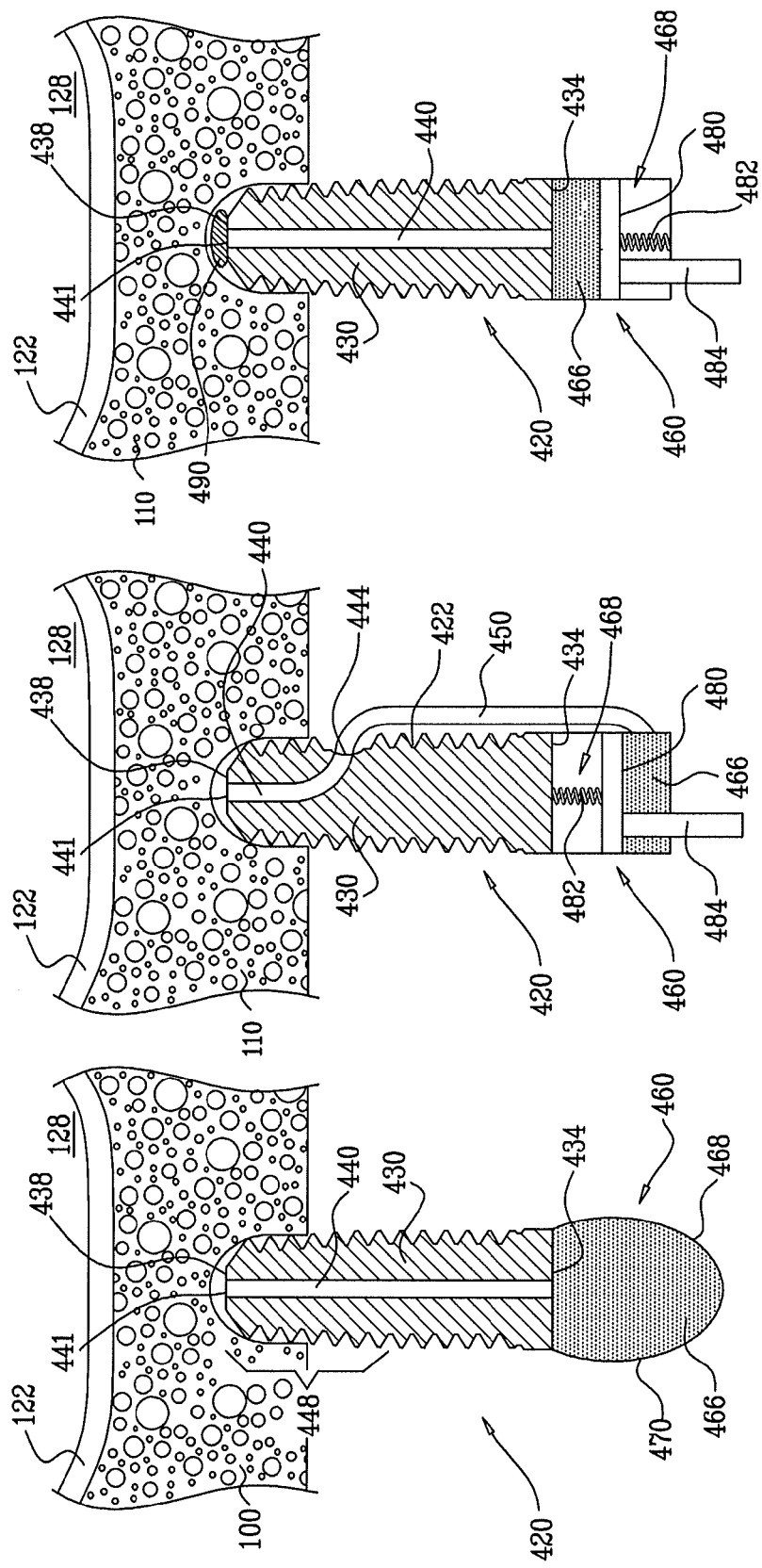
FIGS. 15A-C are schematic illustrations of configurations of another dental implant system, in accordance with respective embodiments of the present invention.

Reference is made to FIGS. 15A-C, which are schematic illustrations of configurations of a dental implant system 420, in accordance with respective embodiments of the present invention. System 420 comprises a dental implant 430, which is shaped so as to define a lumen 440 therethrough having at least one distal opening 441 through a distal external surface of a distal portion 448 of the implant that extends from a distal implant end 438 of the implant along up to 50% of a longitudinal length of the implant, such as up to 30% of the length, up to 15% of the length, or up to 5% of the length. For some applications, distal portion 448 has a longitudinal length of up to 8 mm, such as up to 6 mm, up to 4 mm, or up to 2 mm. Distal opening 441 may be located at distal implant end 438, such as centered on the distal implant end, e.g., at a distal tip of distal implant end 438, or not centered on the distal implant end (and thus located at a location other than the distal tip), such as described hereinabove with reference to FIG. 2A. Alternatively, distal opening(s) 441 may be located at one or more locations along distal implant portion 448, including at locations on a lateral surface of the implant.

System 420 further comprises an applicator 460 that is removably coupled to a proximal end 434 of implant 430 during a portion of an implantation procedure. The applicator comprises a chamber 466 that is in fluid communication with lumen 440, and an elastic pressure-applying element 468 that is configured to apply pressure to the chamber. While the surgeon screws the implant into the alveolar ridge, pressure is applied by fluid in chamber 466 to distal implant end 438 via lumen 440. A drop in the pressure is detected as the distal implant end forms an opening through the top of the ridge to below a Schneiderian membrane, thereby bringing the distal opening into fluid communication with a surface of the membrane facing the ridge. Upon detection of the pressure drop, the surgeon ceases to screw the implant. Although the entire applicator, including the entire pressure-applying element, is shown in FIGS. 15A-C as being sized to be positioned within an oral cavity of the subject, for some applications a portion of the applicator, such as a portion of the pressure-applying element, is configured to be positioned outside of the oral cavity. For example, all or part of the pressure-applying element may be in fluid communication with the applicator via one or more tubes (configuration not shown).

In the configuration shown in FIG. 15A, elastic pressure-applying element 468 comprises a balloon 470 shaped so as to define chamber 466. For some applications, the pressure is applied by initially inflating balloon 470 with fluid to greater than atmospheric pressure. Alternatively or additionally, the pressure is applied by the surgeon squeezing the balloon in conjunction with screwing the implant.

In the configurations shown in FIGS. 15B and 15C, applicator 460 comprises a piston 480 and a spring 482 configured to apply pressure to chamber 466. In the configuration shown in FIG. 15B, the spring, piston, and chamber are arranged such that the spring applies pressure in a proximal direction on the piston, and the chamber is positioned proximal to the piston. In this configuration, the chamber is typically in fluid communication with lumen 440 via a delivery tube 450, a distal end of which is removably coupled to lumen 440 via a lateral opening 444 in an external lateral surface 442 of implant 430, and a proximal end of which is coupled to the chamber.

In the configuration shown in FIG. 15C, the spring, piston, and chamber are arranged such that the spring applies pressure in a distal direction on the piston, and the chamber is positioned distal to the piston. In this communication, a proximal end of lumen 440 is typically open to the chamber at proximal end 434 of the implant via a proximal opening, and the chamber is in fluid communication with lumen 440 via the proximal opening.

For some applications, the chamber contains a fluid, and the applicator comprises an indicator element 484 that is arranged with the piston to indicate when the pressure applied to the chamber has caused ejection of at least a portion of the fluid from the chamber out of distal implant end 438 via lumen 440. For example, in the configuration shown in FIG. 15B, movement of piston 480 in a proximal direction causes indicator element 484 to protrude from a proximal end of applicator 460, and in the configuration shown in FIG. 15C, movement of the piston in a distal direction causes the indicator element to retract into the proximal end of the applicator.

For some applications, as illustrated in FIG. 15C (but equally applicable to the embodiments described with reference to FIGS. 15A and 15B), implant 430 comprises a plug 490 removably coupled to the implant so as to seal the distal end of lumen 440. The plug is typically biodegradable. The plug comes loose during the implantation procedure by friction generated by the screwing of the implant, allowing the fluid to escape from the chamber as the distal implant end forms an opening through the top of the ridge into the cavity. For some applications, the plug comprises regenerative material, such as bone graft.

For some applications, the techniques described with reference to FIGS. 15A-C are practiced in combination with those described hereinabove with reference to FIGS. 1, 2A-C, 11A-F, and/or 13A-B. By way of example and not limitation, implant 430 may comprise a self-tapping implant having a cutting surface, such as a screw thread.

Figure 16:
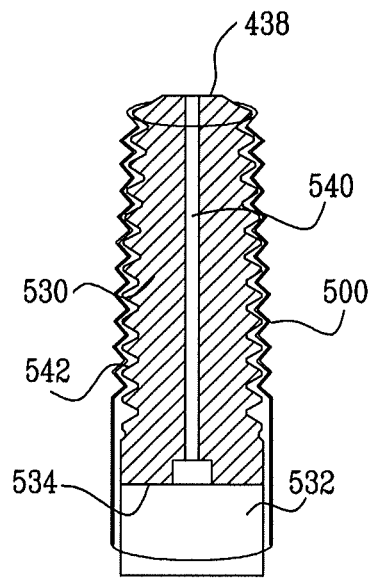
FIG. 16 is a schematic illustration of a removable sheath applied to a dental implant, in accordance with an embodiment of the present invention.

Reference is made to FIG. 16, which is a schematic illustration of a removable sheath 500 applied to a dental implant 530, in accordance with an embodiment of the present invention. Prior to performance of an implantation procedure, sheath 500 is placed on the implant such that the sheath covers at least a portion, e.g., substantially all, of a lateral external surface 542 of the implant, and, optionally, at least a portion of an applicator 532 coupled to the implant, and such that at least a portion of a distal end 438 of the implant is exposed. For some applications, a ring-shaped distal opening of the sheath is somewhat rigid in order to main the shape of a distal opening of the sheath. For some applications, a proximal opening of the sheath is elastic in order to tightly couple the sheath to applicator 532. Alternatively, sheath 500 is placed on the implant such that the sheath covers at least a portion (e.g., all) of a proximal end 534 of the implant. For some applications of this configuration, applicator 532 is not provided, while for other applications, the applicator is coupled to the proximal end of the implant such that the sheath is held between the proximal end of the implant and a distal end of the applicator. Upon decoupling the applicator from the implant, the sheath is no longer held in place.

During the implantation procedure, the surgeon inserts the implant into an alveolar ridge, such as a maxillary or mandibular alveolar ridge. The surgeon inhibits infection by removing the sheath from the implant in conjunction with the inserting.

For some applications, the techniques described with reference to FIG. 16 are practiced in combination with those described hereinabove with reference to FIGS. 1, 2A-C, 11A-F, 13A-B, and/or 15A-C. By way of example and not limitation, implant 430 may comprise a self-tapping implant having a cutting surface, such as a screw thread, and/or may be shaped so as to define a lumen 540 therethrough that is open through a distal opening to a distal portion of the implant, such as distal implant end 438.

Figure 17A:
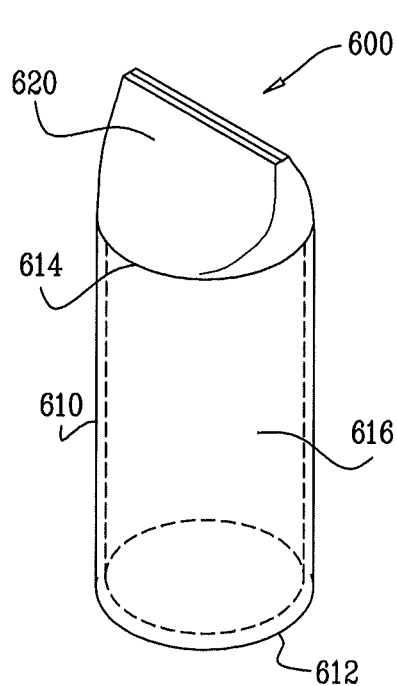
FIGS. 17A and 17B are schematic illustrations of a biodegradable dental sleeve in closed and open positions, respectively, in accordance with an embodiment of the present invention.
Figure 17B:
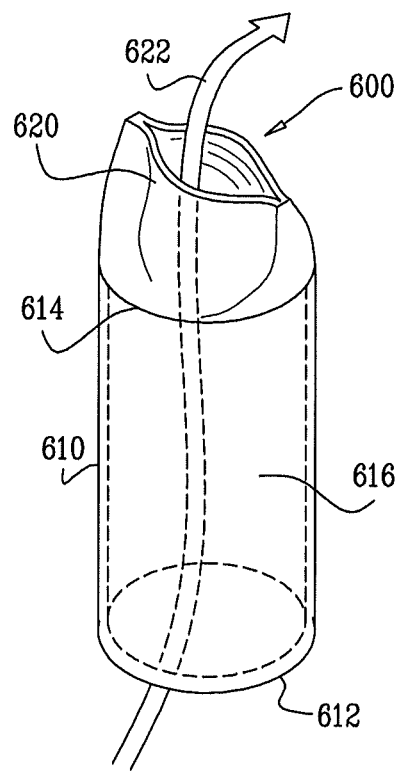

Reference is made to FIGS. 17A and 17B, which are schematic illustrations of a biodegradable dental sleeve 600 in closed and open positions, respectively, in accordance with an embodiment of the present invention. Dental sleeve 600 is configured to be inserted into a bore formed through a portion of a maxillary alveolar ridge, as described below, or through another bone, such as a mandibular alveolar ridge. The sleeve comprises a tubular portion 610 having proximal and distal ends 612 and 614, and shaped so as to define a lumen 616 therethrough. The tubular portion may be generally cylindrical, tapered, or conic in shape, and/or may have another shapes, e.g., may be hexagonal in cross-section. The sleeve further comprises a biodegradable valve 620 coupled to distal end 614 of tubular portion 610, and configured to allow flow through the lumen in a direction from proximal end 612 to distal end 614, as indicated schematically by an arrow 622 in FIG. 17B, and to prevent flow in the opposite direction by closing, as shown in FIG. 17A. Tubular portion 610 and valve 620 typically comprise a flexible material, such as collagen, polylactic acid, or polyglycolic acid. For some applications, valve 620 comprises a flexible duckbill check valve, as is known in the art.

During a surgical procedure to implant a dental implant (the implant is not shown in FIGS. 17A-B), a surgeon forms a bore in the maxillary alveolar ridge, and lifts the Schneiderian membrane to form a cavity under the membrane between the ridge and the membrane, such as using techniques described herein or known in the art. After lifting the membrane, the surgeon inserts sleeve 600 into the bore, and injects a regenerative material into the cavity (such as described hereinabove, e.g., a liquid regenerative material) through lumen 616 and valve 620. Valve 620 prevents the regenerative material from exiting the cavity. The surgeon mounts a dental implant, such as an implant described herein or known in the art, in the bore by rotating the implant until a distal portion thereof breaks through valve 620 into the cavity. At this stage of the procedure, the implant blocks exit of the regenerative material from the cavity. The surgeon leaves the valve in place in the bore to biodegrade, and be absorbed. Typically, tubular portion 610 is biodegradable, and is left in the bore along with valve 620. Alternatively, the tubular portion and the valve are configured to be readily separated from one another, and, after mounting the dental implant in the bore, the surgeon separates the tubular portion from the valve and withdraws the tubular portion from the bore.

Figure 18:
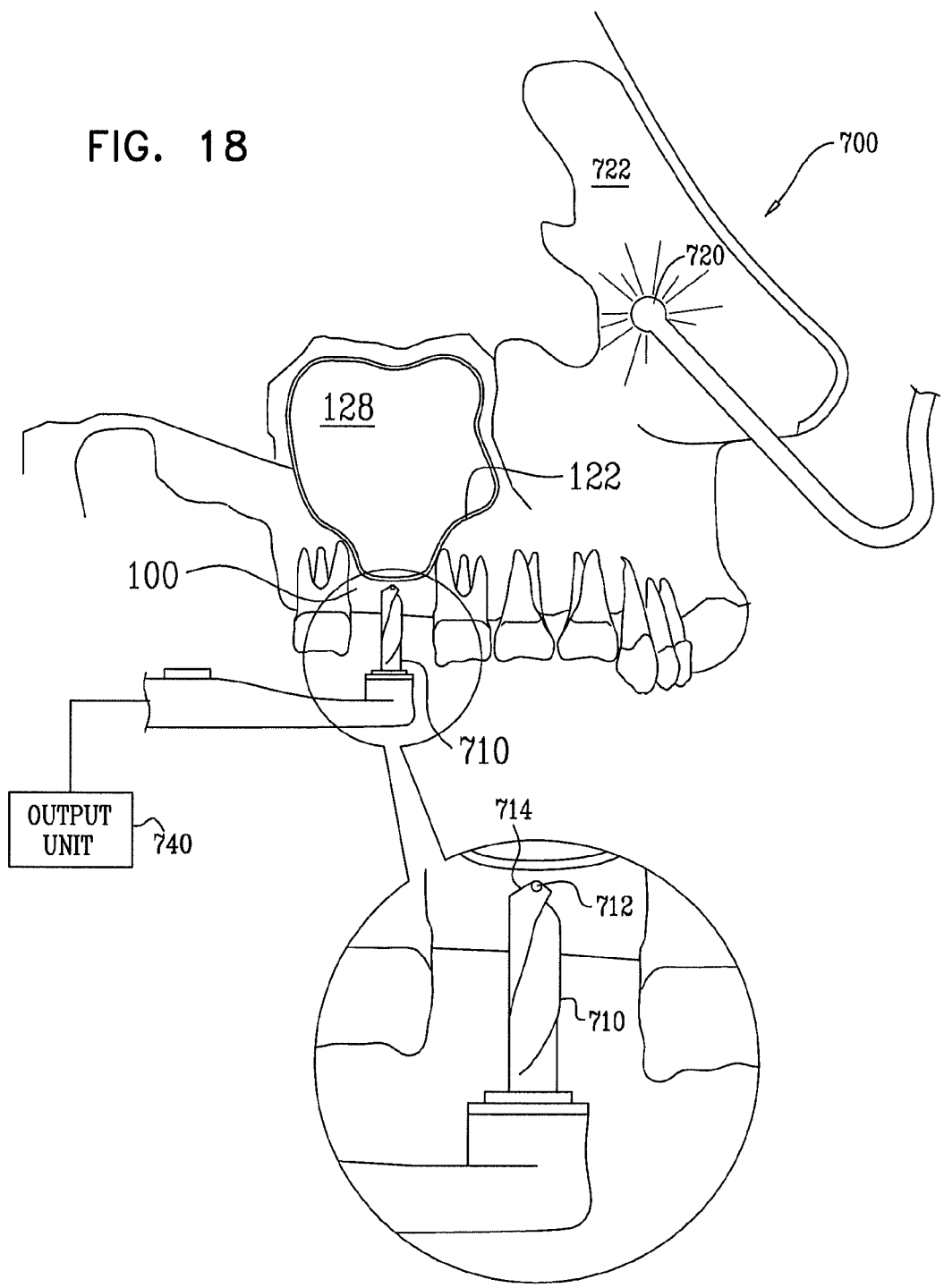
FIG. 18 is a schematic illustration a controlled bone penetration system, in accordance with an embodiment of the present invention.

Reference is made to FIG. 18, which is a schematic illustration of a controlled bone penetration system 700, in accordance with an embodiment of the present invention. System 700 comprises a drilling element 710, which may comprise, for example: (a) a dental drill bit, such as known in the art, or described hereinabove with reference to FIG. 14 (as shown in FIG. 18); (b) a dental implant, such as known in the art, or described hereinabove; or (c) a generally cylindrical sleeve, such as described, for example, in above-mentioned US Patent Application Publication 2006/0084034 to Hochman. System 700 further comprises a light sensor 712, which is configured to sense a level of illumination at a distal end 714 of drilling element 710, such as at a distal tip. Light sensor 712 comprises a light detecting element. For some applications, the light detecting element is positioned at distal end 714, as shown in the figure. For other applications, the light detecting element is positioned remotely from distal end 714, and is in optical communication with the distal end, such as via one or more fiber optic cables that pass through drilling element 710 (configuration not shown).

System 700 further comprises a light source 720, which is configured to be positioned so as to provide substantially more illumination in the vicinity of light sensor 712 when distal end 714 of drilling element 710 has penetrated through a bone, such as the maxillary alveolar ridge, than before the distal end penetrates the bone. For example, light source 720 may be positioned in a nasal cavity 722 of the subject or near the nasal cavity outside the body (e.g., on a cheek of the subject), such that light emitted by the light source into the nasal cavity illuminates an interior of a maxillary sinus 128 through the wall of the sinus and/or via an anatomical opening between sinus 128 and a middle nasal meatus of nasal cavity 722. Alternatively, the light source is positioned in the maxillary sinus (configuration not shown). Further alternatively, the light source is positioned in an oral cavity of the subject, and illuminates the maxillary sinus via the palate (configuration not shown).

Further alternatively, light source 720 is positioned adjacent to light sensor 712 on drilling element 710. The level of illumination sensed by light sensor 712 changes as the distal tip of the implant breaks through the bone. For some applications, the light source and/or the light sensor are positioned remotely from the distal end of drilling element 710, and are in optical communication with the distal end, such as via one or more fiber optic cables that pass through drilling element 710 (configuration not shown).

System 700 further comprises an output unit 740, which is configured to generate an output indicative of the illumination sensed by light sensor 712. For example, the output may indicate a level of the light detected, such as numerically or by a tone configured to indicate the level (e.g., by varying its pitch and/or volume), and/or to indicate when the detected level of illumination crosses a threshold level.

During an implantation procedure, the surgeon positions light source 720 at the desired location, and begins creating a bore in the maxillary alveolar ridge using drilling element 710. As distal end 714 and light sensor 712 approach the top of the ridge, the light sensor detects a rapid increase in the amount of light reaching the detector from light source 720. Typically, but not necessarily, the detected light varies as a sigma function with respect to the distance the distal implant travels. Responsively to this measurement of light intensity, the surgeon may decrease the rotational speed of the drill as the distal end approaches penetration out of the bone. When the distal end 714 forms an opening through the top of ridge 100 to below a Schneiderian membrane 122, the light sensor detects a substantial increase in illumination, and the surgeon ceases drilling.

In an embodiment of the present invention, light source 720 is configured to emit light from distal end 714 of drilling element 710, and light sensor 712 is positioned remotely from the distal end to detect the emitted light, such as in nasal cavity 722 or outside of the cavity, such as outside of a body of the subject. The light sensor, whether positioned in the cavity or not, is configured to sense a level of the emitted light within the cavity.

For some applications, system 700 is used for controlled penetration of another body structure, such as another bone, a brain, a spinal cord, a cyst, or another lesion in a bone. For example, the lesion may be in a body part in which the lesion has different optical properties from the native tissue. For some applications, the lesion is a vascular lesion, such as a vascular tumor.

For some applications, system 700 is used for controlled penetration of a tumor. Tumors often are optically distinct from surround tissue, such as because the tumors have greater blood supply than surrounding tissue, or different density than that of surrounding tissue (e.g., greater opacity than that of surrounding tissue). For some applications, light source 720 generates light at two different wavelengths, and the system analyzes the detected light at the two wavelengths to detect a level of blood supply, such as using techniques known in the pulse oximetry art. A greater level of blood indicates that the tool has penetrated into the tumor.

For some applications, system 700 is used for controlled penetration of a needle into a uterus during amniocentesis. The penetration is alternatively or additionally detected by detecting a change in pressure, using techniques described hereinabove. Similarly, system 700 and/or the pressure change detection techniques described herein may be used for detecting penetration of an epidural needle into the epidural space at the base of the spine.

In an embodiment of the present invention, the techniques described herein are used for performing nasal floor elevation, mutatis mutandis, in order to implant a dental implant in the incisor position. A bore is formed through a maxillary alveolar ridge in a region of the upper incisors from the front side, and the implant is inserted into the bore at least until the distal opening comes into fluid communication with a surface of a nasal floor membrane facing the ridge. The membrane is raised to form a cavity between the ridge and the membrane.

In an embodiment of the present invention, the techniques described herein are used with an inclined entry, for patients in which the residual bone of the maxillary alveolar ridge is too thin to achieve stability. A bore is formed with an inclined entry at a location adjacent the site of the implant where there is sufficient bone, and sinus lift is performed via the bore using the techniques described herein, mutatis mutandis, such as the techniques described hereinabove with reference to FIG. 14, or with reference to FIGS. 1, 2A-F, 3A-D, 4A-B, 5, 6, 7, 8, 9A-E, 10, 11A-F, 12A-B, 13A-B, 15A-C, 16, and/or 17A-B. For some applications, the bore is formed using a biodegradable drilling element that is configured to biodegrade as the regenerative material integrates with the native bone. Regenerative material is injected into the cavity between the ridge and the Schneiderian membrane. Prior to or after the material integrates, a second straight bore is made at the desired implant location through the thin preexisting bone and into the regenerative material or new bone, and a conventional implant is inserted into the bore.

In an embodiment of the present invention, the techniques described herein are used with a palatal entry. A bore is formed in the palate (which is thicker than the maxillary alveolar ridge), and sinus lift is performed via the bore using the techniques described herein, mutatis mutandis, such as the techniques described hereinabove with reference to FIG. 14, or with reference to FIGS. 1, 2A-F, 3A-D, 4A-B, 5, 6, 7, 8, 9A-E, 10, 11A-F, 12A-B, 13A-B, 15A-C, 16, and/or 17A-B. For some applications, the bore is formed using a biodegradable drilling element that is configured to biodegrade as the regenerative material integrates with the native bone. The drilling element is withdrawn or allowed to biodegrade. Regenerative material is injected into the cavity between the ridge and the Schneiderian membrane. Prior to or after the material integrates, a second bore is made at the desired implant location through the maxillary alveolar ridge and the new bone, and a conventional implant is inserted into the bore.

In an embodiment of the present invention, the regenerative material comprises a composition comprising solid bone graft particles mixed with a physiological solution, such as saline solution, blood, or diluted blood. For example, the solid bone graft particles may comprise freeze-dried bone allograft (FDBA). Typically, the volume concentration of the particles in the composition before filtering is less than 50%, e.g., less than 25%, such as between about 10% and about 20%, as described below. For some applications, two bores are formed through the maxillary alveolar ridge to below the Schneiderian membrane. The regenerative material is injected though a first bore, and at least a portion of the physiological solution drains through a filter in (or in communication with) the second bore, leaving at least a portion of solid bone graft particles in a cavity formed between the ridge and the membrane. Typically, the volume concentration of the particles in the composition after filtering is greater than 50%, e.g., between about 80% and about 100%. For some applications, this technique is used for bones other than the maxillary alveolar ridge, such as a mandibular alveolar ridge.

Figure 19A:
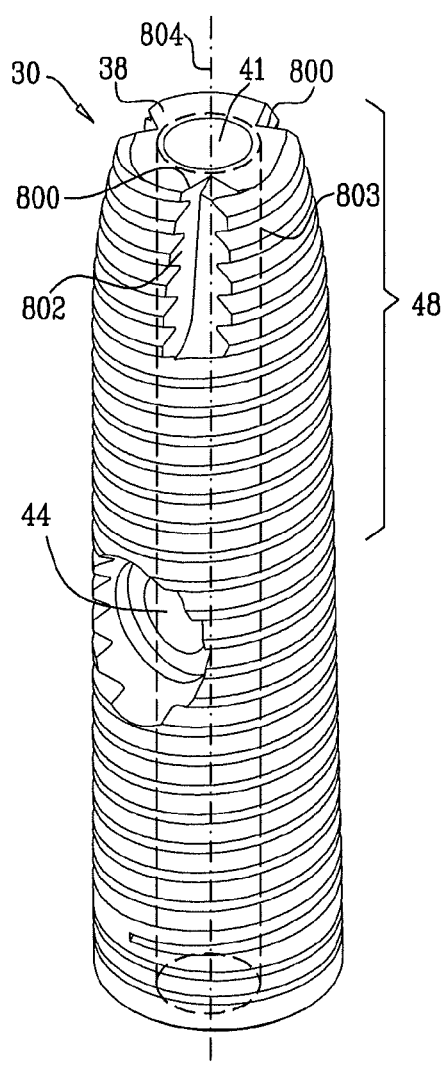
FIGS. 19A-B are schematic lateral and head-on illustrations, respectively, of a configuration of a distal surface of the dental implant of FIG. 1, in accordance with an embodiment of the present invention.
Figure 19B:
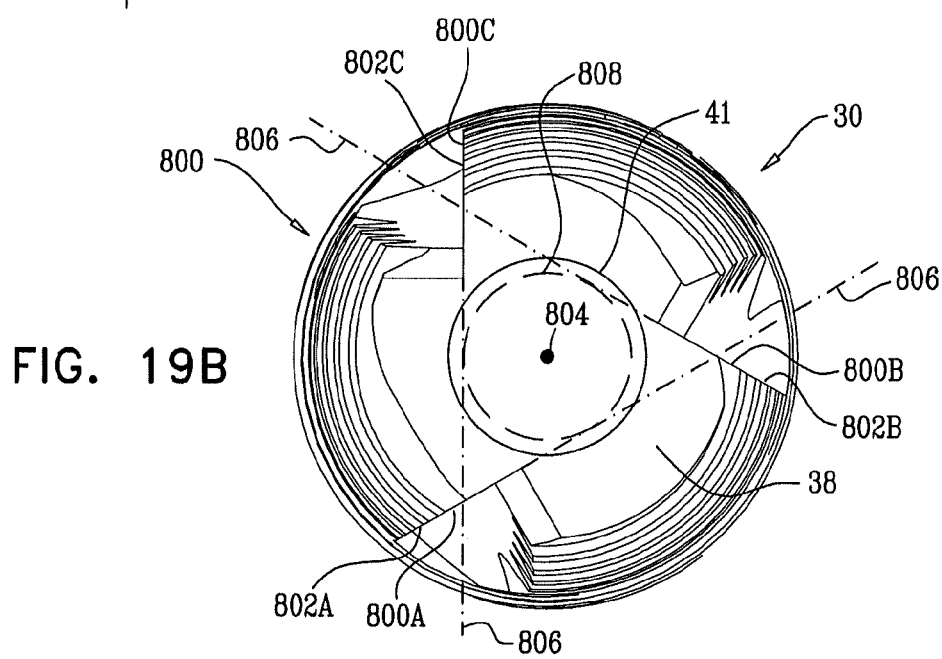

Reference is made to FIGS. 19A-B, which are schematic lateral and head-on illustrations, respectively, of a configuration of a distal surface of dental implant 30, in accordance with an embodiment of the present invention. For some applications, this configuration is used for implants described hereinabove with reference to FIGS. 1, 2F, 3A-D, 4A-B, 5, 6, 7, 8, 9A-E, 10, 11A-F, 12A-B, 13A-B, 15A-C, and/or 16. As described hereinabove with reference to FIG. 1, implant 30 is shaped so as to define a lumen therethrough that is open through at least one distal opening 41 to distal portion 48 of the implant that extends from distal implant end 38 of the implant along up to 50% of a longitudinal length of the implant. Typically, the at least one opening is located at the center of the distal implant end.

In the present configuration, distal portion 48 is shaped so as to define at least one surface selected from the group consisting of: at least one end mill cutter surface 800, at least one self-tapping surface 802, and both the at least one end mill cutter surface and the at least one self-tapping surface (as shown in FIGS. 19A-B). Unlike conventional end mill and self-tapping surfaces, the end mill cutter and self-tapping surfaces do not extend into a central area of the implant that defines the lumen. This confining of the surfaces to the outer area of the implant accommodates the distal opening and lumen. For some applications, the end mill and self-tapping surfaces do not extend into a cylindrical area 803, a central axis of which coincides with a central axis 804 of the implant, and which area extends along the entire length of the implant. Cylindrical area 803 typically has a diameter of at least 0.3 mm, such as at least 0.5 mm, or at least 1.5 mm. For some applications, the diameter of the lumen is between 0.3 and 2 mm, such as between 0.5 and 2 mm, e.g., between 1.5 and 1.6 mm. For some applications, the greatest diameter of the implant (i.e., the diameter of the implant at its widest portion) is no more than 5 mm, such as no more than 4.2 mm, or is between 3 and 6.5 mm.

The end mill cutter surface creates bone fragments and bone dust that protects the Schneiderian membrane or periosteal tissue as the implant is advanced through the bone. In addition, the end mill cutter surface grinds the bone of the ridge, which is generally effective for breaking through bone. Distal portion 48 both engages the lower portion of the bone while at the same time breaking through the upper portion of the bone.

For some applications, end mill cutter surface 800 is shaped so as to define exactly two, exactly three, exactly four, exactly five, or exactly six cutting surfaces. For example, in the configuration shown in FIGS. 19A and 19B, end mill cutter surface 800 defines exactly three cutting surfaces 800A, 800B, and 800C, i.e., is tripartite, and self-tapping surface 802 defines exactly three self-tapping surfaces 802A, 802B, and 802C. Typically, the cutting surfaces are distributed evenly about a central axis 804 of the implant, offset from the center. Lines 806 respectively defined by the cutting surfaces are typically tangential to a circle 808 having a center which is intersected by central axis 804 of the implant (the circle may or may not have the same radius as distal opening 41). Thus, for example, for applications in which the end mill cutter surface defines exactly two cutting surfaces 802, lines 806 are parallel to one another; for applications in which the end mill cutter surface defines exactly three cutting surfaces 802, lines 806 form a triangle; and, for application in which the end mill cutter surface defines exactly four cutting surfaces 802, lines 806 form a square.

For some applications, distal portion 48 is shaped so as to define a conical cross-section that is configured to cause bone condensation, which generally improves bone density.

Figure 20:
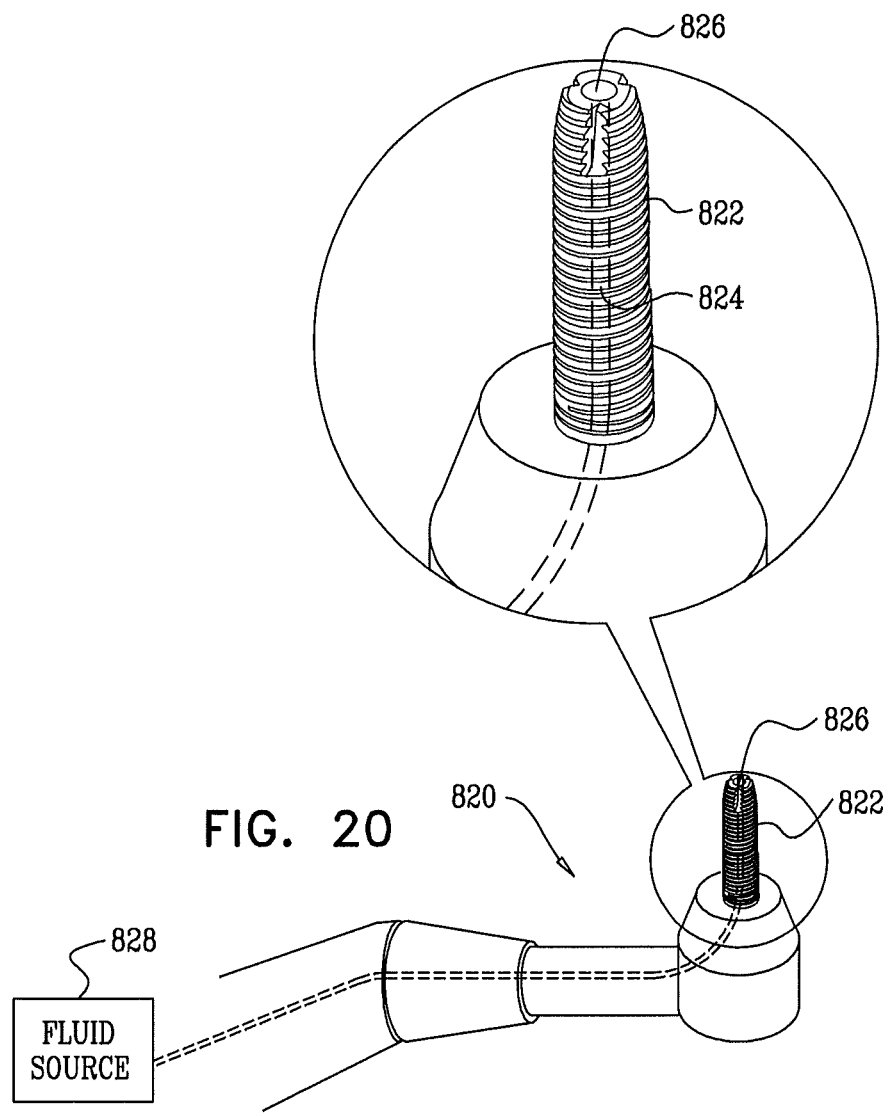
FIG. 20 is a schematic illustration of another dental drill, in accordance with an embodiment of the present invention.

Reference is made to FIG. 20, which is a schematic illustration of a dental drill 820, in accordance with an embodiment of the present invention. Drill 820 comprises a bit 822 which is shaped so as to define a lumen 824 therethrough that is open to a distal portion of the bit that extends from a distal end 826 of the bit along up to 8 mm of a longitudinal length of the bit, such as up to 6 mm of the length, up to 4 mm of the length, or up to 2 mm of the length. For some applications, lumen 824 is open to distal end 826 of the bit, either at the tip of the bit (e.g., at the center of the tip) or in the general area of the distal end of the bit.

The surgeon uses drill 820 to perform a sinus lift procedure, such as described hereinabove with reference to FIG. 14, a lateral ridge augmentation, such as described hereinbelow with reference to FIGS. 22A-F or FIGS. 23A-F, or another dental procedure. For some applications, drill 820 is coupled to a source of pressure 828. For some applications, while the surgeon drills a bore through the maxillary alveolar ridge, fluid source 828 provides a fluid under monitored pressure to the distal bit portion, such as distal bit end 826, via lumen 824. The fluid typically comprises a biocompatible solution such as normal saline solution, or a gas, e.g., air.

The distal portion of bit 822 is shaped so as to define at least one surface selected from the group consisting of: at least one end mill cutter surface, at least one self-tapping surface, and both the at least one end mill cutter surface and the at least one self-tapping surface, such as described hereinabove for the implant with reference to FIGS. 19A-B. Unlike conventional end mill and self-tapping surfaces, the end mill cutter and self-tapping surfaces do not extend into a central area of the bit that defines lumen 824. This confining of the surfaces to the outer area of the bit accommodates the distal opening and lumen. For some applications, the end mill and self-tapping surfaces do not extend into a cylindrical area, which area extends along the entire length of the bit, and the central axis of which coincides with a central axis of the bit, and which has a diameter of at least 0.3 mm, such as at least 0.5 mm, or at least 1.5 mm. For some applications, the greatest diameter of the bit (i.e., the diameter of the bit at its widest portion) is no more than 5 mm, such as no more than 4.2 mm.

The end mill cutter surface creates bone fragments and bone dust that protects the Schneiderian membrane or periosteal tissue as the drill bit is advanced through the bone. In addition, the end mill cutter surface grinds the bone of the ridge, which is generally effective for breaking through bone.

For some applications, the end mill cutter surface is shaped so as to define exactly two, exactly three, exactly four, exactly five, or exactly six cutting surfaces, such as described hereinabove for the implant with reference to FIGS. 19A-B. For example, in the configuration shown in FIG. 20, the end mill cutter surface defines exactly three cutting surfaces, i.e., is tripartite, and the self-tapping surface defines exactly three self-tapping surfaces. Typically, the cutting surfaces are distributed evenly about a central axis of the bit, offset from the center. Lines respectively defined by the cutting surfaces are typically tangential to a circle having a center which is intersected by the central axis of the bit (the circle may or may not have the same radius as the distal opening).

For some applications, the distal portion of bit 822 is shaped so as to define a conical cross-section that is configured to cause bone condensation, which generally improves bone density.

Reference is made to FIGS. 21A-E, which are schematic illustrations of a dental implant 930, in accordance with respective embodiments of the present invention. Dental implant 930 is shaped so as to define a lumen 940 therethrough that is open through a distal opening 941 to a distal portion 948 of the implant that extends from a distal implant end 938 of the implant along up to 50% of a longitudinal length of the implant, such as up to 30% of the length, up to 15% of the length, or up to 5% of the length. For some applications, distal portion 948 has a longitudinal length of up to 6 mm, such as up to 4 mm, or up to 2 mm.

Distal opening 941 may be located at distal implant end 938, such as centered on the distal implant end, e.g., at a distal tip of distal implant end 938, or not centered on the distal implant end (and thus located at a location other than the distal tip), such as described hereinabove with reference to FIG. 2A. Alternatively, distal opening(s) 941 may be located at one or more locations along distal implant portion 948, including at locations on a lateral surface of the implant. For some applications, the lumen is open to the distal end via a plurality of openings 941, which for some applications results in a more even distribution of regenerative material in the cavity between the ridge and the Schneiderian membrane, as described hereinabove, and/or permits passage of the regenerative material even if some of the openings should become blocked with bone particles.

Dental implant 930 is typically generally cylindrical, tapered, or conic in shape, other than the lumen, and typically comprises a metal such as titanium, or a ceramic, such as a zirconia (zirconium dioxide) ceramic. The implant may have a greatest diameter of between about 2 and about 7 mm, and may be provided in a variety of longitudinal lengths, e.g., between about 7 and about 18 mm, e.g., between about 12 and about 16 mm, such as about 15 mm. For some applications, the implant has a longitudinal length of less than 20 mm and a greatest diameter of less than 10 mm. Typically, implant 930 comprises a two-stage implant. The surgeon couples an abutment to the proximal end of the implant after osseointegration of the implant, as is known in the art, such as described hereinabove with reference to FIG. 11F. Alternatively, implant 930 comprises a single-stage transgingival implant, which is shaped so as to define an integrated abutment, as is known in the art. Dental implant 930 may incorporate one or more features of dental implant 30 described herein.

The proximal end of lumen 940 is open to a proximal implant end 934 through a proximal opening 950 of the implant. After the implant has been inserted into a bore, such as using the technique described herein, or other techniques known in the art, proximal opening 950 is permanently sealed in order to reduce the risk of infection, and/or provide additional structural strength to the implant.

Figure 21A:
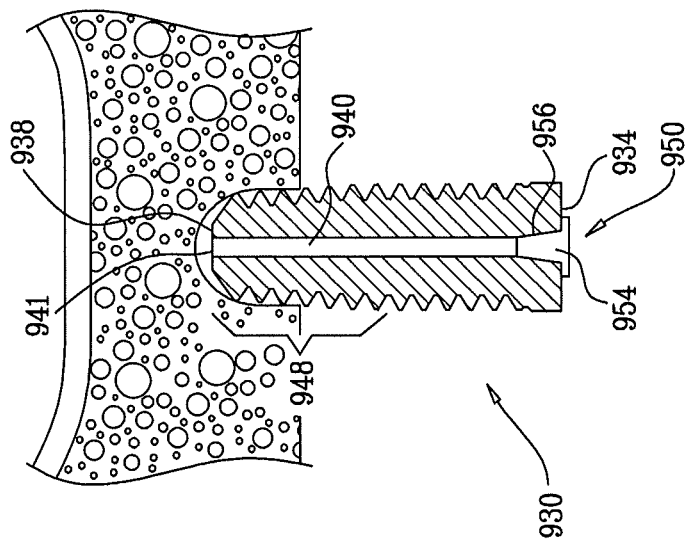
Figure 21B:
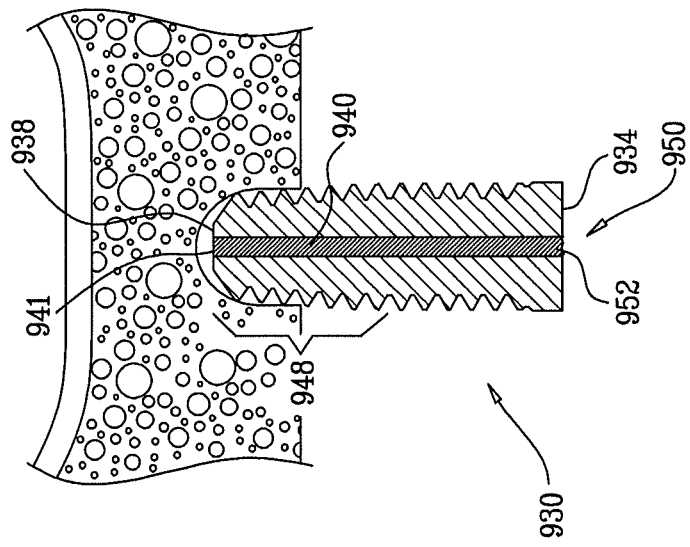
Figure 21C:
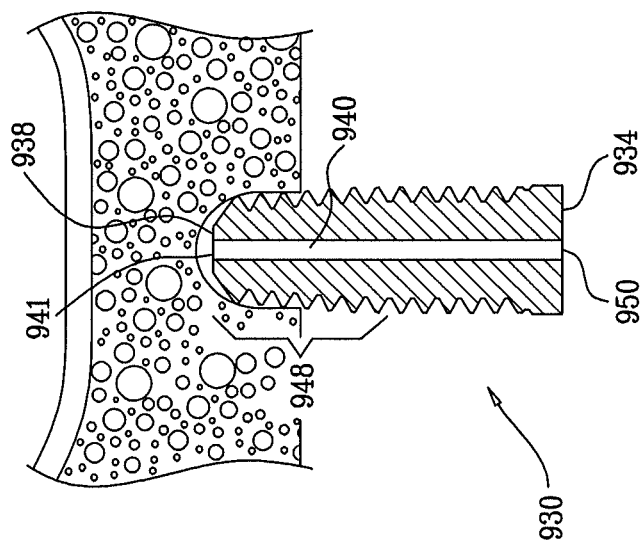

For some applications, one or more of the following techniques are used to seal the proximal opening:

- a filling material 952 is placed in the proximal opening, such as rubber or a glue, as shown in FIG. 21B;
- a mechanical plug 954 is sealingly coupled to the proximal opening. For example, the plug may be shaped so as to define a male Morse taper 956, and the proximal opening correspondingly shaped female Morse taper, as shown in FIG. 21C;
- a screw covering 960 is sealingly coupled to the proximal opening, such as using a gasket 962, as shown in FIG. 21D;
- a covering 964 is welded to the opening using a laser placed in the mouth, as shown in FIG. 21E; or
- a covering is crimped to the opening (configuration not shown). The proximal end of the implant may define a lip, around which the covering is crimped. For some applications, a sealing element, such as a gasket, is provided between the covering and proximal implant end 934 and/or a distal side of the lip.

Reference is made to FIGS. 22A-F, which are schematic illustrations of several steps of a minimally-invasive closed lateral ridge augmentation surgical procedure for implanting a dental implant 1030, in accordance with an embodiment of the present invention. The procedure is typically employed when a patient's maxillary or mandibular alveolar ridge 1000 lacks sufficient bone width to support a dental implant, as shown in FIG. 22A. For example, the procedure may be employed for implanting an implant to replace the upper canines, lower molars, upper incisors, or lower incisors.

Dental implant 1030 is typically similar to dental implant 30, such as the embodiment described hereinabove with reference to FIGS. 3A-D, 4A-B, 5, and 6 (as shown in FIGS. 22A-F), or the embodiment described hereinabove with reference to FIGS. 7, 8, 9A-E, and 10 (not shown in FIGS. 22A-F). Among other features, dental implant 1030 has a distal implant portion that extends from a distal implant end along up to 50% of a longitudinal length of the implant, and the implant shaped so as to define a lumen therethrough having at least one distal opening through a distal external surface of the distal implant portion. A lateral opening 1044 of implant 1030 is typically located more proximally on the implant than is lateral opening 44 of implant 30. For example, lateral opening 1044 may be located between 2 and 16 mm from the distal end of the implant, such as between 3 and 10 mm. This closed lateral ridge augmentation surgical procedure may be performed in combination with other techniques described herein. For some applications, the distal opening of the lumen is located on a lateral surface of the implant near the distal end, rather than on the distal end itself.

A surgeon begins the procedure by preparing the oral facial region, and administering a local anesthetic. Optionally, the surgeon initiates an osteotomy in alveolar ridge 100 by making a preliminary portion of a bore using a dental drill, such as a conventional sinus bur. This preliminary bore portion typically has a diameter of between about 1 and about 7 mm, e.g., between about 2 and about 6 mm. Optionally, the surgeon widens the bore using a series of successively wider drill bits, until a desired bore diameters is achieved (for example, the largest drill bit may have a diameter of 3.65 mm for an implant having a diameter of 4.2 mm, or a diameter of 4.2 mm for an implant having a diameter of 5 mm). The bore may be measured using techniques known in the art, such as CT, x-ray, or x-ray with a depth guide. For some applications, a surgical guide is used to ensure clearance between the center of the osteotomy and the nearest tooth surfaces. Optionally, a pre-surgery radiograph (e.g., CT or x-ray) is performed, to enable the surgeon to estimate the necessary depth of the osteotomy.

After drilling the preliminary bore portion, the surgeon advances dental implant 1030 into the bore by screwing the implant into ridge 1000 using a surgical screwing tool. The screwing tool may comprise a conventional manual ratchet wrench, or a conventional drill or motor to which an appropriate drill head is attached, and which is operated at a low speed and at low torque. Alternatively, the screwing tool may comprise a conventional hexagonal tool with a knurled knob, such as a knurled hex screwdriver, and along its axis, a thin rod having a hexagonal head which fits into a female hexagonal socket defined by a proximal end of an applicator 1032.

As shown in FIG. 22B, the surgeon inserts implant 1030 into the bore at least until the distal opening comes into fluid communication with periosteal tissue 1040 covering a lateral surface of the bone. The surgeon delaminates periosteal tissue 1040 from the bone by injecting a fluid 1029 through the lumen of the implant to form a cavity 1020 between the bone and periosteal tissue 1040, as shown in FIG. 22C. For example, fluid 1029 may comprise a biocompatible solution such as normal saline solution or a gas. The fluid is provided by a fluid source 1054, such as a manual syringe 1126, via a supply tube 1052.

The fluid is typically drained from the cavity, and the surgeon injects a regenerative material 1031, such as liquid or gel bone graft, into cavity 1120, as shown in FIG. 22D. Fluid source 1054 or a separate syringe or powered drug delivery device is used for injecting the regenerative material. If a separate syringe or device is used to inject the material, the material may be provided via supply tube 1052, or via a separate supply tube. Regenerative material 1031 may comprise an allograph, an autogeneous bone graft, or a xenograft, and may, for example, comprise a natural material, a synthetic material, or a mixture thereof. For example, regenerative material 1031 may comprise one of the following commercially available fluid bone graft materials: DBX Paste (MTF), Allomatrix (Wright), Cerament (Bone Support), DynaGraft (Citagenix/ISOTIS), Fisiograft (Ghimas), Grafton (Osteotech), Optium DBM Gel (Lifenet/Depuy J&J), OsteoMax (Orthfix), PD VitalOs Cemen (VitalOs), or Regenafil® (Exactech). Alternatively, regenerative material 1031 may comprise the composition described hereinabove that comprises saline solution mixed with solid bone graft particles. Optionally, the system monitors and generates an output indicative of the pressure of the regenerative material as it is injected.

For some applications, the system measures the volume of fluid 1129 injected into the cavity while forming the cavity, at the step of the procedure described hereinabove with reference to FIGS. 22B-C. Responsively to the measured volume, the surgeon determines an amount of regenerative material 1031 to inject into cavity 1120 at the step of the procedure described hereinabove with reference to FIG. 22D. Typically, the amount of regenerative material 1031 is approximately equal to the volume of injected fluid 1129, or slightly greater or less than the volume of the injected fluid. As a result, waste of regenerative material 1031 is generally minimized.

For some applications, the surgeon uses a flexible wire as a piston to help push the regenerative material through the supply tubes and/or lumen. This technique may be helpful when the regenerative material is viscous and thus difficult to inject using an ordinary syringe.

Alternatively, the surgeon injects regenerative material 1031, rather than fluid 1129, to delaminate periosteal tissue 1040 from the bone, thereby combining the steps of the procedure described hereinabove with reference to FIGS. 22B-C and 22D. In this case, the regenerative material typically comprises a liquid.

The surgeon decouples a delivery tube 1050 from implant 1030, and further advances (e.g., by rotating or screwing) implant 1030 into regenerative material 1031 in cavity 1120, as shown in FIG. 22E. This additional advancing of the implant advances the lateral surface of implant 1030 at least until lateral opening 1044 is positioned entirely within the bore in ridge 1000 and/or in regenerative material 1031 in cavity 1120. Such positioning of both ends of the lumen within bone substantially reduces the risk of infection, because the proximal end of implant 1030 that is exposed to the oral cavity or gingiva is permanently closed.

The surgeon may decouple the delivery tube before or while further advancing the implant, and/or by advancing the implant until the tube becomes decoupled because of the rotation. For some applications, the surgeon decouples the delivery tube using the tools and techniques described hereinabove with reference to FIGS. 12A and 12B. The surgeon decouples applicator 1032 from implant 1030, such as by pulling the male coupling element out of the female coupling element, or using the tool and techniques described hereinabove with reference to FIG. 12C-E. Typically, the surgeon couples a cover screw to the proximal end of the implant using a hand driver, and sutures the gingiva.

As shown in FIG. 22F, bone grows into regenerative material 1031 and is integrated into ridge 1000. Thereafter, an appliance, such as a crown, is coupled to implant 1030, typically using an abutment coupled to the implant, as is known in the art. Alternatively, implant 1030 comprises a single-stage transgingival implant/abutment, as is known in the art.

Figure 23D:
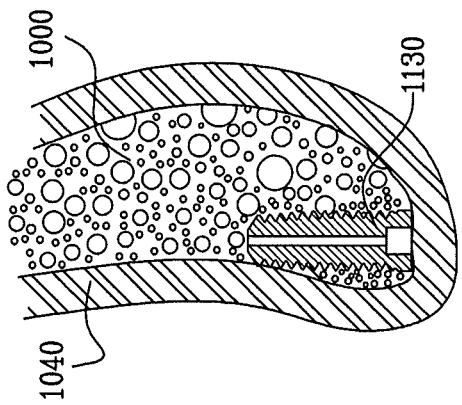

Reference is made to FIGS. 23A-F, which are schematic illustrations of several steps of another minimally-invasive closed lateral ridge augmentation surgical procedure for implanting a dental implant 1130, in accordance with an embodiment of the present invention. Except as described below, the procedure is generally similar to the procedure described hereinabove with reference to FIGS. 22A-F. The procedure is typically employed when a patient's maxillary or mandibular alveolar ridge 1000 lacks sufficient bone width to support a dental implant, as shown in FIG. 23A. For example, the procedure may be employed for implanting an implant to replace the upper canines, lower molars, upper incisors, or lower incisors.

In this embodiment, unlike in the embodiment described hereinabove with reference to FIGS. 22A-F, dental implant 1130 is typically similar to dental implant 930, described hereinabove with reference to FIGS. 21A-E. Among other features, dental implant 1130 has a distal implant portion that extends from a distal implant end along up to 50% of a longitudinal length of the implant, and the implant shaped so as to define a lumen 1140 therethrough having at least one distal opening through a distal external surface of the distal implant portion. The proximal end of lumen 1140 is open to a proximal implant end through a proximal opening of the implant. This closed lateral ridge augmentation surgical procedure may be performed in combination with other techniques described herein. For some applications, the distal opening of lumen 1140 is located on a lateral surface of the implant near the distal end, rather than on the distal end itself.

As described hereinabove with reference to FIGS. 22A-F, the surgeon may initiate an osteotomy in alveolar ridge 1000 by making a preliminary portion of a bore using a dental drill.

After drilling the preliminary bore portion, the surgeon advances dental implant 1130 into the bore by screwing the implant into ridge 1000 using a surgical screwing tool. The screwing tool may comprise a conventional manual ratchet wrench, or a conventional drill or motor to which an appropriate drill head is attached, and which is operated at a low speed and at low torque. Alternatively, the screwing tool may comprise a conventional hexagonal tool with a knurled knob, such as a knurled hex screwdriver, and along its axis, a thin rod having a hexagonal head which fits into a female hexagonal socket defined by a proximal end of an applicator 1132. For some applications, applicator 1132 comprises a swivel joint, such as described hereinbelow with reference to FIGS. 26 and 27A-B.

As shown in FIG. 23B, the surgeon inserts implant 1130 into the bore at least until the distal opening comes into fluid communication with periosteal tissue 1040 covering a lateral surface of the bone, and at least until the proximal end of the implant is flush with the bone. The surgeon delaminates periosteal tissue 1040 from the bone by injecting fluid 1029 through the lumen of the implant to form cavity 1020 between the bone and periosteal tissue 1040, as shown in FIG. 23C. For example, fluid 1029 may comprise a biocompatible solution such as normal saline solution or a gas. The fluid is provided by fluid source 1054, such as manual syringe 1126, via supply tube 1052.

The fluid is typically drained from the cavity, and the surgeon injects regenerative material 1031, such as liquid or gel bone graft, into cavity 1120, as shown in FIG. 23D, such as using techniques and materials described hereinabove with reference to FIG. 22D. Alternatively, the surgeon injects regenerative material 1031, rather than fluid 1129, to delaminate periosteal tissue 1040 from the bone, thereby combining the steps of the procedure described hereinabove with reference to FIGS. 23B-C and 23D. In this case, the regenerative material typically comprises a liquid.

Figure 23E:
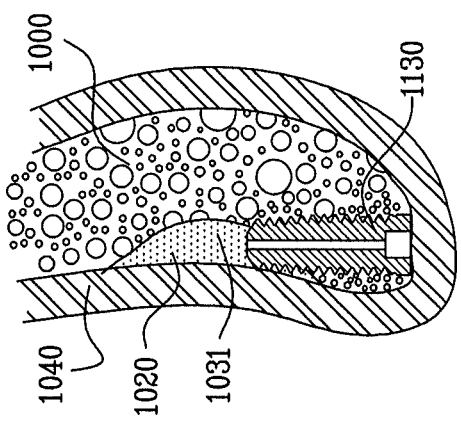

The surgeon decouples supply tube 1052 from implant 1130, leaving the implant in the ridge, as shown in FIG. 23E. Typically, the surgeon couples a cover screw to the proximal end of the implant using a hand driver (not shown), and sutures the gingiva.

Figure 23F:
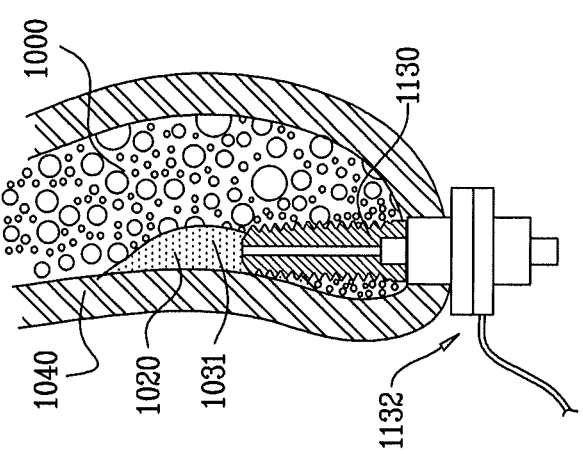

As shown in FIG. 23F, bone grows into regenerative material 1031 and is integrated into ridge 1000. Thereafter, an appliance, such as a crown, is coupled to implant 1130, typically using an abutment coupled to the implant, as is known in the art. Alternatively, implant 1130 comprises a single-stage transgingival implant/abutment, as is known in the art.

In an embodiment of the present invention, the procedure described with reference to FIGS. 23A-F is performed using a drill bit having a lumen, such as described hereinabove with reference to FIGS. 14 and/or 20, or a conventional surgical drill with irrigation, such as internal irrigation, as is known in the art and commercially available. A dental drill bit is provided that has a distal bit portion that extends from a distal bit end along up to 6 mm of a longitudinal length of the bit, the bit shaped so as to define a lumen therethrough having at least one distal opening through a distal external surface of the distal bit portion. The surgeon forms a bore in a bone of an alveolar ridge by inserting the bit into the bone and rotating the bit using a drill. The surgeon advances the bit into the bore at least until the distal opening comes into fluid communication with periosteal tissue covering a lateral surface of the bone. The surgeon delaminates the periosteal tissue from the bone by injecting a fluid through the lumen to form a cavity between the bone and the periosteal tissue. After delaminating the periosteal tissue, the surgeon injects a regenerative material into the cavity via the lumen. The surgeon removes the drill bit, and inserts a dental implant, which may be conventional, into the bore and regenerative material. Typically, the diameter of the implant is equal to or slightly greater than the diameter of the drill bit.

For some applications, while injecting the fluid, the volume of the injected fluid is measured, and an amount of the regenerative material to inject into the cavity is determined responsively to the measured volume of the fluid. Typically, the alveolar ridge is either a maxillary alveolar ridge or a mandibular alveolar ridge.

Figure 24A:
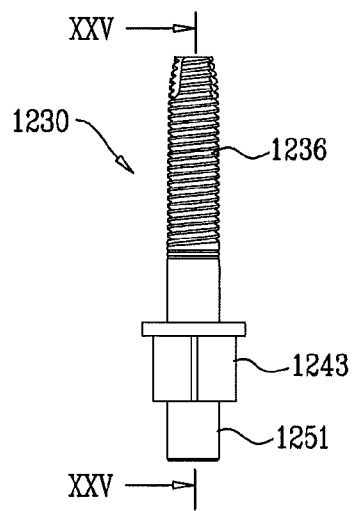
FIGS. 24A-C and 25 are schematic illustrations of a liquid osteotome, in accordance with an embodiment of the present invention.
Figure 24B:
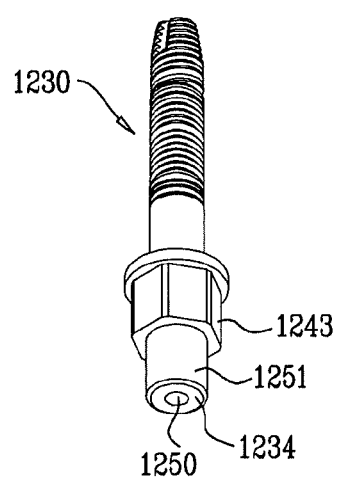
Figure 24C:
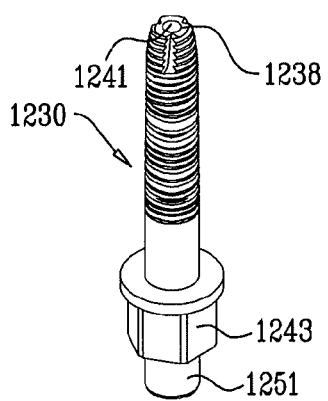
Figure 25:
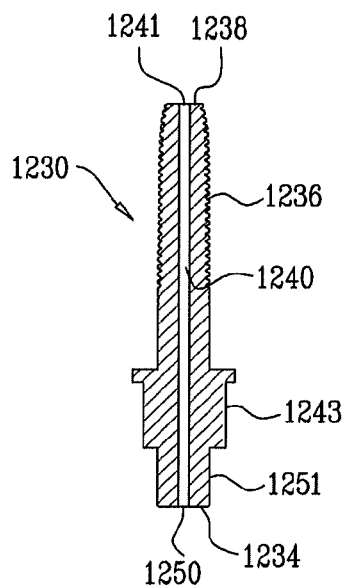

Reference is now made to FIGS. 24A-C and 25, which are schematic illustrations of a liquid osteotome 1230, in accordance with an embodiment of the present invention. FIGS. 24A-C are views from respective directions of the osteotome, FIG. 25 is a cross-sectional view taken along line XXV-XXV of FIG. 24A.

In an embodiment of the present invention, osteotome 1230 is used to perform a sinus lift procedure, e.g., a controlled sinus lift procedure, such as described hereinabove with reference to FIGS. 11A-D. After the Schneiderian membrane has been lifted, and the regenerative material has been injected into the cavity below the membrane, the surgeon removes osteotome 1230 from the ridge. A dental implant, which may be conventional, is inserted into the bore and cavity. Typically, the diameter of the implant is equal to or slightly greater than the diameter of osteotome 1230.

In an embodiment of the present invention, osteotome 1230 is used to perform a lateral ridge augmentation, such as described hereinabove with reference to FIGS. 23A-F. After the periosteal tissue has been delaminated from the bone, and the regenerative material has been injected into the cavity, the surgeon removes osteotome 1230 from the ridge. A dental implant, which may be conventional, is inserted into the bore and cavity. Typically, the diameter of the implant is equal to or slightly greater than the diameter of the portion of osteotome 1230 that defines a cutting surface, as described hereinbelow.

Osteotome 1230 is shaped so as to define a lumen 1240 therethrough that is open through a distal opening 1241 to a distal portion of the osteotome that extends from a distal osteotome end 1238 of the osteotome along up to 8 mm of a longitudinal length of the osteotome, such as up to 6 mm of the length, up to 4 mm of the length, or up to 2 mm of the length.

Distal opening 1241 may be located at distal osteotome end 1238, such as centered on the distal osteotome end, e.g., at a distal tip of distal osteotome end 1238, or not centered on the distal osteotome end (and thus located at a location other than the distal tip), such as described hereinabove with reference to FIG. 2A. Alternatively, distal opening(s) 1241 may be located at one or more locations along distal osteotome portion 1248, including at locations on a lateral surface of the osteotome. For some applications, the lumen is open to the distal end via a plurality of openings 1241, which for some applications results in a more even distribution of regenerative material in the cavity, and/or permits passage of the regenerative material even if some of the openings should become blocked with bone particles.

At least a portion of a lateral external surface of osteotome 1230 is shaped as to define a cutting surface, typically a screw thread 1236. Osteotome 1230 is typically generally cylindrical, tapered, or conic in shape, other than the lumen, and typically comprises a metal such as stainless steel, titanium, or a ceramic. The portion of the osteotome including the cutting surface (e.g., screw thread 1236) may have a greatest diameter of between about 2 and about 5 mm, e.g., 3.75 mm.

The proximal end of lumen 1240 is open to a proximal osteotome end 1234 through a proximal opening 1250 of the osteotome. A supply tube (not shown) is coupled to the proximal opening in order to supply fluid and regenerative material to the lumen, as described hereinabove. Typically, the supply tube is inserted into a short channel defined by a proximal-most portion 1251 of the osteotome, which portion may have a length of between 2 and 5 mm, for example.

The proximal end is shaped so as to define a coupling element 1243, such as a male coupling element, e.g., a hexagonal head. The surgeon typically uses conventional dental wrenches to engage the coupling element and rotate the osteotome.

In an embodiment of the present invention, the distal portion of the osteotome is shaped so as to define at least one surface selected from the group consisting of: at least one end mill cutter surface, at least one self-tapping surface, and both the at least one end mill cutter surface and the at least one self-tapping surface, such as described hereinabove for the implant with reference to FIGS. 19A-B. Unlike conventional end mill and self-tapping surfaces, the end mill cutter and self-tapping surfaces do not extend into a central area of the osteotome that defines lumen 1240. This confining of the surfaces to the outer area of the osteotome accommodates the distal opening and lumen. For some applications, the end mill and self-tapping surfaces do not extend into a cylindrical area, a central axis of which coincides with a central axis of the osteotome, and which area extends along the entire length of the osteotome. The cylindrical area typically has a diameter of at least 0.3 mm, such as at least 0.5 mm, or at least 1.5 mm. For some applications, the greatest diameter of the osteotome (i.e., the diameter of the osteotome at its widest portion) is no more than 5 mm, such as no more than 4 mm.

The end mill cutter surface creates bone fragments and bone dust that protects the Schneiderian membrane or periosteal tissue as the osteotome is advanced through the bone. In addition, the end mill cutter surface grinds the bone of the ridge, which is generally effective for breaking through bone.

For some applications, the end mill cutter surface is shaped so as to define exactly two, exactly three, exactly four, exactly five, or exactly six cutting surfaces, such as described hereinabove for the implant with reference to FIGS. 19A-B. For example, in the configuration shown in FIGS. 24A-C and 25, the end mill cutter surface defines exactly three cutting surfaces, i.e., is tripartite. Typically, the cutting surfaces are distributed evenly about a central axis of the osteotome, offset from the center. Lines respectively defined by the cutting surfaces are typically tangential to a circle having a center which is intersected by the central axis of the osteotome (the circle may or may not have the same radius as the distal opening).

For some applications, the distal portion of the osteotome is shaped so as to define a conical cross-section that is configured to cause bone condensation, which generally improves bone density.

Typically, a total length of osteotome 1230 is between 5 and 35 mm, such as between 8 and 28 mm.

Reference is made to FIGS. 26 and 27A-B, which are schematic illustrations of a liquid osteotome 1330 that comprises a swivel joint 1364, in accordance with an embodiment of the present invention. FIG. 27A is a cross-sectional view taken along line XXVIIA-XXVIIA of FIG. 26, and FIG. 27B is a cross-sectional view of another configuration of osteotome 1330. Other than as described hereinbelow, osteotome 1330 is generally similar in structure and use to osteotome 1230, described hereinabove with reference to FIGS. 24A-C and 25. Osteotome is typically used to perform a sinus lift or lateral ridge augmentation, as described hereinabove with reference to FIGS. 24A-C and 25.

Osteotome 1330 comprises a swivel joint 1364 having first and second joint portions, which define first and second joint ports, respectively. For some applications, the first joint portion is a distal joint portion 1362, and the second joint portion is a proximal joint portion 1360, as shown in FIG. 27A. For other application, the first joint portion is proximal joint portion 1360, and the second joint portion is distal joint portion 1362, as shown in FIG. 27B.

Joint 1364 is arranged so as to define a fluid path from the first joint port to the second joint port via first and second joint portions. The fluid path is thus defined from (a) lumen 1240, to (b) the first joint port, to (c) the first joint portion, to (d) the second joint portion, to (e) the second joint portion. The joint portions are arranged to be rotatable with respect to one another such that the fluid path is preserved during rotation. Typically, the first joint portion is fixed to the body of osteotome 1330, while the second joint portion is configured to rotate freely with respect to the body of the osteotome and the first joint portion.

The proximal end of lumen 1240 is open through a lateral opening 1341 on a lateral surface of the osteotome (rather than through a proximal opening 1250, as is the case for osteotome 1230, described hereinabove with reference to FIGS. 24A-C and 25). The lateral opening is aligned with the first joint port, such that the lateral opening is in fluid communication with the first joint port, and a fluid path is defined from the lumen to the first joint portion. Alternatively, the swivel joint further comprises a delivery tube, and the swivel joint is configured as described hereinabove with reference to FIG. 1.

A supply tube 1352 is coupled to the second joint port, such that lumen 1240 and supply tube 1352 are in fluid communication with one another via swivel joint 1364.

Swivel joint 1364 defines a bore therethrough, in which a portion of the body of the osteotome is positioned. The proximal end of the osteotome is shaped so as to define coupling element 1243, such as a male coupling element, e.g., a hexagonal head. The surgeon typically uses conventional dental wrenches to engage the coupling element and rotate the osteotome, while the second joint port remains generally stationary because it is connected to supply tube 1352. This configuration thus allows convenient rotation of the osteotome without the need to rotate the supply tube. In addition, osteotome 1340 is generally shorter than osteotome 1240 because osteotome 1340 does not include proximal-most portion 1251, which is used for coupling the supply tube to osteotome 1240, as described hereinabove with reference to FIGS. 24A-C and 25. Furthermore, osteotome 1340 occupies less space in the patient's mouth than does osteotome 1240, because there is no need to accommodate the bending radius of a supply tube inserted into proximal-most portion 1251 of osteotome 1240, as described hereinabove with reference to FIGS. 24A-C and 25.

Typically, a total length of osteotome 1330 is between 5 and 35 mm, such as between 8 and 28 mm.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
a dental implement, having a distal portion that extends from a distal end along up to 50% of a longitudinal length of the implement, the implement being shaped so as to define a lumen therethrough having at least one distal opening through a center of the distal end, and the implement having a greatest diameter no more than 8 mm and a length of at least 3 mm,
wherein at least a portion of the distal portion is shaped so as to define a plurality of end mill cutter surfaces configured to grind bone, which are distributed about a central axis of the implement, such that lines respectively defined by the cutter surfaces are tangential to a circle having a center which is intersected by the central axis of the implement, and
wherein the end mill cutter surfaces do not extend into a central area of the implement that defines the lumen.

2. The apparatus according to claim 1, wherein the distal portion is shaped so as to define both the end mill cutter surfaces and at least one self-tapping surface.

3. The apparatus according to claim 1, wherein the end mill cutter surfaces do not extend into a cylindrical area of the implement, a central axis of which area coincides with a central axis of the implement, which area extends along the entire length of the implement, and which cylindrical area has a diameter of at least 0.3 mm.

4. The apparatus according to claim 1, wherein the end mill cutter surfaces comprise exactly three end mill cutter surfaces.

5. The apparatus according to claim 1, wherein the dental implement comprises a dental implant.

6. The apparatus according to claim 1, wherein the dental implement comprises a dental osteotome.

7. The apparatus according to claim 1, wherein the implement has a proximal-most part, a lateral external surface, and a proximal external surface, and wherein the implement is shaped such that the lumen has a lateral opening through the lateral external surface, and the lumen is not open to the proximal external surface of the implement within 2 mm of the proximal-most part of the implement.

8. The apparatus according to claim 1, wherein at least a portion of a lateral external surface of the implement is shaped so as to define a cutting surface.

9. The apparatus according to claim 8, wherein the cutting surface defined by the at least a portion of the lateral external surface comprises a screw thread.

10. The apparatus according to claim 1, wherein at least a portion of a lateral external surface of the dental implement is shaped so as to define a screw thread.

11. A method comprising:
providing a dental implement having a distal portion that extends from a distal end along up to 50% of a longitudinal length of the implement, the implement being shaped so as to define a lumen therethrough having at least one distal opening through a center of the distal end, wherein at least a portion of the distal portion is shaped so as to define a plurality of end mill cutter surfaces configured to grind bone, which are distributed about a central axis of the implement, such that lines respectively defined by the cutter surfaces are tangential to a circle having a center which is intersected by the central axis of the implement, and wherein the end mill cutter surfaces do not extend into a central area of the implement that defines the lumen;
forming a portion of a bore in an alveolar ridge; and inserting the dental implement into the bore, and by rotating the dental implement in the bore, grinding and breaking through a top of the alveolar ridge to below a Schneiderian membrane.

12. The method according to claim 11, wherein providing the dental implement comprises providing the dental implement in which the distal portion is shaped so as to define both the end mill cutter surfaces and at least one self-tapping surface.

13. The method according to claim 11, wherein providing the dental implement comprises providing the dental implement in which the end mill cutter surfaces do not extend into a cylindrical area of the implement, a central axis of which area coincides with a central axis of the implement, which area extends along the entire length of the implement, and which cylindrical area has a diameter of at least 0.3 mm.

14. The method according to claim 11, wherein providing the dental implement comprises providing the dental implement in which the end mill cutter surfaces include exactly three end mill cutter surfaces.

15. The method according to claim 11, wherein providing the dental implement comprises providing a dental implant.

16. The method according to claim 15, wherein rotating the dental implement comprises rotating the dental implant manually using a wrench.

17. The method according to claim 11, wherein providing the dental implement comprises providing a dental osteotome.

18. The method according to claim 17, wherein rotating the dental implement comprises rotating the dental osteotome manually using a wrench.

19. The method according to claim 11, wherein providing the dental implement comprises providing the dental implement having a proximal-most part, a lateral external surface, and a proximal external surface, and wherein the implement is shaped such that the lumen has a lateral opening through the lateral external surface, and the lumen is not open to the proximal external surface of the implement within 2 mm of the proximal-most part of the implement.

20. The method according to claim 11, wherein providing the dental implement comprises providing the dental implement in which at least a portion of a lateral external surface of the implement is shaped so as to define a cutting surface.

21. The method according to claim 20, wherein providing the dental implement comprises providing the dental implement in which the cutting surface defined by the at least a portion of the lateral external surface comprises a screw thread.

22. The method according to claim 11, wherein providing the dental implement comprises providing the dental implement in which at least a portion of a lateral external surface of the dental implement is shaped so as to define a screw thread.

* * * * *